(12) United States Patent
Michaelsen et al.

(10) Patent No.: US 10,882,919 B2
(45) Date of Patent: Jan. 5, 2021

(54) ANTIBODIES AGAINST HPA-1A

(71) Applicant: Rallybio IPA, LLC, Farmington, CT (US)

(72) Inventors: Terje Michaelsen, Hagan (NO); Oistein Ihle, Ski (NO); Tor Brynjar Stuge, Tromso (NO); Anne Husebekk, Tromso (NO); Heidi Tiller, Tromso (NO); Mariana Eksteen, Tromso (NO); Bjorn Ragnar Skogen, Tromso (NO)

(73) Assignee: Rallybio IPA, LLC, New Haven, CT (US)

( * ) Notice: Subject to any disclaimer, the term of this patent is extended or adjusted under 35 U.S.C. 154(b) by 64 days.

(21) Appl. No.: 15/300,656

(22) PCT Filed: Mar. 31, 2015

(86) PCT No.: PCT/EP2015/057102
§ 371 (c)(1),
(2) Date: Sep. 29, 2016

(87) PCT Pub. No.: WO2015/150417
PCT Pub. Date: Oct. 8, 2015

(65) Prior Publication Data
US 2017/0121422 A1    May 4, 2017

(30) Foreign Application Priority Data

Mar. 31, 2014 (GB) ................................. 1405775.6
Oct. 6, 2014 (GB) ................................. 1417614.3

(51) Int. Cl.
C07K 16/34    (2006.01)
C07K 16/28    (2006.01)
G01N 33/68    (2006.01)

(52) U.S. Cl.
CPC .......... *C07K 16/34* (2013.01); *C07K 16/2848* (2013.01); *G01N 33/6893* (2013.01); *C07K 2317/51* (2013.01); *C07K 2317/515* (2013.01); *C07K 2317/54* (2013.01); *C07K 2317/56* (2013.01); *C07K 2317/565* (2013.01); *C07K 2317/70* (2013.01); *C07K 2317/76* (2013.01); *C07K 2317/92* (2013.01); *G01N 2333/705* (2013.01); *G01N 2800/38* (2013.01)

(58) Field of Classification Search
None
See application file for complete search history.

(56) References Cited

U.S. PATENT DOCUMENTS

| | | | |
|---|---|---|---|
| 6,479,246 B1 * | 11/2002 | Bessos | G01N 33/54306 435/7.1 |
| 7,566,772 B2 | 7/2009 | Green et al. | |
| 7,597,889 B1 * | 10/2009 | Armour | A61P 11/06 424/133.1 |
| 7,868,140 B2 | 1/2011 | Siu et al. | |
| 8,003,098 B2 | 8/2011 | Nakatsuru et al. | |
| 8,080,242 B2 | 12/2011 | Rigal et al. | |
| 8,529,903 B2 | 9/2013 | Daftary et al. | |
| 8,840,897 B2 * | 9/2014 | Skogen | C07K 16/34 424/173.1 |
| 2003/0027207 A1 | 2/2003 | Filpula | |
| 2007/0042949 A1 | 2/2007 | Urbaniak et al. | |
| 2008/0261205 A1 | 10/2008 | Denomme | |
| 2009/0047290 A1 | 2/2009 | Ni et al. | |
| 2009/0117128 A1 | 5/2009 | Rigal et al. | |
| 2009/0317413 A1 | 12/2009 | Stafford et al. | |
| 2009/0318363 A1 | 12/2009 | Rigal et al. | |
| 2010/0173292 A1 | 7/2010 | Taniue et al. | |
| 2011/0293633 A1 | 12/2011 | Skogen et al. | |

FOREIGN PATENT DOCUMENTS

| | | |
|---|---|---|
| CN | 101892314 A | 11/2010 |
| EP | 2796881 A1 | 10/2014 |
| JP | 2002-122595 A | 4/2002 |
| RU | 2226196 C2 | 3/2004 |
| WO | 94/11740 A1 | 5/1994 |
| WO | 96/29600 A1 | 9/1996 |
| WO | 98/55146 A1 | 12/1998 |
| WO | 9958572 A1 | 11/1999 |
| WO | 2007/078202 A1 | 7/2007 |

OTHER PUBLICATIONS

Janeway etal., Immunobiology, 3rd edition, 19097, Garland Press, pp. 3:1-3:11.*
Rudikoff et al., Proc Natl Acad Sci USA. Mar. 1982;79(6): 1979-83.*
Eksteen et al., Vox Sanguinis, (Jul. 2010) vol. 99, Supp. Suppl. 1, pp. 52-53. Abstract Number: 4D-S29-05. Meeting Info: 31st International Congress of the International Society of Blood Transfusion in Joint Cooperation with the 43rd Congress of the DGTI. Berlin, Germany. Jun. 26, 2010-Jul. 1, 201.*
Eksteen et al., Vox Sanguinis, (Oct. 2010) vol. 99, Supp. Suppl. 2, pp. 13. Abstract Number: OA05. Meeting Info: 11th European Symposium on Platelet and Granulocyte Immunobiology. Beaune, Bourgogne, France. Oct. 21-24, 2010.*
Chung et al., MAbs. May 1, 2012; 4(3): 326-340.*
Janeway et al., Immunobiology, 3rd edition 1997, Garland Publishing Inc., pp. 3:26-3:31.*
Allen, D. et al.,"Collaborative study to establish the first international standard for quantification of anti-HPA_1a," Vox Sanguinis, 2005, v.89; pp. 100-104.
Allen D. L., et al., "Human platelet antigen 1a epitopes are dependent on the cation-regulated conformation of integrin aIIbβ3 (GPIIb/IIIa)," J Immunol Methods. Jan. 31, 2012;375(1-2):166-75.

(Continued)

*Primary Examiner* — Michael Szperka
(74) *Attorney, Agent, or Firm* — Grimes & Yvon LLP

(57) ABSTRACT

The present invention provides an isolated antibody that specifically binds to HPA-1a. Also provided is a nucleic acid molecule that encodes the antibody, and compositions comprising the antibody. Also provided is a method of producing the antibody and methods and uses which employ the antibody. Also provided are therapeutic uses of the antibody, for example in the treatment or prophylaxis of fetal and neonatal alloimmune thrombocytopenia (FNAIT).

17 Claims, 18 Drawing Sheets

Specification includes a Sequence Listing.

(56) References Cited

OTHER PUBLICATIONS

Bakchoul T. et al., "Blockade of maternal anti-HPA-1a-mediated platelet clearance by an HPA-1a epitope-specific F(ab')2 in an in vivo mouse model of alloimmune thrombocytopenia," Transfusion. Feb. 2009; 49(2):265-70.
Garner et al., "A rapid one-stage whole-blood HPA-1a phenotyping assay using a recombinant monoclonal IgG1 anti-HPA-1a," British Journal of Haematology, 2000;108(2):440-7.
Ghevaert, Cedric, et al. "Recombinant human HPA-1A antibodies for treatment of fetomaternal alloimmune thrombocytopenia (FMAIT): proof of principle in an in vivo murine model and human volunteer studies." Blood 112.11(2008): 85-85.
Ghevaert et al., "Developing recombinant HPA-1a-specific antibodies with abrogated Fcγ receptor binding for the treatment of fetomaternal alloimmune thrombocytopenia," J. Clin. Invest. Aug. 2008;118(8):2929-38.
Griffin H. et al., "A Human Monoclonal Antibody Specific for the Leucine-33 (P1A1, HPA-1a) Form of Platelet Glycoprotein IIIa From a V Gene Phage Display Library," Blood 1995;86(12):4430-6.
Jackson D. J., et al., "Human platelet antigen (HPA)-1a peptides do not reliably suppress anti-HPA-1a responses using a humanized severe combined immunodeficiency (SCID) mouse model," Clin Exp Immunol., 2013, Apr.; 176(1):23-36.
Joutsi-Korhonen L et al., "The effect of recombinant IgG antibodies against the leucine-33 form of the platelet 3 integrin (HPA-1a) on platelet function," Thromb Haemost. Apr. 2004;91(4):743-54.
Kjeldsen-Kragh J., et al., "Towards a prophylactic treatment of HPA-related foetal and neonatal alloimmune thrombocytopenia," Curr Opin Hematol. Nov. 2012;19(6):469-74.
Kumpel et al., "Ultrastructural localization of glycoprotein IIIa (GPIIIa, β3 integrin) on placental syncytiotrophoblast microvilli: implications for platelet alloimmunization during pregnancy," Transfusion, 2008,v 48: 2077-86.
Liu L.X. et al., "Inhibition of Binding of Anti-PLA' Antibodies to Platelets With Monoclonal Antibody LK-4. Evidence for Multiple PLA' Receptor Sites on Platelet GPIIIa," Blood, 1996;88(9):3601-7.
Liu L.X. et al., "A monoclonal antibody (LK-4) which differentiates PLA1 from PLA2 platelet extracts but not intact platelets," Thrombosis Research, 1992,v 66: 309-20.
Mathiesen et al., "Maternofetal transplacental transport of recombinant IgG antibodies lacking effector functions," Blood (2013) 122(7):1174-81.
Okamoto N., et al. "Identification of a human heavy chain antibody fragment directed against human platelet alloantigen 1a by phage display library," 1998. Tissue Antigens 51: 156-63.
Peyruchaud O. et al., "HPA-10wb (Laa): Genetic Determination of a New Platelet-Specific Alloantigen on Glycoprotein IIIa and Its Expression in COS-7 Cells," Blood, Apr. 1, 1997 vol. 89 No. 7, 2422-2428.
Proulx et al., "Human Monoclonal Fab Fragments Recovered from a Combinatorial Library Bind Specifically to the Platelet HPA-1a Alloantigen on Glycoprotein IIb-IIIa," Vox Sanguinis, 1997, 72: 52-60.
Ryckewaert JJ, et al., "Production of anti-P1A monoclonal antibodies," 1992. J Lab Clin Med 119: 52-6.
Santoso S., et al., "A naturally occurring Leu33Val mutation in β3-integrin impairs the HPA-1a epitope: the third allele of HPA-1," Transfusion. 2006;46(5):790-9.
Smethurst P. A., et al., "Identification of the primary collagen-binding surface on human glycoprotein VI by site-directed mutagenesis and by a blocking phage antibody," Blood 2004;103(3):903-11.
Stafford P. et al., "Immunologic and structural analysis of eight novel domain-deletion β3 integrin peptides designed for detection of HPA-1 antibodies," J. Thrombosis and Haemostasis, 2008;6(2)366-75.
Valentin N. et al., "Involvement of the Cysteine-Rich Domain of Glycoprotein IIIa in the Expression of the Human Platelet Alloantigen, P1A1: Evidence for Heterogeneity in the Humoral Response," Blood, 1995;85(11)3028-33.
Vanderpuye O. A., et al., "A vitronectin-receptor-related molecule in human placental brush border membranes," (1991), Biochem J 280 (Pt 1): 9-17.
Weiss E.J., et al., "A monoclonal antibody (SZ21) specific for platelet GPIIIa distinguishes P1A1 from P1A2," Tissue Antigens. 1995;46(5)374-81.
Bakchoul, T. et al., "Inhibition of HPA-1a alloantibody-mediated platelet destruction by a deglycosylated anti-HPA-1a monoclonal antibody in mice: toward targeted treatment of fetal-alloimmune thrombocytopenia," Blood, 2013, v. 122, pp. 321-327.
Eksteen, M. et al., "A Novel Human Monoclonal HPA-1a-Specific Antibody is a Useful Tool for Diagnostics in Fetal and Neonatal Alloimmune Thrombocytopenia," Vox Sanguinis, 2013, Suppl. 1, vol. 105, P-518 (abstract), p. 240.
Ghevaert, C. et al., "Recombinant HPA-1a antibody therapy for treatment of fetomaternal alloimmune thrombocytopenia: proof of principle in human volunteers," Blood, 2013, v. 122, pp. 313-320.
Search Report and Written Opinion for International Application No. PCT/EP2015/057102, dated Jul. 7, 2015 (10 pages).
Tiller, H., et al., "Administration of Anti-Platelet Antibodies Prevents the Anti-Platelet Immune Response and Bleeding Complications of Neonatal Immune Thrombocytopenia in a Murine Model," Blood, Amer. Soc. of Hematology, 2009, v. 114, p. 97.
Ohno, et al., Antigen-binding specificities of antibodies of antibodies are primarily determined by seven residues of Vh, (1985) P.N.A.S. vol. 82, pp. 2945-2949.
Ching, C. et al., "Generation and Analysis of Random Point Mutations in an Antibody CDR2 Sequence: Many Mutated Antibodis Lose Their Ability of Bind Antigen," (1992) J. Exp. Med. vol. 176, pp. 855-866.
Eksteen Abstract (Jul. 2010).
Eksteen Abstract, (Oct. 2010).
Bernasconi, NL. et al. Maintenance of Serological Memory by Polyclonal Activation of Memory B Cells; Science 298:2199-2202 (2002).
Eksteen, M. et al. Generation of monoclonal anti-HPA-1a antibodies by immortalization of memory B cells of a woman alloimmunized in connection with pregnancy; sl. 1-11 (2010a).
Eksteen, M. et al. A high affinity monoclonal anti-HPA-1a antibody derived from memory B cells of a woman alloimmunized in connection with pregnancy; slides 1-5 (2010b).
He, B. et al. Activating Human B Cells through an Innate Pathway That Requires TLR9 and Cooperates with IL-10; J. Immunol. 173:4479-4491 (2004).
Siegrist, C. Vaccine Immunology in Plotkin's Vaccines, 7th Ed., Plotkin S.A. et al. Eds.; Elsevier; pp. 16-34.e7 (2018).

* cited by examiner

| Light chain | | |
|---|---|---|
| 26.4 IGKV | FR1 | E I V L T Q S P A T L S L S P G E R A T L S C |
| | | gaa att gtg ttg aca cag tct cca gcc acc ctg tct ttg tca gga gaa aga gcc acc ctc tcc tgc |
| IGKV3-11*01 | | ----------------------------------------t----------------------------------------- |
| 26.4 IGKV | CDR1 | R A S Q S V ... I Y ... L A |
| | | agg gcc agt cag agt gtt ... agc tac ... tta gcc |
| IGKV3-11*01 | | ----------S--------- |
| 26.4 IGKV | FR2 | W Y Q Q K P G Q A P R L |
| | | tgg tac cag cag aaa cct ggc cag gct ccc agg ctc |
| IGKV3-11*01 | | |
| 26.4 IGKV | CDR2 | L I Y ... D A S ... |
| | | ctc atc tat ... gat gca tcc ... |
| | | T N |
| IGKV3-11*01 | | -----c---------- |
| 26.4 IGKV | FR3 | S R A T G I P A R F S G S G S G T |
| | | agc aga gcc act ggc atc cca gcc agg ttc agt ggc agt ggg tct ggg aca |
| IGKV3-11*01 | | |
| 26.4 IGKV | | E F T L T I S S L E P E D F A V Y Y C |
| | | gac ttc acc ctc acc atc agc agc cta gag cct gaa gat ttt gca gtt tat tac tgt |
| IGKV3-11*01 | | ------------T-----------c------g--------- |
| 26.4 IGKV | CDR3 | Q Q R S ... |
| | | caa cag cgt agc ... |
| IGKV3-11*01 | | -----------------g- |
| 26.4 IGKV | FR4 | ... F G Q G T K V E I K |
| | | ... ttc ggc gga ggg acc aag gtg gag atc aaa |
| | | N P |
| IGKV3-11*01 | | a----- -ct cc |

ANTIBODIES AGAINST HPA-1A

Priority is claimed under 35 U.S.C. § 119 to British Application Nos. 1405775.6 filed on Mar. 31, 2014 and 1417614.3, filed on Oct. 6, 2014, respectively, and under 35 U.S.C. § 365 to PCT/EP2015/057102 filed on Mar. 31, 2015.

The present invention relates generally to the field of antibodies, in particular to antibodies against HPA-1a (human platelet antigen-1a). The invention further relates to compositions and immunoconjugates comprising such antibodies and to methods of producing such antibodies. The invention also relates to methods of detecting for the presence or absence of HPA-1a in a sample and methods for the treatment, prophylaxis, and diagnosis of FNAIT (fetal and neonatal alloimmune thrombocytopenia).

Human platelet alloantigens HPA-1a and HPA-1b are defined by a single nucleotide mutation resulting in a leucine to proline substitution at position 33 on the β3 chain of αIIbβ3 platelet integrin (glycoprotein IIbIIIa). Carriers of a leucine at position 33 of the β-integrin chain are defined as HPA-1a positive, whereas homozygous carriers of a proline at position 33 of the β-integrin chain are defined as HPA-1a negative (HPA-1bb).

About 2% of Caucasians are homozygous for HPA-1b (P33). Women with this phenotype may become immunized to HPA-1a in connection with pregnancy, when the fetus has a paternally-inherited HPA-1a allotype.

Mismatch between fetal and maternal HPA-1 alloantigens may lead to maternal immunization with the production of IgG anti-HPA-1a antibodies. These antibodies can traverse the placenta, bind fetal platelets and may accelerate platelet destruction causing FNAIT. FNAIT is a serious complication in foetal and neonatal development. Anti-HPA-1a antibodies account for most (85-90%) of FNAIT cases, and are often involved in post-transfusion purpura (PTP) and in platelet transfusion refractoriness.

Maternal anti-HPA-1a antibodies produced during a non-compatible pregnancy can traverse the placenta and cause FNAIT in the fetus of a first pregnancy (i.e. in the fetus being carried at the time of maternal immunization). Such fetuses may develop severe thrombocytopenia very early during pregnancy. During such a first pregnancy, FNAIT is often not detected until birth when the newborn presents with classic symptoms of thrombocytopenia.

As well as affecting a first non-compatible pregnancy, the recurrence of FNAIT in subsequent non-compatible pregnancies (i.e. pregnancies in which a mother who was immunised to the HPA-1 alloantigen in connection with a first pregnancy is pregnant again with a HPA-1a positive fetus) has been estimated to be more than 80%. Immunisation with the HPA-1a alloantigen may also occur in connection with delivery, which means that a subsequent non-compatible pregnancy may be a risk of FNAIT even if the first fetus/newborn was unaffected. Currently, there is no safe and effective strategy to treat or prevent FNAIT. Furthermore, the condition is usually not evident until after delivery of a severely thrombocytopenic child. Thus, efficient management of FNAIT will depend on introduction of general screening to identify at-risk pregnancies, and development of prophylaxis and new treatment approaches.

For hemolytic disease of the fetus and newborn (HDFN), a pregnancy related disorder caused by antibodies reactive with a fetal red cell alloantigen, an effective antibody-based prophylaxis has been in routine use for decades. A large prospective screening study in Norway revealed that HPA-1a immunization can occur in connection with delivery, and therefore, similar to HDFN, prophylaxis with anti-HPA-1a antibodies may thus prevent FNAIT. Furthermore, experiments employing a murine model of FNAIT suggested that immunization against HPA-1a can be prevented by administration of HPA-1a-specific antibodies in connection with delivery. As a consequence of the above findings, clinical trials are underway to test the potential of hyperimmune anti-HPA-1a IgG isolated from donor plasma in preventing HPA-1a immunization in connection with pregnancy. Hyperimmune anti-HPA-1a IgG is IgG extracted from women HPA-1a-alloimmunized in connection with pregnancy.

The inventors believe that an attractive source of anti-HPA-1a antibodies for eventual FNAIT prophylaxis or therapy is recombinant monoclonal antibodies (mAbs). In contrast to IgG preparations extracted from donor plasma, mAbs may be produced in virtually limitless amounts, the specificity and function of mAbs can be characterized in detail, and a therapeutic dose can be determined more accurately providing more reproducibility in treatment. Anti-HPA-1a mAbs would also be of great value as a screening reagent to identify whether women are HPA-1a positive or HPA-1a negative.

The reported human HPA-1a-specific recombinant mAbs have been developed from antibody fragments isolated by phage display. It has been suggested that antibodies with randomly paired heavy and light chains in vitro (e.g. antibodies prepared by phage display) may represent foreign proteins or be autoreactive and therefore are more likely to induce undesirable immune reactions in recipients.

Several mAbs which bind to HPA-1a exist. Two such mAbs were generated in mice by conventional hybridoma technology. One of these, clone LK-4, differentiates HPA-1a from HPA-1b antigens on platelet extracts but not when present on intact platelets while a second, SZ21, binds HPA-1a on intact platelets. However, the SZ21 mAb also binds detectably to HPA-1a-negative platelets when used at increasing antibody concentrations.

What are needed in the art are new, preferably improved, agents, such as antibodies, that can be used for the treatment, prophylaxis and diagnosis of FNAIT and for detecting the presence or absence of (i.e. screening for) the presence or absence of the HPA-1a alloantigen in a subject.

The present inventors have identified monoclonal antibodies which bind specifically to HPA-1a. Using B-cells from a HPA-bb woman who had become immunized in connection with pregnancy with a HPA-1a-positive child, the inventors prepared a clonal B cell line generated by EBV-transformation of memory B-cells and selected single B-cells which produced anti-HPA-1a antibodies. The inventors also prepared recombinant versions of these antibodies. The antibodies generated by the inventors have advantageous properties which make them ideal agents for the above-mentioned uses.

Thus, in a first aspect, the present invention provides an isolated antibody that specifically binds to HPA-1a and that comprises at least one heavy chain variable region that comprises three CDRs and at least one light chain variable region that comprises three CDRs, wherein said light chain variable region comprises:
  (a) a variable light (VL) CDR1 that has the amino acid sequence of SEQ ID NO:8 or a sequence substantially homologous thereto,
  (b) a VL CDR2 that has the amino acid sequence of SEQ ID NO:9 or a sequence substantially homologous thereto, and (c) a VL CDR3 that has the amino acid sequence of SEQ ID NO:10 or a sequence substantially homologous thereto; and wherein said heavy chain variable region comprises:
(d) a variable heavy (VH) CDR1 that has the amino acid sequence of SEQ ID NO:5 or a sequence substantially homologous thereto,
(e) a VH CDR2 that has the amino acid sequence of SEQ ID NO:6 or a sequence substantially homologous thereto, and
(f) a VH CDR3 that has the amino acid sequence of SEQ ID NO:7 or a sequence substantially homologous thereto.

In a preferred embodiment, the invention provides an antibody that specifically binds to HPA-1a and that comprises:
a VL domain that comprises a VL CDR1 of SEQ ID NO:8, a VL CDR2 of SEQ ID NO:9, and a VL CDR3 of SEQ ID NO:10, and
a VH domain that comprises a VH CDR1 of SEQ ID NO:5, a VH CDR2 of SEQ ID NO:6, and a VH CDR3 of SEQ ID NO:7.

Certain preferred embodiments of the invention provide an antibody that specifically binds to HPA-1a comprising a VH domain that comprises the amino acid sequence of SEQ ID NO:3 or a sequence substantially homologous thereto and/or a VL domain that comprises the amino acid sequence of SEQ ID NO:4, or a sequence substantially homologous thereto.

Further preferred embodiments provide an antibody that specifically binds to HPA-1a comprising a VH domain that comprises the amino acid sequence of SEQ ID NO:3 and a VL domain that comprises the amino acid sequence of SEQ ID NO:4.

Other preferred embodiments of the invention are full length IgG forms (e.g. IgG1 or IgG3) of the antibodies described herein. Thus, a preferred embodiment of the invention provides an antibody that that specifically binds to HPA-1a which has a heavy chain that comprises the amino acid sequence of SEQ ID NO:21 or a sequence substantially homologous thereto and/or a light chain that comprises the amino acid sequence of SEQ ID NO:22 or a sequence substantially homologous thereto. In another preferred embodiment the invention provides an antibody that specifically binds to HPA-1a which has a heavy chain that comprises the amino acid sequence of SEQ ID NO:25 or a sequence substantially homologous thereto and/or a light chain that comprises the amino acid sequence of SEQ ID NO:26 or a sequence substantially homologous thereto.

In a particularly preferred embodiment, an antibody comprises a heavy chain that comprises the amino acid sequence of SEQ ID NO:21 and a light chain that comprises the amino acid sequence of SEQ ID NO:22.

In another particularly preferred embodiment, an antibody comprises a heavy chain that comprises the amino acid sequence of SEQ ID NO:25 and a light chain that comprises the amino acid sequence of SEQ ID NO:26.

The invention is exemplified by the monoclonal antibody D18BL26.4 (see the Examples section, also referred to herein as "26.4"). The CDR domains, VH and VL domains and full length IgG chains of the 26.4 antibody are shown in Table 1. Antibodies comprising these CDR domains, VH and VL domains, or IgG chains (or sequences substantially homologous thereto) are preferred aspects of the invention. The antibody 26.4, including recombinant versions thereof, represent preferred embodiments of the invention.

The present invention also provides binding proteins that specifically bind to HPA-1a and that comprise an antibody of the invention.

As used herein, the term "that specifically binds to HPA-1a" in the context of antibodies or antibody fragments of the present invention, means antibodies or antigen binding fragments that are capable of binding to the alloantigen HPA-1a and which do not cross-react with the alloantigen HPA-1b (i.e. exhibit no significant binding to the HPA-1b alloantigen). The 26.4 antibody exemplified herein is an example of an antibody that specifically binds to HPA-1a.

In one embodiment, an antibody of the invention does not cross-react with HPA-1b when used at a concentration of 10 µg/ml to 20 µg/ml in the IgG format (e.g. 10 µg/ml or 20 µg/ml), for example when tested against HPA-1b antigen in a Surface Plasmon Resonance assay (e.g. the assay described in Example 1). Antibodies that are only pseudospecific for HPA-1a are not deemed to specifically bind to HPA-1a in accordance with the present invention.

Of course, antibody which "binds specifically to HPA-1a" in accordance with the present invention does not cross-react with other HPA or non-HPA antigens.

Certain examples of substantially homologous sequences are sequences that have at least 70% identity to the amino acid sequences disclosed.

In certain embodiments, the antibodies of the invention that bind specifically to HPA-1a comprise at least one light chain variable region that includes an amino acid sequence region of at least about 70% or 75%, more preferably at least about 80%, more preferably at least about 85%, more preferably at least about 90% or 95% and most preferably at least about 97%, 98% or 99% amino acid sequence identity to the amino acid sequence of SEQ ID NO:4; and/or at least one heavy chain variable region that includes an amino acid sequence region of at least about 70% or 75%, more preferably at least about 80%, more preferably at least about 85%, more preferably at least about 90% or 95% and most preferably at least about 97%, 98% or 99% amino acid sequence identity to the amino acid sequence of SEQ ID NO:3.

Other preferred examples of substantially homologous sequences are sequences containing conservative amino acid substitutions of the amino acid sequences disclosed.

Other preferred examples of substantially homologous sequences are sequences containing 1, 2 or 3, preferably 1 or 2, altered amino acids in one or more of the CDR regions disclosed. Such alterations might be conserved or non-conserved amino acid substitutions, or a mixture thereof.

In all such embodiments, preferred alterations are conservative amino acid substitutions.

In a preferred embodiment, the invention provides an isolated antibody that specifically binds to HPA-1a and that comprises at least one heavy chain variable region that comprises three CDRs and at least one light chain variable region that comprises three CDRs, wherein said light chain variable region comprises:
(a) a variable light (VL) CDR1 that has the amino acid sequence of SEQ ID NO:8 or a sequence substantially homologous thereto,
(b) a VL CDR2 that has the amino acid sequence of SEQ ID NO:9 or a sequence substantially homologous thereto and
(c) a VL CDR3 that has the amino acid sequence of SEQ ID NO:10 or a sequence substantially homologous thereto; and wherein said heavy chain variable region comprises:
(d) a variable heavy (VH) CDR1 that has the amino acid sequence of SEQ ID NO:5 or a sequence substantially homologous thereto,
(e) a VH CDR2 that has the amino acid sequence of SEQ ID NO:6 or a sequence substantially homologous thereto, and
(f) a VH CDR3 that has the amino acid sequence of SEQ ID NO:7 or a sequence substantially homologous thereto; and wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

In another preferred embodiment, the present invention provides an antibody which specifically binds to HPA-1a, wherein the light chain variable region has the amino acid sequence of SEQ ID NO:4, or a sequence having at least 80% sequence identity thereto and/or wherein the heavy chain variable region has the amino acid sequence of SEQ ID NO:3, or a sequence having at least 80% sequence identity thereto.

In all embodiments, the antibodies containing substantially homologous sequences retain the ability to specifically bind to HPA-1a and preferably retain one or more of the other properties described herein, more preferably all of the properties described in relation to the 26.4 antibody.

Further examples of substantially homologous amino acid sequences in accordance with the present invention are described elsewhere herein.

The CDRs of the antibodies of the invention are preferably separated by appropriate framework regions such as those found in naturally occurring antibodies and/or effective engineered antibodies. Thus, the $V_H$, $V_L$ and individual CDR sequences of the invention are preferably provided within or incorporated into an appropriate framework or scaffold to enable antigen binding. Such framework sequences or regions may correspond to naturally occurring framework regions, FR1, FR2, FR3 and/or FR4, as appropriate to form an appropriate scaffold, or may correspond to consensus framework regions, for example identified by comparing various naturally occurring framework regions. Alternatively, non-antibody scaffolds or frameworks, e.g., T cell receptor frameworks can be used.

Appropriate sequences that can be used for framework regions are well known and documented in the art and any of these may be used. Preferred sequences for framework regions are one or more of the framework regions making up the $V_H$ and/or $V_L$ domains of the invention, i.e., one or more of the framework regions of the 26.4 antibody, as disclosed in Table 1, or framework regions substantially homologous thereto, and in particular framework regions that allow the maintenance of antigen specificity, for example framework regions that result in substantially the same or the same 3D structure of the antibody. In certain preferred embodiments, all four of the variable light chain (SEQ ID NOs:15, 16, 17 and 18) and/or variable heavy chain (SEQ ID NOs:11, 12, 13 and 14) framework regions (FR), as appropriate, or FR regions substantially homologous thereto, are found in the antibodies of the invention.

Without wishing to be bound by theory, it is believed that a good system for selecting for clinically useful anti-HPA-1a antibodies is to harness the selective mechanism in the immune response raised against HPA-1a in HPA-1a negative individuals, i.e. the immune response raised to HPA-1a in HPA-1a negative individuals who have become immunised in connection with a non-compatible pregnancy (a pregnancy with a HPA-1a positive fetus). Memory B cells that are selected in such responses should have receptors that react well to HPA-1a, but not be reactive to the allogeneic antigen HPA-1b (i.e. "self"). Antibodies selected from memory B cells of such an individual would thus be expected to be highly specific for HPA-1a and not to cross-react with HPA-1b (which only differs from HPA-1a by a single amino acid polymorphism). Furthermore, as an antibody selected by such a system is selected by nature (i.e. by a human immune system) it means that, when used clinically, there should be a reduced risk of anaphylaxis, autoreactivity and/or toxicity, and/or the antibody should not be rapidly removed from the circulation, as compared to, for example, an antibody selected in vitro from a library (e.g. by phage display). The antibodies of the present invention are based on the antibody 26.4, which was selected in such a manner. The 26.4 antibody was derived from a single B-cell of a HPA-1a negative woman who was HPA-1a alloimmunised in connection with pregnancy.

Thus, preferably the antibodies of the present invention have a low risk of causing anaphylaxis and/or toxicity when used clinically. Preferably, the antibodies of the invention are not autoreactive. In certain embodiments, the antibodies of the invention are not rapidly cleared from the circulation.

As described above, antibodies of the invention bind specifically to HPA-1a. Preferably, the antibodies bind to HPA-1a on intact platelets. Assays to ascertain whether antibodies bind to HPA-1a on intact HPA-1a positive platelets include, but are not limited to flow cytometry (e.g. whole blood flow cytometry) or the MAIPA assay (monoclonal antibody immobilization of platelet antigens assay). Suitable flow cytometry and MAIPA assays are described in the Examples.

In certain embodiments, the antibodies of the invention are capable of binding to purified forms of HPA-1a or HPA-1a bearing proteins. As described above, the HPA-1a antigen is present in αIIbβ3 platelet integrin (glycoprotein IIbIIIa). Preferably, antibodies of the present invention are capable of binding to purified αIIbβ3 platelet integrin from HPA-1a positive individuals. Methods for purifying αIIbβ3 platelet integrin are known in the art, as are methods for determining whether an antibody is able to bind to a purified protein. For example, Example 1 describes a method for purifying (isolating) αIIbβ3 platelet integrin from platelets. Example 1 also describes how Surface Plasmon Resonance can be used to analyse the binding of purified forms of HPA-1a or HPA-1a bearing proteins. Preferred antibodies remain at least 50% bound to a purified and immobilised αIIbβ3 platelet integrin from HPA-1a positive individuals at the end of the dissociation period in a Surface Plasmon Resonance assay. Preferably, at least 60%, at least 70%, at least 80% or at least 90% of the antibody remains bound at the end of the dissociation period in a Surface Plasmon Resonance assay. For example, about 50% to about 80% of the antibody remains bound. A preferred association period in such a Surface Plasmon Resonance assay is 120 seconds. A preferred dissociation period in such a Surface Plasmon Resonance assay is 120 seconds. A particularly preferred Surface Plasmon Resonance assay is described in Example 1.

αVβ3 integrin is another β3 integrin-containing heterodimer (vitronectin receptor). αVβ3 is expressed on fetal trophoblast cells. αVβ3 integrin on fetal trophoblast cells obtained from a HPA-1a positive individual (e.g. a HPA-1a homozygous individual) or purified from such an individual contains the HPA-1a antigen. Thus, antibodies which bind specifically to αVβ3 integrin from HPA-1a positive individuals are considered antibodies that specifically bind to HPA-1a in accordance with the present invention.

Fetal trophoblasts, which line the maternal-fetal interphase, are constantly released into the maternal circulation throughout pregnancy. Thus, HPA-1a positive fetal trophoblasts represent a source of HPA-1a for alloimmunization of a woman during a non-compatible pregnancy, i.e. a pregnancy where the mother is HPA-1a negative and the fetus is HPA-1a positive. It is known that some women become immunized to HPA-1a at an early time point in pregnancy, when immunization with fetal platelets is unlikely due to the developmental stage of fetal blood cells. In such cases αVβ3 integrin containing the HPA-1a antigen is the likely immunogen. Thus, antibodies of the present invention which are capable of binding to αVβ3 integrin containing the HPA-1a antigen are preferred.

In certain embodiments, the antibodies of the invention are capable of binding to the HPA-1a antigen on intact fetal trophoblasts.

In certain embodiments, the antibodies of the invention are capable of binding to purified αVβ3 integrin from HPA-1a positive individuals. Methods for purifying αVβ3 integrin are known in the art, as are methods for determining whether an antibody is able to bind to a purified protein. For example, Example 1 describes a method for purifying (isolating) αVβ3 integrin from human placenta. Example 1 also describes how Surface Plasmon Resonance can be used to analyse the binding of purified forms of HPA-1a or HPA-1a bearing proteins. Preferred antibodies remain at least 35% bound to a purified and immobilised αVβ3 integrin from HPA-1a positive individuals at the end of the dissociation period in a Surface Plasmon Resonance assay. Preferably, at least 40%, at least 45%, at least 50%, at least 55%, at least 60% or at least 65% of the antibody remains bound at the end of the dissociation period in a Surface Plasmon Resonance assay. For example, 35% to 70% of the antibody remains bound. A preferred association period in such a Surface Plasmon Resonance assay is 120 seconds. A preferred dissociation period in such a Surface Plasmon Resonance assay is 120 seconds. Suitable antigen (ligand) densities on the chip used in Surface Plasmon Resonance are known in the art and can readily be established (e.g. those of Example 1). A particularly preferred Surface Plasmon Resonance assay is described in Example 1.

Preferably, in Surface Plasmon Resonance experiments, antibodies of the present invention dissociate from purified and immobilised αVβ3 integrin from HPA-1a positive individuals slower than the antibody B2G1 (Griffin H, Ouwehand W., Blood. 1995; 86(12):4430-6). For example, antibodies of the present invention dissociate about 10%, about 20%, about 30%, about 40%, about 50%, about 60%, about 70%, about 80%, about 90% or about 100% slower than the antibody B2G1 (e.g. about 50% to about 100% slower).

Preferably, in Surface Plasmon Resonance experiments, antibodies of the invention have a higher binding response for αVβ3 integrin from HPA-1a positive individuals than the antibody B2G1. Preferably, the binding response is at least 10%, at least 20%, at least 30%, at least 40%, at least 50%, at least 60% or at least 70% higher than for the antibody B2G1 (e.g. about 10% to about 70% higher). Binding response is the response units (RU) value at the end of the association phase.

The amino acid sequences of the heavy chain variable region and light chain variable region of B2G1 are as follows:

Heavy chain variable region of B2G1
(SEQ ID NO: 27)
QVQLVQSGAEVKRPGAAVKVSCKASGYRFTGHYMHWVRQAPGQGLEWMGW

INPNSGGTSYAQKFQGRVTMTRDTSISTAYMEMTRLRYDDTAVYYCAAGG

LGGYYYYAMNIWGQGTTVTVSS

Light chain variable region of B2G1
(SEQ ID NO: 28)
QSALTQPASVSGSPGQSITISCTGTSSDVGGYNYVSWYQQHPGKAPKLMI

YEVSNRPSGVSNRFSGSKSGNTASLTISGLQAEDEADYYCSSYTSSSTWV

FGGGTKLTVL

In some embodiments, antibodies of the invention have the ability to inhibit the binding of the anti-HPA-1a antibody SZ21 to αVβ3 integrin (HPA-1aa genotyped). Inhibition of binding does not necessarily mean a complete block on binding, inhibition includes a significant or measurable reduction in binding. Preferably, the ability to inhibit the binding of the anti-HPA-1a antibody SZ21 to αVβ3 integrin is a dose-dependent ability, i.e. as the concentration of an antibody of the invention increases, the inhibition of binding of the anti-HPA-1a antibody SZ21 to αVβ3 integrin increases. Suitable assays for assessing the ability of a given antibody to inhibit the binding of the anti-HPA-1a antibody SZ21 to αVβ3 integrin are known in the art. In such assays the αVβ3 integrin may be from a cell lysate from a trophoblast cell line (e.g. the TCL-1 cell line, Lewis M P, et al., (1996), Placenta 17: 137-46). A particularly suitable assay is a flow cytometric antibody binding-inhibition assay, for example the flow cytometric antibody binding inhibition assay described in Example 1.

In preferred embodiments, antibodies of the present invention have an increased ability to inhibit the binding of the anti-HPA-1a antibody SZ21 to αVβ3 integrin (HPA-1aa genotyped) compared to the ability of the antibody B2G1 to inhibit the binding of the anti-HPA-1a antibody SZ21 to αVβ3 integrin (HPA-1aa genotyped). Put another way, in some embodiments antibodies of the present invention are more efficient than the antibody B2G1 at inhibiting the binding of the anti-HPA-1a antibody SZ21 to αVβ3 integrin (HPA-1aa genotyped). For example, in some embodiments, when used at an amount of 12.5 ng-200 ng (e.g. 12.5 ng, 25 ng, 50 ng, 100 ng or 200 ng) antibodies of the present invention have an increased ability to inhibit the binding of the anti-HPA-1a antibody SZ21 to αVβ3 integrin (HPA-1aa genotyped) compared to the ability of the antibody B2G1 (used at the same amount/concentrations) to inhibit the binding of the anti-HPA-1a antibody SZ21 to αVβ3 integrin (HPA-1aa genotyped). Typically, the antibodies are used in a fixed volume of 200 µl, so the above-mentioned amounts of 12.5 ng, 25 ng, 50 ng, 100 ng and 200 ng equate to concentrations of 62.5 ng/ml, 125 ng/ml, 250 ng/ml, 500 ng/ml and 1000 ng/ml, respectively. This increased ability is significant and preferred antibodies inhibit as well as antibody 26.4, e.g. as shown in FIG. 5F). Preferred antibodies are at least 20%, preferably at least 30%, more preferably at least 40 or 50% more effective (at any of the aforementioned concentrations) at inhibiting binding of SZ21 to αVβ3 integrin than B2G1 is.

The amino acid sequences of the heavy chain variable region and light chain variable region of SZ21 are as follows:

```
Heavy chain variable region of SZ21
(Genebank Accession Number AF354053)
                                        (SEQ ID NO: 29)
LQESGPELVNPGASMKISCKASGYSFTGYTMNWVKQSHGKNLEWIGLINP

YHGGSSYNQKFKGKATLTVDKSSSTAYMELLSLTSEDSAVYFCARRDANY

VFFFDYWGQGTTVT

Light chain variable region of SZ21
(Genebank Accession Number AF354054)
                                        (SEQ ID NO: 30)
ELTQSPALMSASPGEKVTMTCSASSGVSYIHWYQQKSGTSPKRWIYDTSK

LASGVPARFSGSGSGTSYSLTISSMEAEDAATYYCQQWSSKPPTFGGGTK

LE
```

In preferred embodiments, the antibodies of the invention are capable of inducing phagocytosis of HPA-1a positive platelets. Without wishing to be bound by theory, it is believed that the antibodies act by binding to HPA-1a on platelets and sensitizing/opsonizing the bound platelets for destruction by phagocytes (e.g. monocytes). Thus, the ability to induce phagocytosis of HPA-1a positive platelets is believed to be particularly important in the context of FNAIT prophylaxis. Preferably, antibodies of the invention induce phagocytosis of HPA-1a positive platelets in a concentration dependent manner, with increased phagocytosis being observed as the antibody concentration used increases. In certain embodiments, the antibodies of the invention are capable of inducing phagocytosis when used at a concentration of at least 0.05 µg/ml, for example at a concentration in the range of 0.05 µg/ml to 50 µg/ml, preferably at a concentration of about 0.1 µg/ml to about 10 µg/ml. In preferred embodiments, antibodies induce at least 20% platelet phagocytosis, for example at least 30%, at least 40%, at least 50%, at least 60%, at least 70%, at least 80%, at least 90% phagocytosis or 100% phagocytosis (e.g. about 30% to about 90% phagocytosis). For example, in certain embodiments, antibodies in accordance with the present invention are capable of inducing about 90% HPA-1a homozygous platelet phagocytosis when used at a concentration of 10 µg/ml. Preferably, the antibodies of the invention do not induce phagocytosis of HPA-1a negative platelets. Methods for assessing platelet phagocytosis are known in the art and a suitable assay is described in Example 1. The % phagocytosis value may be the % of monocytes having internalized platelets, e.g. in an assay as described in Example 1. The assay described in Example 1 is a preferred assay for assessing the ability of antibodies of the present invention to induce phagocytosis.

Preferably the antibodies of the invention do not inhibit aggregation of HPA-1bb platelets (e.g. less than 10% inhibition at an antibody concentration of 12 µg/ml). Preferably the antibodies of the invention do not greatly inhibit aggregation of HPA-1ab platelets (e.g. no more than 30%, preferably no more than 20% inhibition at an antibody concentration of 12 µg/ml). This lack of significant inhibitory activity means the antibodies will not impede the function of maternal or fetal platelets. The antibodies of the invention will, in addition, preferably not have an activatory effect on HPA-1a positive platelets (e.g. at an antibody concentration of 12 µg/ml).

Methods for assessing an effect on platelet aggregation are known in the art and a suitable assay is described in Example 1. The assay described in Example 1 is a preferred assay for assessing the ability of antibodies of the present invention to inhibit platelet aggregation.

In some embodiments, the antibodies of the invention are capable of inhibiting the binding of maternal polyclonal anti-HPA-1a IgG to HPA-1a homozygous platelets. In one such embodiment the antibody is preferably a F(ab')2 fragment of the 26.4 antibody. Preferably, the inhibition is at least 60%, at least 65%, at least 70%, at least 75%, at least 80%, at least 85%, at least 90%, at least 95%, or 100%. For example, the inhibition may be 65%-100%. Such inhibition can be assessed using a MAIPA assay, for example as described in Example 3 herein.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

Nucleic acid molecules comprising nucleotide sequences that encode the antibodies of the present invention as defined herein or parts or fragments thereof, or nucleic acid molecules substantially homologous thereto, form yet further aspects of the invention. A preferred nucleic acid is a nucleic acid encoding a heavy chain of an antibody (e.g., those encoding SEQ ID NOs:21 and 25, such as SEQ ID NO:19 and SEQ ID NO:23, respectively) or those encoding a light chain of an antibody (e.g., those encoding SEQ ID NOs:22 and 26, such as SEQ ID NOs:20 and 24). Other preferred nucleic acid molecules are those encoding a VH region of an antibody of the present invention (e.g., those encoding SEQ ID NO:3, such as SEQ ID NO:1). Other preferred nucleic acid molecules are those encoding a VL region of an antibody of the present invention (e.g., those encoding SEQ ID NO:4, such as SEQ ID NO:2).

The term "substantially homologous" as used herein in connection with an amino acid or nucleic acid sequence includes sequences having at least 70% or 75%, preferably at least 80%, and even more preferably at least 85%, 90%, 95%, 96%, 97%, 98% or 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level preferred substantially homologous sequences contain up to 5, e.g. only 1, 2, 3, 4 or 5, preferably 1, 2 or 3, more preferably 1 or 2, altered amino acids, in one or more of the framework regions and/or one or more of the CDRs making up the sequences of the invention. Said alterations can be with conservative or non-conservative amino acids. Preferably said alterations are conservative amino acid substitutions.

The term "substantially homologous" also includes modifications or chemical equivalents of the amino acid and nucleotide sequences of the present invention that perform substantially the same function as the proteins or nucleic acid molecules of the invention in substantially the same way. For example, any substantially homologous antibody should retain the ability to bind to HPA-1a as described above. Preferably, any substantially homologous antibody should retain one or more of the functional capabilities of the starting antibody.

Preferably, any substantially homologous antibody should retain the ability to specifically bind to the same epitope of HPA-1a as recognized by the antibody in question, for example, the same epitope recognized by the CDR domains of the invention or the VH and VL domains of the invention as described herein. Binding to the same epitope/antigen can be readily tested by methods well known and described in the art, e.g., using binding assays, e.g., a competition assay. Retention of other functional properties can also readily be tested by methods well known and described in the art.

Thus, a person skilled in the art will appreciate that binding assays can be used to test whether "substantially homologous" antibodies have the same binding specificities as the antibodies and antibody fragments of the invention, for example, binding assays such as ELISA assays or BIAcore assays can readily be used to establish whether such "substantially homologous" antibodies can bind to HPA-1a. As outlined below, a competition binding assay can be used to test whether "substantially homologous" antibodies retain the ability to specifically bind to substantially the same epitope of HPA-1a as recognized by the antibodies of the invention (e.g. 26.4), or have the ability to compete with one or more of the various antibodies of the invention (e.g. 26.4). The method described below is only one example of a suitable competition assay. The skilled person will be aware of other suitable methods and variations.

An exemplary competition assay involves assessing the binding of various effective concentrations of an antibody of the invention to HPA-1a in the presence of varying concentrations of a test antibody (e.g., a substantially homologous antibody). The amount of inhibition of binding induced by the test antibody can then be assessed. A test antibody that shows increased competition with an antibody of the invention at increasing concentrations (i.e., increasing concentrations of the test antibody result in a corresponding reduction in the amount of antibody of the invention binding to HPA-1a) is evidence of binding to substantially the same epitope. Preferably, the test antibody significantly reduces the amount of antibody of the invention that binds to HPA-1a. Preferably, the test antibody reduces the amount of antibody of the invention that binds to HPA-1a by at least about 95%. ELISA and flow cytometry assays are appropriate for assessing inhibition of binding in such a competition assay but other suitable techniques would be well known to a person skilled in the art.

Substantially homologous sequences of proteins of the invention include, without limitation, conservative amino acid substitutions, or for example alterations that do not affect the VH, VL or CDR domains of the antibodies, e.g., antibodies where tag sequences or other components are added that do not contribute to the binding of antigen, or alterations to convert one type or format of antibody molecule or fragment to another type or format of antibody molecule or fragment (e.g., conversion from Fab to scFv or vice versa), or the conversion of an antibody molecule to a particular class or subclass of antibody molecule (e.g., the conversion of an antibody molecule to IgG or a subclass thereof, e.g., IgG1 or IgG3).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W (Thompson, Higgins, Gibson, *Nucleic Acids Res.,* 22:4673-4680, 1994). If desired, the Clustal W algorithm can be used together with BLOSUM 62 scoring matrix (Henikoff and Henikoff, *Proc. Natl. Acad. Sci. USA,* 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.,* 48:443, 1970) as revised by Smith and Waterman (Smith and Waterman, *Adv. Appl. Math.,* 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.,* 48:1073, 1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, *CABIOS,* 4:11-17, 1988), FASTA (Pearson and Lipman, *Proc. Natl. Acad. Sci. USA,* 85:2444-2448, 1988; Pearson, *Methods in Enzymology,* 183:63-98, 1990) and gapped BLAST (Altschul et al., *Nucleic Acids Res.,* 25:3389-3402, 1997), BLASTP, BLASTN, or GCG (Devereux, Haeberli, Smithies, *Nucleic Acids Res.,* 12:387, 1984) are also useful for this purpose. Furthermore, the Dali server at the European Bioinformatics institute offers structure-based alignments of protein sequences (Holm, *Trends in Biochemical Sciences,* 20:478-480, 1995; Holm, *J. Mol. Biol.,* 233:123-38, 1993; Holm, *Nucleic Acid Res.,* 26:316-9, 1998).

By way of providing a reference point, sequences according to the present invention having 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region or fragment thereof, unless otherwise specifically stated or made clear from the scientific terminology, refer to a range of anti-HPA-1a antibodies as well as to the specific 26.4 antibody.

The terms "antibody" and "immunoglobulin", as used herein, refer broadly to any immunological binding agent that comprises an antigen binding domain (e.g. a human antigen binding domain), including polyclonal and monoclonal antibodies. Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known.

Generally, where whole antibodies rather than antigen binding regions are used in the invention, IgG and/or IgM are preferred because they are the most common antibodies in the physiological situation and because they are most easily made in a laboratory setting. IgG1 and IgG3 antibodies are particularly preferred.

The "light chains" of mammalian antibodies are assigned to one of two clearly distinct types: kappa (κ) and lambda (λ), based on the amino acid sequences of their constant domains and some amino acids in the framework regions of their variable domains.

As will be understood by those in the art, the immunological binding reagents encompassed by the term "antibody" extend to all human antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. In one preferred embodiment the antibody fragment is a F(ab')2 fragment.

The techniques for preparing and using various antibody-based constructs and fragments are well known in the art. Diabodies, in particular, are further described in EP 404 097 and WO 93/11161; whereas linear antibodies are further described in the art.

The term "heavy chain complementarity determining region" ("heavy chain CDR") as used herein refers to regions of hypervariability within the heavy chain variable region ($V_H$ domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs.

The term "heavy chain variable region" ($V_H$ domain) as used herein refers to the variable region of a heavy chain of an antibody molecule.

The term "light chain complementarity determining region" ("light chain CDR") as used herein refers to regions of hypervariability within the light chain variable region ($V_L$ domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs.

The term "light chain variable region" ($V_L$ domain) as used herein refers to the variable region of a light chain of an antibody molecule.

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

In certain embodiments, the antibody or antibody fragment of the present invention comprises all or a portion of a heavy chain constant region, such as an IgG1, IgG2, IgG3, IgG4, IgA1, IgA2, IgE, IgM or IgD constant region. Preferably, the heavy chain constant region is an IgG1 or IgG3 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies.

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the antibody or antibody fragment comprises an antibody light chain variable region ($V_L$) that comprises three CDR domains and an antibody heavy chain variable region ($V_H$) that comprises three CDR domains. Said VL and VH generally form the antigen binding site.

An "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the $V_H$-$V_L$ dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not necessary for antigen binding. Thus, constructs smaller than the above classical antibody fragment are known to be effective.

For example, camelid antibodies have an extensive antigen binding repertoire but are devoid of light chains. Also, results with single domain antibodies comprising VH domains alone or VL domains alone show that these domains can bind to antigen with acceptably high affinities. Thus, three CDRs can effectively bind antigen.

Thus, although preferred antibodies of the invention might comprise six CDR regions (three from a light chain and three from a heavy chain), antibodies with fewer than six CDR regions (e.g. 3 CDR regions) are encompassed by the invention. Antibodies with CDRs from only the heavy chain or light chain are also contemplated.

Preferred light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds HPA-1a can be readily identified by a person skilled in the art.

For example, a heavy chain variable region of the invention can be combined with a single light chain variable region or a repertoire of light chain variable regions and the resulting antibodies tested for binding to HPA-1a.

If desired, similar methods could be used to identify alternative heavy chain variable regions for use in combination with preferred light chain variable regions of the invention.

Thus, another aspect of the invention provides an isolated antibody that specifically binds to HPA-1a and that comprises at least one heavy chain variable region that comprises three CDRs and at least one light chain variable region that comprises three CDRs, wherein said light chain variable region comprises:
    (a) a variable light (VL) CDR1 that has the amino acid sequence of SEQ ID NO:8 or a sequence substantially homologous thereto,
    (b) a VL CDR2 that has the amino acid sequence of SEQ ID NO:9 or a sequence substantially homologous thereto, and
    (c) a VL CDR3 that has the amino acid sequence of SEQ ID NO:10 or a sequence substantially homologous thereto.

Substantially homologous sequences are defined elsewhere herein. In certain embodiments, the substantially homologous sequence is a sequence containing 1, 2 or 3 amino acid substitutions compared to the given CDR sequence, or said substantially homologous sequence is a sequence containing conservative amino acid substitutions of the given CDR sequence. Other features and properties of other aspects of the invention apply, mutatis mutandis, to this aspect of the invention.

In certain embodiments, the antibody comprises a VL domain that comprises the amino acid sequence of SEQ ID NO:4, or a sequence substantially homologous thereto (e.g. a sequence having at least 80% sequence identity thereto). In preferred embodiments, the VL domain comprises the amino acid sequence of SEQ ID NO:4.

In another aspect, the invention provides an isolated antibody that specifically binds to HPA-1a and that comprises at least one heavy chain variable region that comprises three CDRs and at least one light chain variable region that comprises three CDRs, wherein said heavy chain variable region comprises:
    (a) a variable heavy (VH) CDR1 that has the amino acid sequence of SEQ ID NO:5 or a sequence substantially homologous thereto,
    (b) a VH CDR2 that has the amino acid sequence of SEQ ID NO:6 or a sequence substantially homologous thereto, and
    (c) a VH CDR3 that has the amino acid sequence of SEQ ID NO:7 or a sequence substantially homologous thereto.

Substantially homologous sequences are defined elsewhere herein. In certain embodiments, the substantially homologous sequence is a sequence containing 1, 2 or 3 amino acid substitutions compared to the given CDR sequence, or said substantially homologous sequence is a sequence containing conservative amino acid substitutions of the given CDR sequence. Other features and properties of other aspects of the invention apply, mutatis mutandis, to this aspect of the invention.

In certain embodiments, the antibody comprises a VH domain that comprises the amino acid sequence of SEQ ID NO:3, or a sequence substantially homologous thereto (e.g. a sequence having at least 80% sequence identity thereto). In preferred embodiments, the VH domain comprises the amino acid sequence of SEQ ID NO:3.

A yet further aspect of the invention provides an antibody, preferably an isolated antibody, more preferably a human antibody, which specifically binds to HPA-1a and which has the ability to compete with (i.e. bind to the same or substantially the same epitope as) the 26.4 antibody (i.e. an antibody comprising the VL of SEQ ID NO:4 and the VH of SEQ ID NO:3) as described herein, or the ability to compete with an antibody comprising the same CDRs as 26.4, i.e. an antibody comprising VL CDR sequences of SEQ ID NOs: 8, 9 and 10 and VH CDR sequences of SEQ ID NOs: 5, 6 and 7, for binding to HPA-1a. Other features and properties of other aspects of the invention apply, mutatis mutandis, to this aspect of the invention.

Binding to the same epitope/antigen can be readily tested by methods well known and described in the art, e.g. using binding assays such as a competitive inhibition assay. Thus, a person skilled in the art will appreciate that binding assays can be used to identify other antibodies and antibody fragments with the same binding specificities as the antibodies and antibody fragments of the invention. Suitable binding assays are discussed elsewhere herein.

In some embodiments, an antibody of the invention is a Type II anti-HPA-1a antibody. Thus, in some embodiments, an antibody of the present invention binds to an epitope on $\beta_3$ integrin that is not solely defined by the PSI (plexin/semaphorin/integrin) domain of $\beta_3$ integrin. In some embodiments, the epitope on $\beta_3$ integrin to which antibodies of the invention bind includes residues of the PSI (plexin/semaphorin/integrin) domain and, in addition, includes residues of the hybrid and/or of an epidermal growth factor (EGF) domain(s) of $\beta_3$ integrin. In some embodiments, the epitope on $\beta_3$ integrin to which antibodies of the invention bind includes residues of the hybrid and/or of an epidermal growth factor (EGF) domain(s) of $\beta_3$ integrin. A suitable assay for identifying domains on $\beta_3$ integrin which are bound by an antibody is described in Example 4.

Preferably, the above described abilities and properties are observed at a measurable or significant level and more preferably at a statistically significant level, when compared to appropriate control levels. Appropriate significance levels are discussed elsewhere herein. More preferably, one or more of the above described abilities and properties are observed at a level which is measurably better, or more preferably significantly better, when compared to the abilities observed for prior art antibodies.

In any statistical analysis referred to herein, preferably the statistically significant difference over a relevant control has a probability value of <0.1, preferably <0.05, more preferably <0.01. Appropriate methods of determining statistical significance are well known and documented in the art and any of these may be used.

In other preferred embodiments, second generation antibodies are provided that have enhanced or superior properties in comparison to an original anti-HPA-1a antibody, such as 26.4.

Comparisons to identify effective second generation antibodies are readily conducted and quantified, e.g., using one or more of the various assays described in detail herein or in the art. Second generation antibodies that have an enhanced biological property or activity of at least about 2-fold, 5-fold, 10-fold, 20-fold, and preferably, at least about 50-fold, in comparison to the anti-HPA-1a antibodies of the present invention, as exemplified by the 26.4 antibody, are encompassed by the present invention.

The antibody, binding protein and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins or polypeptides, e.g., antibodies, refers to such molecules when isolated from, purified from, or substantially free of their natural environment, e.g., isolated from or purified from the human or animal body (if indeed they occur naturally), or refers to such molecules when produced by a technical process, i.e., includes recombinant and synthetically produced molecules.

Thus, when used in connection with a protein or polypeptide molecule such as light chain CDRs 1, 2 and 3, heavy chain CDRs 1, 2 and 3, light chain variable regions, heavy chain variable regions, and binding proteins or antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

In preferred embodiments the antibodies of the invention are human antibodies, more preferably fully human antibodies.

The term "human" as used herein in connection with antibody molecules and binding proteins first refers to antibodies and binding proteins having variable regions (e.g., $V_H$, $V_L$, CDR or FR regions) and, optionally, constant antibody regions, isolated or derived from a human repertoire or derived from or corresponding to sequences found in humans, e.g., in the human germline or somatic cells. The 26.4 antibody is an example of such a human antibody molecule wherein the variable regions correspond to sequences found in a human.

The term "fragment" as used herein refers to fragments of biological relevance, e.g., fragments that contribute to antigen binding, e.g., form part of the antigen binding site, and/or contribute to the inhibition or reduction in function of the HPA-1a antigen. Certain preferred fragments comprise a heavy chain variable region ($V_H$ domain) and/or a light chain variable region ($V_L$ domain) of the antibodies of the invention.

A person skilled in the art will appreciate that the proteins and polypeptides of the invention, such as the light and heavy CDRs, the light and heavy chain variable regions, antibodies, antibody fragments, and immunoconjugates, may be prepared in any of several ways well known and described in the art, but are most preferably prepared using recombinant methods.

Nucleic acid fragments encoding the light and heavy chain variable regions of the antibodies of the invention can be derived or produced by any appropriate method, e.g., by cloning or synthesis.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g., Fab fragments, scFv fragments, etc. Typically, or as part of this further manipulation procedure, the nucleic acid fragments encoding the antibody molecules of the invention are generally incorporated into an appropriate expression vector in order to facilitate production of the antibodies of the invention.

Possible expression vectors include but are not limited to cosmids, plasmids, or modified viruses (e.g., replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes and are well known in the art. Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags).

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. Suitable methods for transforming and transfecting host cells can be found in Sambrook et al., 1989 (Sambrook, Fritsch and Maniatis, *Molecular Cloning: A Laboratory Manual,* 2nd Ed., Cold Spring Harbor Press, Cold Spring Harbor, N.Y., 1989) and other laboratory textbooks.

Suitable host cells include a wide variety of eukaryotic host cells and prokaryotic cells. For example, the proteins of the invention may be expressed in yeast cells or mammalian cells. HEK 293E cells are particularly preferred. In addition, the proteins of the invention may be expressed in prokaryotic cells, such as *Escherichia coli.*

Given the teachings provided herein, promoters, terminators, and methods for introducing expression vectors of an appropriate type into plant, avian, and insect cells may also be readily accomplished.

Alternatively, the proteins of the invention may also be expressed in non-human transgenic animals such as, rats, rabbits, sheep and pigs.

The proteins of the invention may also be prepared by chemical synthesis using techniques well known in the chemistry of proteins such as solid phase synthesis.

N-terminal or C-terminal fusion proteins comprising the antibodies and proteins of the invention conjugated to other molecules, such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate.

A yet further aspect provides an expression construct or expression vector comprising one or more of the nucleic acid fragments or segments or molecules of the invention. Preferably the expression constructs or vectors are recombinant. Preferably said constructs or vectors further comprise the necessary regulatory sequences for the transcription and translation of the protein sequence encoded by the nucleic acid molecule of the invention.

A yet further aspect provides a host cell or virus comprising one or more expression constructs or expression vectors of the invention. Also provided are host cells or viruses comprising one or more of the nucleic acid molecules of the invention. A host cell or virus expressing an antibody of the invention forms a yet further aspect. Suitable host cells include, but are not limited to HEK293E cells.

A yet further aspect of the invention provides a method of producing an antibody of the present invention comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the encoded antibody or protein; and optionally (ii) isolating or obtaining the antibody or protein from the host cell or from the growth medium/supernatant. Such methods of production may also comprise a step of purification of the antibody or protein product and/or formulating the antibody or product into a composition including at least one additional component, such as a pharmaceutically acceptable carrier or excipient.

In embodiments when the antibody or protein of the invention is made up of more than one polypeptide chain (e.g., certain fragments such as Fab fragments), then all the polypeptides are preferably expressed in the host cell, either from the same or a different expression vector, so that the complete proteins, e.g., binding proteins of the invention, can assemble in the host cell and be isolated or purified therefrom.

In another aspect, the invention provides a method of binding HPA-1a, comprising contacting a composition comprising HPA-1a with an antibody of the invention, or an immunoconjugate thereof.

In yet another aspect, the invention provides a method of detecting HPA-1a, comprising contacting a composition suspected of containing HPA-1a with the antibody of the invention, or an immunoconjugate thereof, under conditions effective to allow the formation of HPA-1a/antibody complexes and detecting the complexes so formed.

The antibodies of the invention may also be used to produce further antibodies that bind to HPA-1a. Such uses involve for example the addition, deletion, substitution or insertion of one or more amino acids in the amino acid sequence of a parent antibody to form a new antibody, wherein said parent antibody is one of the antibodies of the invention as defined elsewhere herein, and testing the resulting new antibody to identify antibodies that bind to HPA-1a. Such methods can be used to form multiple new antibodies that can all be tested for their ability to bind HPA-1a. Preferably said addition, deletion, substitution or insertion of one or more amino acids takes place in one or more of the CDR domains.

Such modification or mutation to a parent antibody can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g., the Ab-Ag complex, to identify the key residues involved in the antigen binding. Subsequently, those residues can be mutated to enhance the interaction. Alternatively, one or more amino acid residues can simply be targeted for directed mutagenesis and the effect on binding to HPA-1a assessed.

Random mutagenesis can be carried out in any appropriate way, e.g., by error-prone PCR, chain shuffling or mutator *E. coli* strains.

Thus, one or more of the $V_H$ domains of the invention can be combined with a single $V_L$ domain or a repertoire of $V_L$ domains from any appropriate source and the resulting new antibodies tested to identify antibodies specific for HPA-1a. Conversely, one or more of the $V_L$ domains of the invention can be combined with a single $V_H$ domain or repertoire of $V_H$ domains from any appropriate source and the resulting new antibodies tested to identify antibodies that bind to HPA-1a.

Similarly, one or more, or preferably all three CDRs of the $V_H$ and/or $V_L$ domains of the invention can be grafted into a single $V_H$ and/or $V_L$ domain or a repertoire of $V_H$ and/or $V_L$ domains, as appropriate, and the resulting new antibodies tested to identify antibodies that bind to HPA-1a.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate binding proteins and domains thereof are modified such that the amino acid sequence of the resulting expressed protein is in turn modified in the appropriate way.

The new antibodies produced by these methods will preferably have improved functional properties, e.g. a higher or enhanced affinity (or at least an equivalent affinity) for HPA-1a as the parent antibodies, and can be treated and used in the same way as the antibodies of the invention as described elsewhere herein (e.g., for therapy, diagnosis, in compositions etc.). Alternatively, or additionally, the new antibodies will have one or more other improved functional properties as described elsewhere herein.

New antibodies produced, obtained or obtainable by these methods form a yet further aspect of the invention.

Testing the ability of one or more antibodies to bind to HPA-1a can be carried out by any appropriate method, which are well known and described in the art. Suitable methods are also described in the Examples section.

The invention also provides a hybridoma secreting the 26.4 antibody (e.g. the hybridoma DL18BL26.4H described in the Example section). In certain embodiments, the invention provides an antibody secreted by such a hybridoma (or an antibody which competes with such an antibody for binding to HPA-1a).

The invention also provides a range of conjugated antibodies and fragments thereof in which the anti-HPA-1a antibody is operatively attached to at least one other therapeutic or diagnostic agent. The term "immunoconjugate" is broadly used to define the operative association of the antibody with another effective agent and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

The invention also provides an antibody as defined herein coupled to a solid support (e.g. a microsphere).

Formulations (compositions) comprising one or more antibodies of the invention in admixture with a suitable diluent, carrier or excipient constitute a further aspect of the present invention. Such formulations may be for pharmaceutical use. Suitable diluents, excipients and carriers are known to the skilled man.

The compositions according to the invention may be presented, for example, in a form suitable for oral, nasal, parenteral, intravenal, topical or rectal administration.

The active compounds defined herein may be presented in the conventional pharmacological forms of administration, such as tablets, coated tablets, nasal sprays, solutions, emulsions, liposomes, powders, capsules or sustained release forms. Conventional pharmaceutical excipients as well as the usual methods of production may be employed for the preparation of these forms.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers, either with an aerosol propellant or provided with means for manual compression.

The pharmaceutical compositions (formulations) of the present invention are preferably administered parenterally. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the peptide in the form of a nasal or pulmonal spray. As a still further option, the antibodies of the invention can also be administered transdermally, e.g. from a patch, optionally an iontophoretic patch, or transmucosally, e.g. bucally.

Dosage units containing the antibodies preferably contain 0.1-10 mg, for example 1-5 mg of the active agent. Other useful doses include, but are not limited to, doses which achieve a plasma concentration of 0.1 to 1 IU/ml, for example 0.5 IU/mL (0.08 µg/mL). Such a dose of 0.5 IU/mL (0.08 µg/mL) may be achieved by intravenous administration of 2,000 IU.

The pharmaceutical compositions may additionally comprise further active ingredients as described above in the context of co-administration regimens.

A further aspect of the present invention provides the anti-HPA-1a antibodies defined herein for use in therapy, in particular for use in the treatment or prophylaxis of FNAIT. Thus, therapy includes prophylactic treatment.

HPA-1a negative (i.e. HPA-1bb) women may produce anti-HPA-1a antibodies as a result of immunization with HPA-1a in connection with a non-compatible pregnancy (i.e. a pregnancy with a HPA-1a positive fetus). Such maternally produced anti-HPA-1a antibodies traverse the placenta, bind fetal platelets and may accelerate platelet destruction, thereby causing FNAIT.

Without wishing to be bound by theory, it is believed that the antibodies of the present invention administered to such an alloimmunized woman cross the placenta and compete with maternal HPA-1a antibodies for binding to the fetal platelets, thereby reducing platelet destruction and thus treating FNAIT.

In the context of FNAIT treatment, preferably the antibody has a reduced or abolished effector function. For example, the Fc portion of an immunoglobulin (Ig) can be modified (or removed) in order to reduce/remove the effector function. Methods for doing so are known in the art. Preferably, in the context of FNAIT treatment, the antibody has an Fc portion which favours placental transfer and which has mutations which diminish (or abolish) its platelet destructive properties (e.g. as discussed in Mathiesen et al., Blood (2013) 122(7):1174-81).

In the context of FNAIT treatment, certain preferred subjects for administration with an antibody of the invention are those known to be carrying a fetus that is already suffering from FNAIT, as determined by, for example a platelet count in the fetus.

The antibodies of the present invention may also be used to prevent FNAIT, i.e. may be used in prophylactic treatments. In certain embodiments of such prophylactic treatments, the antibodies of the invention may be administered to a woman who is already pregnant, preferably to a pregnant woman known to be HPA-1a negative, more preferably a woman already pregnant with an incompatible pregnancy (i.e. the mother is HPA-1a negative and the fetus is HPA-1a positive).

It has been found that alloimmunization with HPA-1a can also occur in connection with delivery of a non-compatible fetus (baby). HPA-1a stimulation at delivery can be the first HPA-1a stimulus that the mother has received (i.e. there may have been no alloimmunization during pregnancy). Thus, in certain embodiments, antibodies of the invention are administered to mother at delivery or shortly after delivery, preferably within 72 hours of delivery.

Without wishing to be bound by theory, anti-HPA-1a antibodies of the present invention administered to a mother in connection with delivery (or otherwise at risk of alloimmunization) would bind to HPA-1a on HPA-1a positive fetal (baby's) platelets entering the maternal circulation and destroy the HPA-1a positive platelets thereby preventing stimulation of the mother's immune system by the fetus'/baby's HPA-1a bearing platelets. Accordingly, alloimmunization is prevented, and FNAIT does not occur. An analogous mechanism prevents alloimmunization in connection with fetal trophoblasts or other trophoblast material entering the maternal circulation.

As described above, in some embodiments the anti-HPA-1a antibodies of the present invention have the ability to inhibit the binding of the anti-HPA-1a antibody SZ21 to αVβ3 integrin. Without wishing to be bound by theory, the ability of an antibody of the invention to stably bind to αVβ3 integrin and to be able to inhibit the binding of other anti-HPA-1a antibodies to αVβ3 integrin indicates that such antibodies would have utility in the prevention of alloimmunization in connection with fetal trophoblasts or other trophoblast material entering the maternal circulation.

In the case where alloimmunization in connection with delivery is prevented, a subsequent non-compatible pregnancy can be protected from FNAIT.

Thus, in a further aspect, the invention also provides the anti-HPA-1a antibodies defined herein for use in preventing alloimmunization with HPA-1a in a subject.

Ghevaert et al. (*Blood,* 122: 313-320 (2013)) discusses the use of an anti-HPA-1a antibody in the treatment and prophylaxis of FNAIT.

In some embodiments, particularly in the context of FNAIT prophylaxis, anti-HPA-1a IgG antibodies are preferably glycosylated. In some embodiments, particularly in the context of FNAIT prophylaxis, anti-HPA-1a IgG antibodies are preferably not fucosylated (i.e. preferably not modified with a fucose group).

Antibodies of the present invention bind specifically to HPA-1a (i.e. do not cross-react with the alloantigen HPA-1b). Thus, the antibodies of the invention can be used to determine whether a subject (preferably a female subject) is HPA-1a positive or HPA-1a negative.

Accordingly, in a further aspect, the invention provides a method for analysing for the presence or absence of HPA-1a in a sample (preferably a sample containing platelets) that has been obtained from a subject, said method comprising the steps of (a) contacting said sample with an antibody of the invention which binds specifically to HPA-1a; and
(b) analysing for the presence or absence of anti-HPA-1a antibody-HPA-1a (antigen) complexes.

The presence of anti-HPA-1a antibody-HPA-1a (antigen) complexes indicates the presence of HPA-1a in the sample. The absence of anti-HPA-1a antibody-HPA-1a (antigen) complexes indicates the absence of HPA-1a in the sample. Thus, the present invention provides a method for HPA-1 phenotyping. Suitable methods for analysing for (i.e. determining) for the presence of HPA-1a antibody-HPA-1a (antigen) complexes are known in the art. In one embodiment, whole blood flow cytometry is used, preferably in such embodiments an antibody of the invention (e.g. an $IgG_1$ form thereof) is conjugated to a fluorescent dye. In some embodiments the whole blood is peripheral blood, preferably obtained from subjects no more than 10 days before it is used. In some embodiments whole blood cytometry is used in accordance with the experimental examples herein.

A method for analysing for the presence or absence of HPA-1a in a sample as described above can be used to identify women who might benefit from the prophylactic treatments described herein.

Several prospective studies found that high levels of maternal anti-HPA-1a antibodies correlate with low platelet count in the newborn. Thus, quantitation of anti-HPA-1a antibodies can be used as predictive factor of the degree of thrombocytopenia in the newborn. Currently used reference material for anti-HPA-1a antibody quantitation was prepared by the National Institute of Biological Standards and Control (NIBSC). This NIBSC standard contains plasma from six HPA-1a immunized donors and its supply is dependent on the availability of such donors. Replacing polyclonal sera with a recombinant antibody would provide a relatively cheap, standardized, highly specific and unlimited source of anti-HPA-1a antibody to be used as a control reference reagent.

Thus, in a further aspect, the present invention provides the use of an antibody of the present invention as a reference standard for quantifying anti-HPA-1a antibodies (maternally produced) in a sample (e.g. a whole blood or plasma sample). Preferably said reference standard is used in a MAIPA (monoclonal antibody immobilization of platelet antigens) assay to quantify anti-HPA-1a antibodies in a sample.

Alternatively viewed the present invention provides a method of treating or preventing FNAIT which method comprises administering to a patient in need thereof a therapeutically or prophylactically effective amount of an antibody of the invention as defined herein.

A therapeutically or prophylactically effective amount will be determined based on the clinical assessment and can be readily monitored.

Further alternatively viewed, the present invention provides the use of an antibody of the invention as defined herein in the manufacture of a medicament for treating or preventing FNAIT.

Subjects treated in accordance with the present invention will preferably be humans, more preferably female humans (e.g. pregnant female subjects).

The compositions and methods and uses of the present invention may be used in combination with other therapeutics and diagnostics. In terms of biological agents, preferably diagnostic or therapeutic agents, for use "in combination" with an anti-HPA-1a antibody in accordance with the present invention, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where the anti-HPA-1a of the invention is a naked antibody and is used in combination with an agent or therapeutic agent that is not operatively attached thereto. In other "combined" embodiments of the invention, the anti-HPA-1a antibody of the invention is an immunoconjugate wherein the antibody is itself operatively associated or combined with the agent or therapeutic agent. The operative attachment includes all forms of direct and indirect attachment as described herein and known in the art.

The invention further includes kits comprising one or more of the antibodies, immunoconjugates or compositions of the invention or one or more of the nucleic acid molecules encoding the antibodies of the invention, or one or more recombinant expression vectors comprising the nucleic acid sequences of the invention, or one or more host cells or viruses comprising the recombinant expression vectors or nucleic acid sequences of the invention. Preferably said kits are for use in the methods and uses as described herein, e.g., the therapeutic, diagnostic or imaging methods as described herein, or are for use in the in vitro assays or methods as described herein. The antibody in such kits may preferably be an antibody conjugate as described elsewhere herein, e.g., may be conjugated to a detectable moiety or may be an immumoconjugate. Preferably said kits comprise instructions for use of the kit components, for example in diagnosis. Preferably said kits are for diagnosing or treating diseases as described elsewhere herein, and optionally comprise instructions for use of the kit components to diagnose or treat such diseases.

The antibodies of the invention as defined herein may also be used as molecular tools for in vitro or in vivo applications and assays. As the antibodies have an antigen binding site, these can function as members of specific binding pairs and these molecules can be used in any assay where the particular binding pair member is required.

Thus, yet further aspects of the invention provide a reagent that comprises an antibody of the invention as defined herein and the use of such antibodies as molecular tools, for example in in vitro or in vivo assays.

Table of Nucleotide and Amino Acid Sequences Disclosed Herein and their Sequence Identifiers (SEQ ID NOs)

All nucleotide sequences are recited herein 5' to 3' in line with convention in this technical field.

TABLE 1

| SEQ ID NO: | Description | Sequence |
|---|---|---|
| | | 26.4 antibody |
| 1 | VH domain (nt) | caggtacagttgcagcagtcaggtccaggactggtgaagccctcg cagaccctgtcactcacctgtgccatctccggggacagtgtcagca gcaacagtgctgcttggaactggatcaggcagtccccatcgagag gccttgagtggctgggaaggacatacttcaggtccaactggtacaa tgattatgcagcatctgtgaaaagtcgaataaccatcaaccaagac acatccaagaaccagctctccctgcagctgaactctgtgactcccg aggacacggctatgtattactgtgcaagagatggggcctggggtg gcagcagctggtggccaggccttcctcaccactactactctggtatg gacgtctggggccaggggaccacggtcaccgtctcctca |
| 2 | VL domain (nt) | gaaattgtgttgacacagtctccagccaccctgtcattgtctccagg ggaaagagccaccctctcctgcagggccagtcagagtgttagca gctacttagcctggtaccaacagaagcctggccaggctcccaggc tcctcatctatgatgcatccaaaagggccactggcatcccagccag gttcagtggcagtgggtctgggacagacttcagtctcaccatcaga agcctcgagcctgaagattttgcagtttattactgtcaacagcgtagc gactggcagggactcactttcggcggagggaccaaggtggagat caaa |
| 3 | VH domain (aa) | QVQLQQSGPGLVKPSQTLSLTCAISGDSVSSNS AAWNWIRQSPSRGLEWLGRTYFRSNWYNDYA ASVKSRITINQDTSKNQLSLQLNSVTPEDTAMYY CARDGAWGGSWWPGLPHHYYSGMDVWGQ GTTVTVSS |
| 4 | VL domain (aa) | EIVLTQSPATLSLSPGERATLSCRASQSVSSYLA WYQQKPGQAPRLLIYDASKRATGIPARFSGSGS GTDFSLTIRSLEPEDFAVYYCQQRSDWQGLT FGGGTKVEIK |
| 5 | Heavy CDR1 | GDSVSSNSAA |
| 6 | Heavy CDR2 | TYFRSNWYN |
| 7 | Heavy CDR3 | ARDGAWGGSWWPGLPHHYYSGMDV |
| 8 | Light CDR1 | QSVSSY |
| 9 | Light CDR2 | DAS |
| 10 | Light CDR3 | QQRSDWQGLT |
| 11 | Heavy FR1 | QVQLQQSGPGLVKPSQTLSLTCAIS |

TABLE 1-continued

| SEQ ID NO: | Description | Sequence |
|---|---|---|
| 12 | Heavy FR2 | WNWIRQSPSRGLEWLGR |
| 13 | Heavy FR3 | DYAASVKSRITINQDTSKNQLSLQLNSVTPEDTAMYYC |
| 14 | Heavy FR4 | WGQGTTVTVSS |
| 15 | Light FR1 | EIVLTQSPATLSLSPGERATLSCRAS |
| 16 | Light FR2 | LAWYQQKPGQAPRLLIY |
| 17 | Light FR3 | KRATGIPARFSGSGSGTDFSLTIRSLEPEDFAVYYC |
| 18 | Light FR4 | FGGGTKVEIK |
| 19 | IgG1 heavy chain (nt) | CAGGTGCAGCTGCAGCAGTCCGGCCCTGGGCTGGTGAAGCCTAGCCAGACCCTGTCCCTGACATGCGCCATCTCAGGCGACAGCGTGAGCTCCAACTCTGCCGCTTGGAATTGGATTAGACAGAGCCCATCCCGCGGGCTGGAGTGGCTGGGACGGACCTACTTCAGAAGCAACTGGTACAATGACTATGCCGCTTCCGTGAAGTCTCGGATCACCATTAACCAGGATACATCTAAAAATCAGCTGAGTCTGCAGCTGAACTCAGTGACTCCCGAAGACACCGCCATGTACTATTGTGCTAGGGATGGCGCTTGGGGCGGGTCTAGTTGGTGGCCAGGACTGCCCCACCATTACTATAGCGGCATGGACGTGTGGGGACAGGGCACCACAGTGACAGTGTCAAGCGCCAGCACTAAGGGCCCTTCCGTGTTTCCTCTGGCTCCATCCTCTAAATCTACAAGTGGAGGCACTGCCGCTCTGGGGTGTCTGGTGAAGGATTATTTCCCTGAGCCAGTGACTGTGAGTTGGAACTCAGGCGCCCTGACTAGCGGGGTGCACACCTTTCCCGCTGTGCTGCAGAGTTCAGGGCTGTACAGCCTGAGCTCCGTGGTGACCGTGCCTTCTAGTTCACTGGGAACTCAGACCTATATCTGCAACGTGAATCACAAGCCTTCTAATACAAAAGTGGACAAGAAAGTGGAGCCAAAGAGTTGTGATAAAACACATACTTGCCCTCCCTGCCCTGCCCCTGAACTGCTGGGCGGCCCAAGCGTGTTCCTGTTTCCACCCAAGCCCAAAGATACACTGATGATTAGCCGGACTCCGGAGGTCACATGCGTGGTGGTGGACGTGAGCCACGAGGATCCTGAAGTGAAGTTCAACTGGTACGTGGACGGCGTGGAAGTGCATAATGCCAAGACCAAACCACGGGAGGAACAGTACAACTCTACATATAGAGTGGTGAGTGTGCTGACTGTGCTGCACCAGGATTGGCTGAACGGGAAAGAGTATAAGTGCAAAGTGAGCAATAAGGCCCTGCCTGCTCCAATCGAGAAAACCATTTCCAAGGCCAAAGGACAGCCCAGGGAACCTCAGGTGTACACACTGCCCCCTAGTCGCGACGAGCTGACTAAGAACCAGGTGTCTCTGACCTGTCTGGTGAAAGGCTTCTATCCATCCGATATCGCTGTGGAGTGGGAATCTAATGGGCAGCCCGAAAACAATTACAAGACCACACCACCCGTGCTGGACAGCGATGGATCCTTCTTTCTGTATTCAAAGCTGACTGTGGACAAAAGCCGGTGGCAGCAGGGCAACGTGTTTAGCTGTTCCGTGATGCATGAGGCTCTGCACAATCATTACACCCAGAAGTCTCTGAGTCTGTCACCCGGGAAATGA |
| 20 | IgG1 light chain (kappa) (nt) | GAGATCGTGCTGACTCAGTCTCCAGCCACCCTGTCCCTGTCTCCAGGAGAACGGGCCACTCTGTCTTGCAGAGCTAGTCAGTCAGTGAGCTCCTACCTGGCCTGGTATCAGCAGAAGCCAGGACAGGCTCCCCGGCTGCTGATCTACGACGCCTCCAAAAGGGCTACAGGCATTCCCGCTCGCTTCAGCGGCTCCGGGTCTGGAACAGATTTTTCCCTGACTATCAGAAGCCTGGAGCCTGAAGACTTCGCCGTGTACTATTGCCAGCAGAGATCTGATTGGCAGGGGCTGACCTTTGGCGGGGGAACAAAGGTGGAGATCAAAAGGACCGTGGCCGCTCCAAGCGTGTTCATCTTTCCCCCTAGCGACGAACAGCTGAAGTCAGGGACAGCCAGCGTGGTGTGCCTGCTGAACAATTTCTACCCCCGCGAGGCCAAGGTGCAGTGGAAAGTGGATAACGCTCTGCA |

TABLE 1-continued

| SEQ ID NO: | Description | Sequence |
|---|---|---|
| | | GAGTGGAAATTCACAGGAGAGCGTGACTGAA CAGGACTCCAAGGATTCTACCTATAGTCTGTC TAGTACCCTGACACTGAGCAAAGCCGACTAC GAGAAGCACAAAGTGTATGCTTGCGAAGTGA CACATCAGGGCCTGTCAAGCCCTGTGACTAA GAGCTTCAACCGGGGCGAGTGTTGA |
| 21 | IgG1 heavy chain (aa) | QVQLQQSGPGLVKPSQTLSLTCAISGDSVSSNS AAWNWIRQSPSRGLEWLGRTYFRSNWYNDYA ASVKSRITINQDTSKNQLSLQLNSVTPEDTAMYY CARDGAWGGSSWWPGLPHHYYSGMDVWGQ GTTVTVSSASTKGPSVFPLAPSSKSTSGGTAAL GCLVKDYFPEPVTVSWNSGALTSGVHTFPAVL QSSGLYSLSSVVTVPSSSLGTQTYICNVNHKPS NTKVDKKVEPKSCDKTHTCPPCPAPELLGGPSV FLFPPKPKDTLMISRTPEVTCVVVDVSHEDPEVK FNWYVDGVEVHNAKTKPREEQYNSTYRVVSVL TVLHQDWLNGKEYKCKVSNKALPAPIEKTISKAK GQPREPQVYTLPPSRDELTKNQVSLTCLVKGFY PSDIAVEWESNGQPENNYKTTPPVLDSDGSFFL YSKLTVDKSRWQQGNVFSCSVMHEALHNHYTQ KSLSLSPGK |
| 22 | IgG1 light chain (kappa) (aa) | EIVLTQSPATLSLSPGERATLSCRASQSVSSYLA WYQQKPGQAPRLLIYDASKRATGIPARFSGSGS GTDFSLTIRSLEPEDFAVYYCQQRSDWQGLTFG GGTKVEIKRTVAAPSVFIFPPSDEQLKSGTASVV CLLNNFYPREAKVQWKVDNALQSGNSQESVTE QDSKDSTYSLSSTLTLSKADYEKHKVYACEVTH QGLSSPVTKSFNRGEC |
| 23 | IgG3 heavy chain (nt) | CAGGTGCAGCTGCAGCAGTCCGGGCCAGGA CTGGTGAAACCCTCACAGACACTGAGCCTGA CTTGTGCCATCAGTGGCGATTCAGTGAGCTC CAACAGCGCCGCTTGGAATTGGATTAGGCAG AGTCCTTCACGCGGACTGGAATGGCTGGGCC GGACCTACTTCAGATCCAACTGGTACAATGAC TATGCCGCCAGCGTGAAGTCCCGGATCACAA TTAACCAGGATACTTCCAAAAATCAGCTGTCT CTGCAGCTGAACAGTGTGACCCCAGAGGACA CAGCCATGTACTATTGCGCCAGAGATGGGGC TTGGGGCGGGTCTAGTTGGTGGCCAGGCCTG CCCCACCATTACTATAGCGGGATGGACGTGT GGGGACAGGGAACCACAGTGACCGTGAGCA GCGCCTCAACCAAAGGGCCTAGCGTGTTTCC TCTGGCTCCATGCAGCAGGTCCACTTCTGGA GGCACCGCCGCTCTGGGATGTCTGGTGAAGG ACTATTTCCCCGAACCTGTGACCGTGTCTTGG AACAGTGGGGCCCTGACCTCTGGAGTGCACA CATTTCCCGCTGTGCTGCAGTCCTCTGGACTG TACAGCCTGAGTTCAGTGGTGACCGTGCCAA GCTCCTCTCTGGGCACACAGACTTATACCTGT AACGTGAATCACAAGCCCAGCAATACAAAGGT GGACAAACGGGTGGAGCTGAAAACACCTCTG GGCGATACTACCCATACTTGCCCACGGTGTC CAGAGCCCAAAAGCTGTGACACCCCTCCCCC ATGCCCAAGATGTCCTGAACCAAAATCTTGTG ATACACCCCTCCATGCCCTAGGTGTCCCGA GCCTAAGAGTTGTGACACTCCCCCTCCATGTC CTAGATGTCCTGCTCCGGAACTGCTGGGCGG TCCGAGCGTGTTTCTGTTCCCGCCGAAACCG AAAGATACCCTGATGATTAGTCGCACGCCGG AAGTTACCTGCGTGGTTGTGGATGTGAGCCAT GAAGACCCGGAAGTTCAGTTTAAATGGTATGT GGATGGTGTTGAAGTGCACAACGCAAAAACC AAACCGCGTGAAGAACAGTACAATAGCACGTT CCGCGTTGTGTCTGTTCTGACCGTGCTGCATC AGGATTGGCTGAACGGCAAAGAATACAAATGT AAAGTTTCTAACAAAGCACTGCCGGCGCCGAT TGAAAAAACGATCAGTAAAACCAAGGGTCAGC CGCGTGAACCGCAGGTGTACACCCTGCCGCC GAGCCGTGAAGAAATGACGAAAAACCAAGTTA GTCTGACCTGCCTGGTGAAAGGCTTTTACCC GAGCGATATTGCAGTGGAATGGGAAAGCTCT GGTCAGCCGGAAAACAATTATAATACCACGCC GCCGATGCTGGATAGTGATGGCAGCTTTTTCC TGTATAGTAAACTGACCGTTGATAAAAGCCGT |

TABLE 1-continued

| SEQ ID NO: | Description | Sequence |
|---|---|---|
| | | TGGCAGCAGGGTAACATCTTTAGTTGCAGCGT GATGCATGAAGCGCTGCACAATCGCTTCACC CAGAAATCTCTGAGTCTGAGCCCGGGCAAAG GTAAATAA |
| 24 | IgG3 light chain (kappa) (nt) | GAGATCGTGCTGACTCAGTCTCCAGCCACCC TGTCCCTGTCTCCAGGAGAACGGGCCACTCT GTCTTGCAGAGCTAGTCAGTCAGTGAGCTCCT ACCTGGCCTGGTATCAGCAGAAGCCAGGACA GGCTCCCCGGCTGCTGATCTACGACGCCTCC AAAAGGGCTACAGGCATTCCCGCTCGCTTCA GCGGCTCCGGGTCTGGAACAGATTTTTCCCT GACTATCAGAAGCCTGGAGCCTGAAGACTTC GCCGTGTACTATTGCCAGCAGAGATCTGATTG GCAGGGGCTGACCTTTGGCGGGGGAACAAA GGTGGAGATCAAAAGGACCGTGGCCGCTCCA AGCGTGTTCATCTTTCCCCCTAGCGACGAACA GCTGAAGTCAGGGACAGCCAGCGTGGTGTGC CTGCTGAACAATTTCTACCCCCGCGAGGCCA AGGTGCAGTGGAAAGTGGATAACGCTCTGCA GAGTGGAAATTCACAGGAGAGCGTGACTGAA CAGGACTCCAAGGATTCTACCTATAGTCTGTC TAGTACCCTGACACTGAGCAAAGCCGACTAC GAGAAGCACAAAGTGTATGCTTGCGAAGTGA CACATCAGGGCCTGTCAAGCCCTGTGACTAA GAGCTTCAACCGGGGCGAGTGTTGA |
| 25 | IgG3 heavy chain (aa) | QVQLQQSGPGLVKPSQTLSLTCAISGDSVSSNS AAWNWIRQSPSRGLEWLGRTYFRSNWYNDYA ASVKSRITINQDTSKNQLSLQLNSVTPEDTAMYY CARDGAWGGSSWWPGLPHHYYSGMDVWGQ GTTVTVSSASTKGPSVFPLAPCSRSTSGGTAAL GCLVKDYFPEPVTVSWNSGALTSGVHTFPAVL QSSGLYSLSSVVTVPSSSLGTQTYTCNVNHKPS NTKVDKRVELKTPLGDTTHTCPRCPEPKSCDTP PPCPRCPEPKSCDTPPPCPRCPEPKSCDTPPP CPRCPAPELLGGPSVFLFPPKPKDTLMISRTPEV TCVVVDVSHEDPEVQFKWYVDGVEVHNAKTKP REEQYNSTFRVVSVLTVLHQDWLNGKEYKCKV SNKALPAPIEKTISKTKGQPREPQVYTLPPSREE MTKNQVSLTCLVKGFYPSDIAVEWESSGQPEN NYNTTPPMLDSDGSFFLYSKLTVDKSRWQQGNI FSCSVMHEALHNRFTQKSLSLSPGKGK |
| 26 | IgG3 light chain (kappa) (aa) | EIVLTQSPATLSLSPGERATLSCRASQSVSSYLA WYQQKPGQAPRLLIYDASKRATGIPARFSGSGS GTDFSLTIRSLEPEDFAVYYCQQRSDWQLTFG GGTKVEIKRTVAAPSVFIFPPSDEQLKSGTASVV CLLNNFYPREAKVQWKVDNALQSGNSQESVTE QDSKDSTYSLSSTLTLSKADYEKHKVYACEVTH QGLSSPVTKSFNRGEC |

The IgG nucleic acid sequences set forth in the above Table are optimised for expression in HEK cells.

The invention will now be further described in the following non-limiting Examples with reference to the following drawings:

BRIEF DESCRIPTION OF THE DRAWINGS

FIG. 1A illustrates cell positive for CD22 were isolated by MACS from PBMCs of an HPA-1a alloimmunized woman and labelled with FITC-conjugated anti-human IgM, IgA and IgD antibodies. The CD22$^+$IgM$^-$IgD$^-$IgA$^-$ population (gated, 5.6% of CD22$^+$ B cells), the IgG$^+$ memory B cells, was identified and isolated by FACS. FIG. 1B illustrates HPA-1a-positive platelets were labelled with CFSE, incubated with B-lymphoblasts from the B-lymphoblast culture secreting anti-HPA-1a antibodies, and platelet-bound B-lymphoblasts (gated, 2% of CD45$^+$ B-lymphoblasts) were isolated individually by FACS into 96 well U-bottom micro plates. Results are representative of at least three independent experiments.

FIG. 2A shows a binding of 26.4 to HPA-1aa and HPA-1bb platelets analysed by flow cytometry. Platelets were incubated with 26.4 cell culture supernatant or medium as a negative control. FITC-conjugated anti-human IgG was used to detect platelet-bound IgG. The results are presented as an overlay of histograms: relative number of cells plotted against the fluorescence intensity. FIG. 2B illustrates the 26.4 was tested against HPA-1aa and HPA-1bb platelets in MAIPA assay. Normal serum was used as a negative control. Samples were run in duplicates. Presented are average absorbance values after background subtraction. Results are representative of at least three independent experiments. B-lymphoblast and hybridoma derived 26.4, and recombinant 26.4 IgG1 and IgG3 performed alike.

FIG. 3. Nucleotide and amino acid sequence of mAb 26.4. Heavy and Light chain V-regions compared with the most homologous germline sequences. Analyzed by IMGT/V-QUEST.

FIG. 5C shows a relative binding response of 26.4 and B2G1 to HPA-1a on αIIbβ3 and αVβ3. Binding response (RU) at the end of association period was calculated relative to 26.4 (26.4 RU were taken as 100% for each integrin). Data presented are average RU generated by injection of three different concentrations of mAbs (20 µg/ml, 10 µg/ml and 5 µg/ml). FIG. 5D shows a percentage of 26.4 and B2G1 bound to HPA-1a on αIIbβ3 and αVβ3 at the end of the dissociation period. The percentage of antibody bound at the end of the dissociation phase was calculated by dividing the RU at the end of dissociation period by the RU at the end of association period multiplied by 100%. Data presented are average percentage calculated from three different concentrations for each mAb.

Figure 5A:
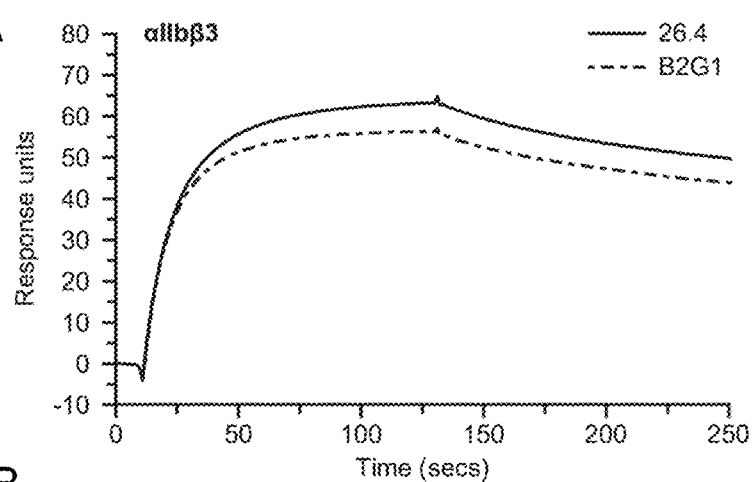
FIGS. 5A-5F. SPR analysis of mAb binding to HPA-1a on αIIbβ3 and αVβ3. Sensograms generated by binding of 26.4 IgG1 (black line) and B2G1 (dashed) to HPA-1a on αIIbβ3 as shown in FIG. 5A and αVβ3 as shown in FIG. 5B immobilized to the sensor chip surface. MAb samples were used in three different concentrations (20 µg/ml, 10 µg/ml and 5 µg/ml); the highest concentration is shown. Results are representative of the two independent experiments.
Figure 5B:
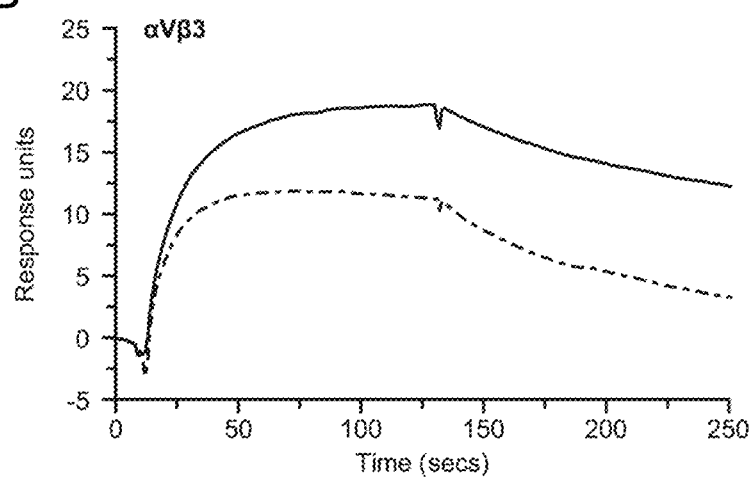
Figure 5C:
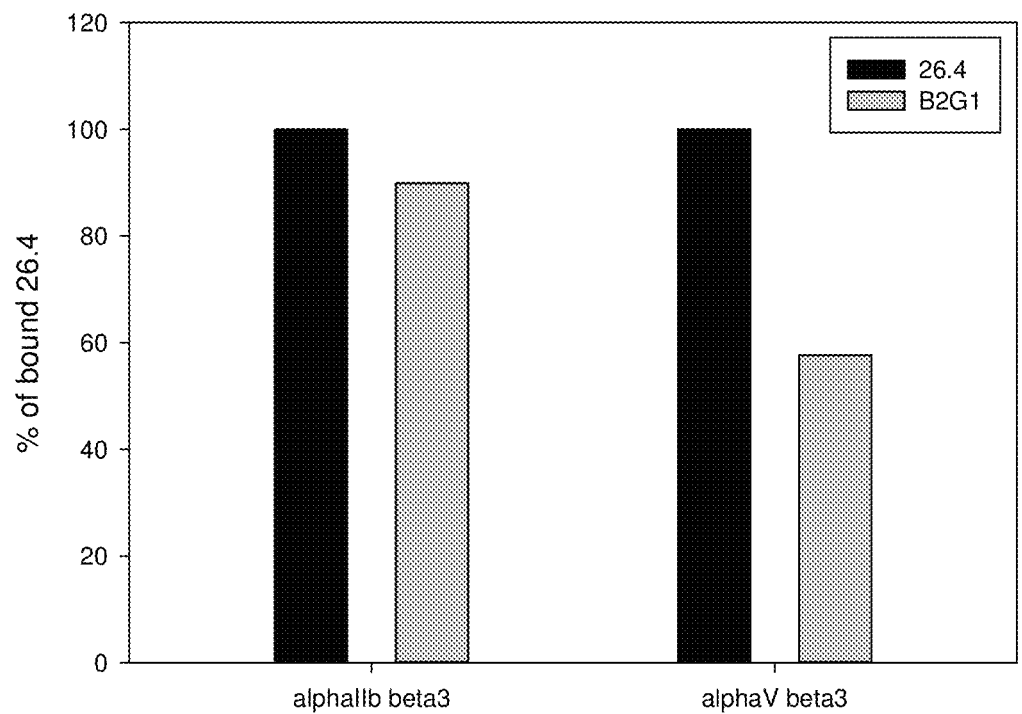
Figure 5D:
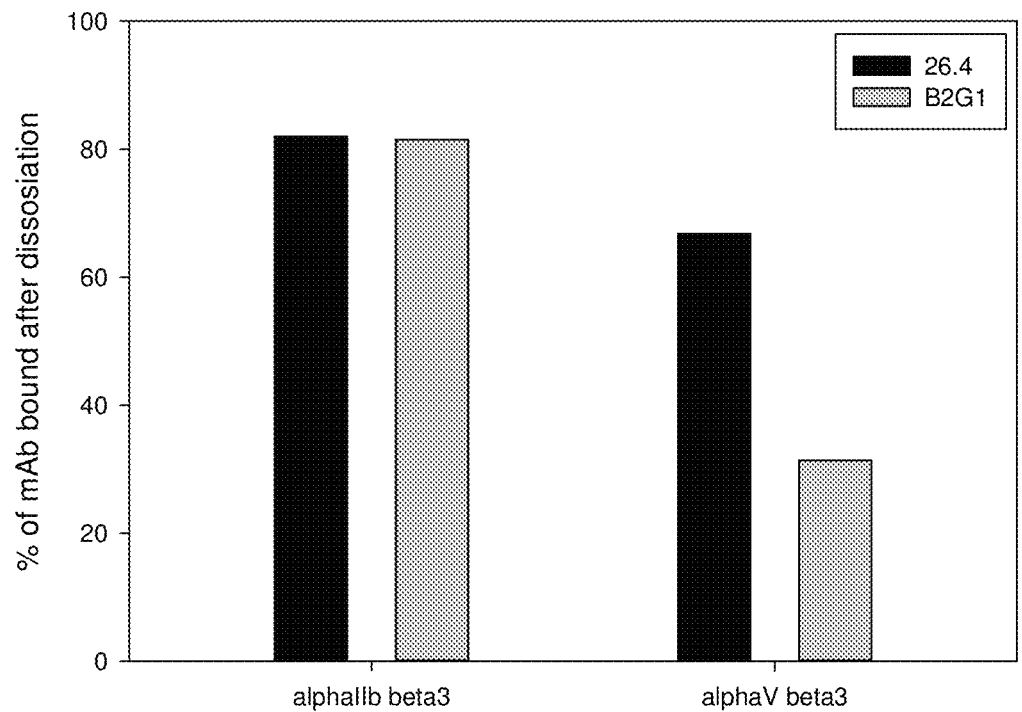
Figure 5E:
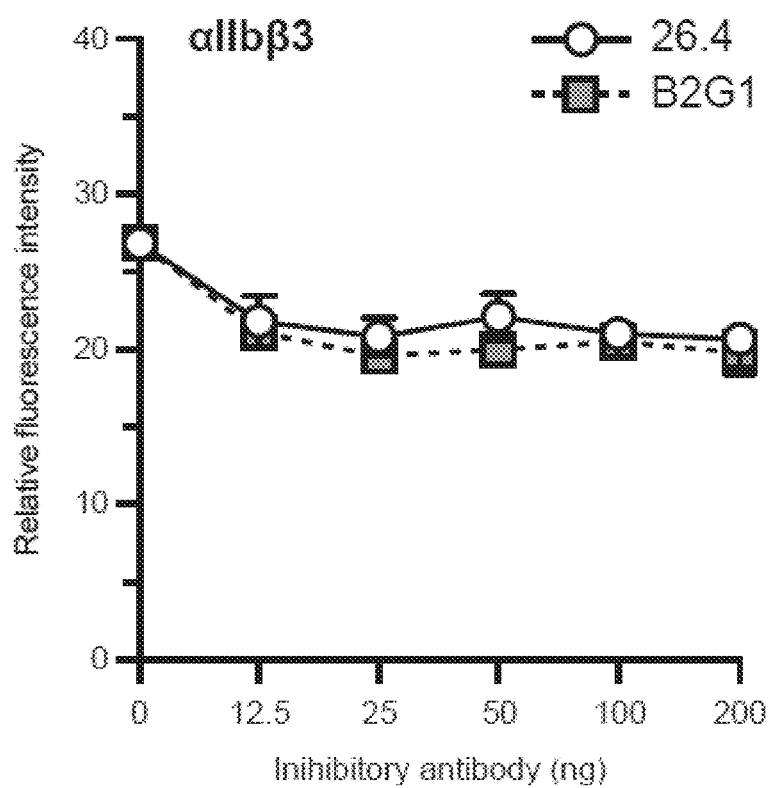
Figure 5F:
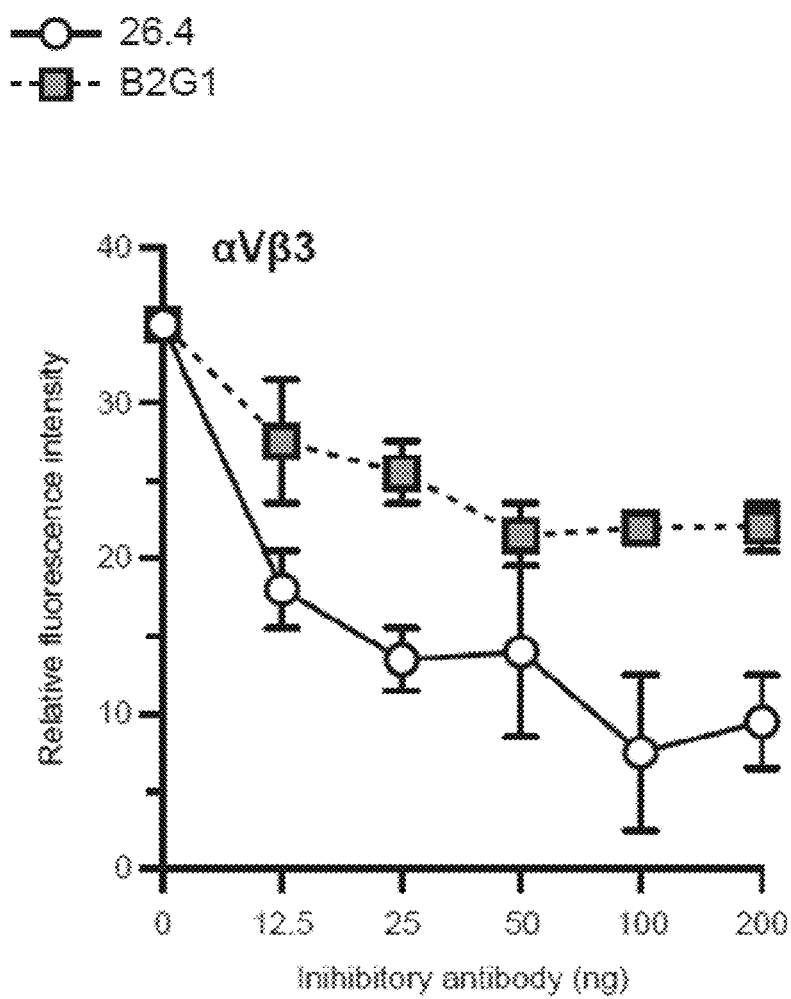

To compare the capacity of 26.4 and B2G1 to inhibit binding of mAb SZ21 to HPA-1a antigen, beads coupled with β3 integrin were preincubated with various concentrations of 26.4 or B2G1 and subsequent binding of FITC-conjugated SZ21 to HPA-1a antigen was evaluated by flow cytometry (FIGS. E and F). Relative fluorescence intensity=mean fluorescence intensity of each sample (mean±SEM)–mean fluorescence intensity of beads coupled with β3 integrin from HPA-1bb platelet lysate. Every sample was run in duplicate. The presented graphs represent four independent experiments using beads coupled with β3 integrin from platelet lysate as shown in FIG. 5E or from trophoblast cell lysate as shown in FIG. 5F.

Figure 6:
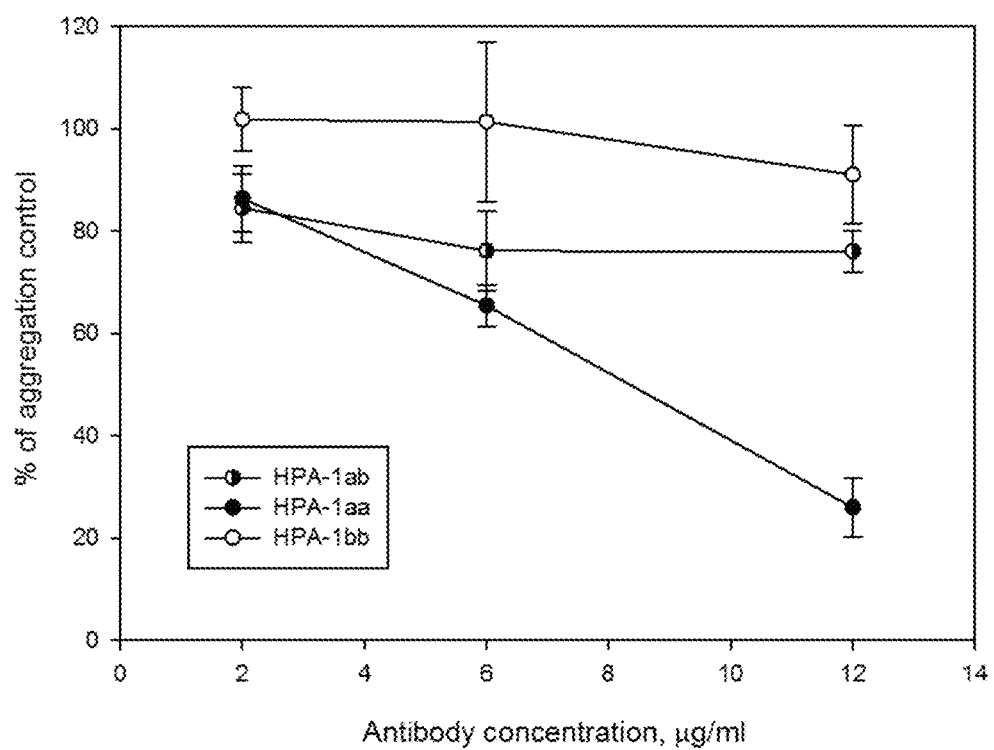

FIG. 6. Effect of mAb 26.4 on platelet aggregation. Blood samples from HPA-1-genotyped donors (n=3 of each HPA-1 genotype) were preincubated with various concentrations of 26.4 IgG1 prior to addition of platelet activator. Aggregation data for blood samples preincubated with 26.4 are presented as percentage of platelet aggregation control.

Figure 7A:
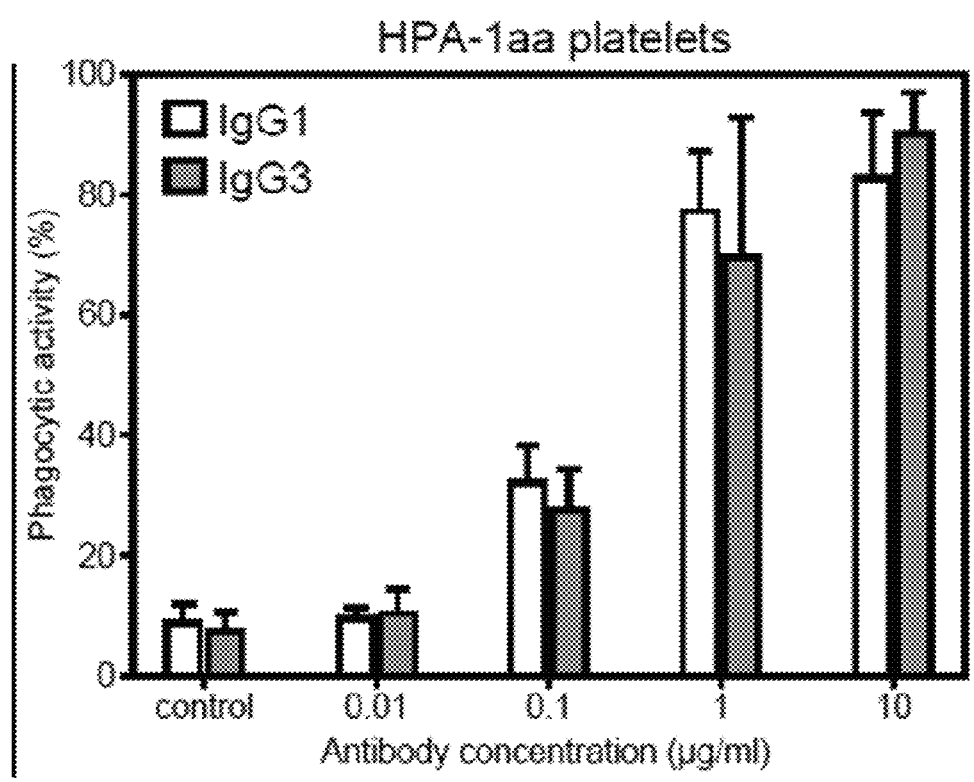
Figure 7B:
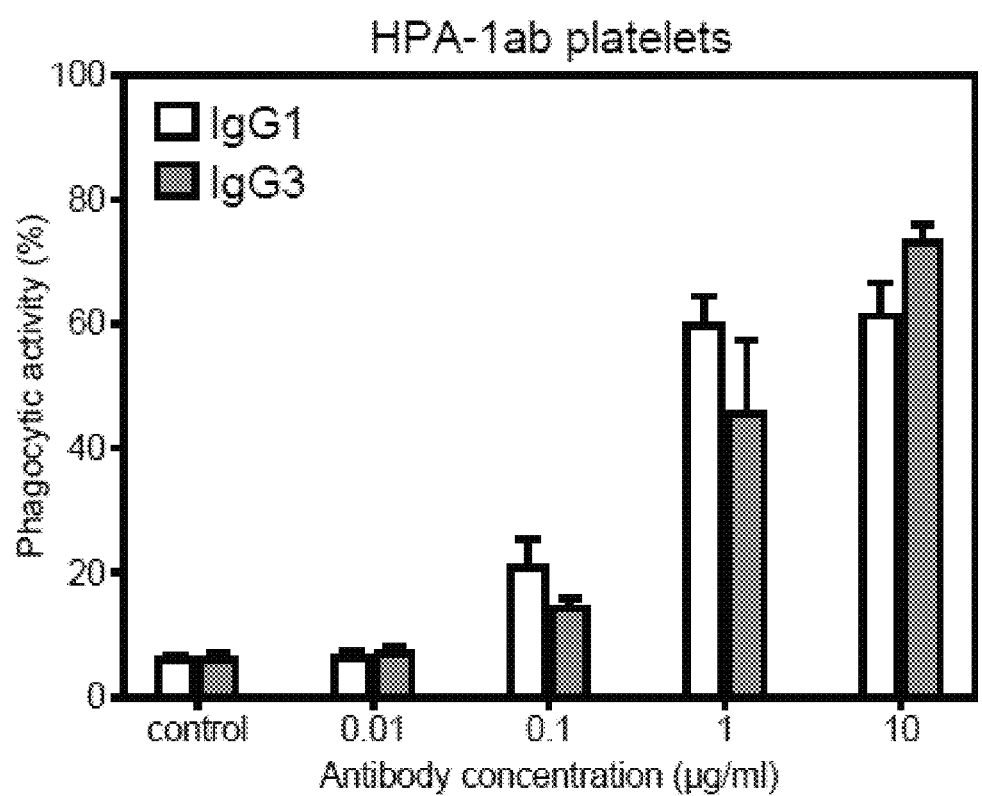

FIGS. 7A and 7B. Monocyte phagocytosis of platelets opsonized with 26.4. Platelets from donors with known HPA-1 genotype (n=3 of each HPA-1 genotype) were CMFDA labeled, sensitized with various concentrations of 26.4 IgG1 or IgG3, and incubated with autologous monocytes. After removal of adhered platelets, monocytes were stained with PE-conjugated anti-CD14 antibody and analysed by flow cytometry. The CD14-positive population was gated and the percentage of FITC-positive monocytes was defined as phagocytic activity (%). Data presented are average phagocytic activity of monocytes from HPA-1a-homozygous donors (FIG. 7A) and from HPA-1ab donors (FIG. 7B).

Figure 8A:
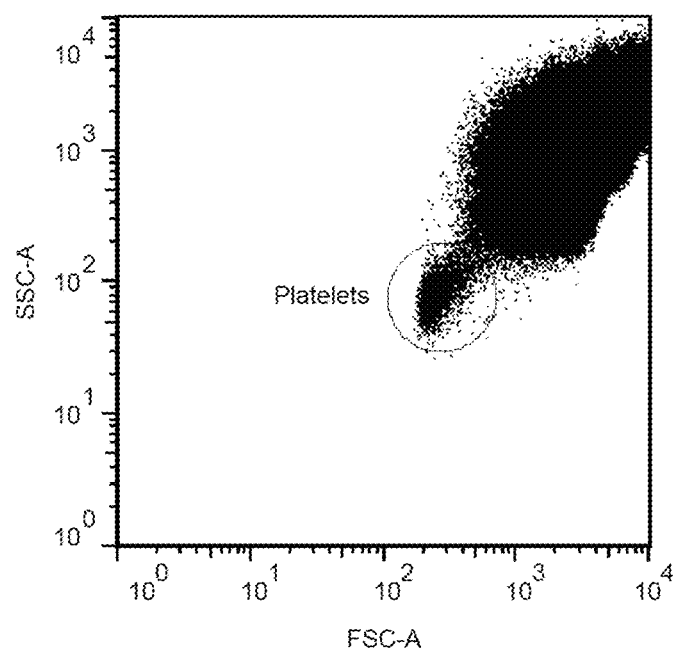
Figure 8B:
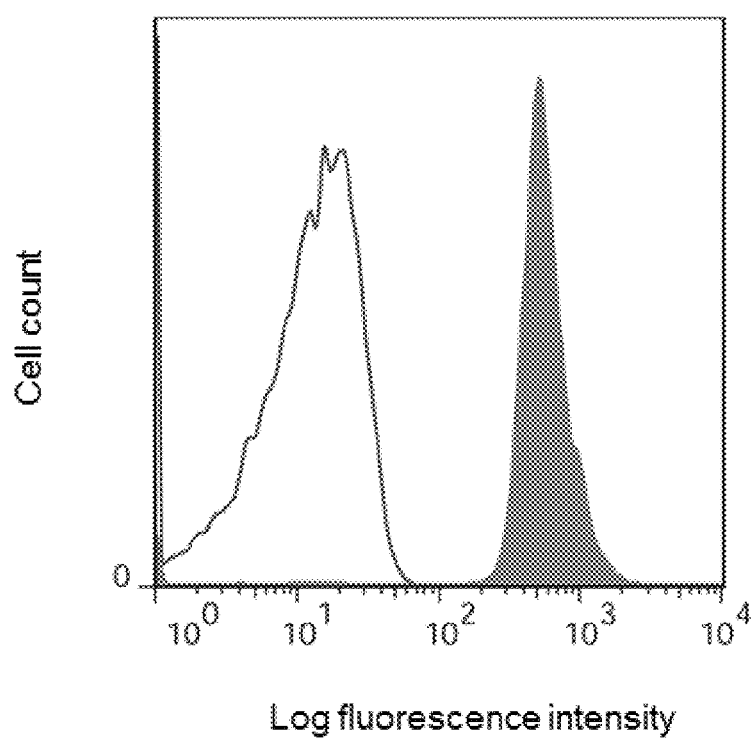

FIGS. 8A and 8B. Illustration of a typical histogram for HPA-1 phenotyping by whole blood flow cytometry using 26.4 conjugated to a fluorescent dye. The population of platelets is gated in a dot plot (upper panel). Overlay of histograms show typical results for HPA-1a-positive (filled) and HPA-1a-negative platelets (lower panel).

Figure 9:
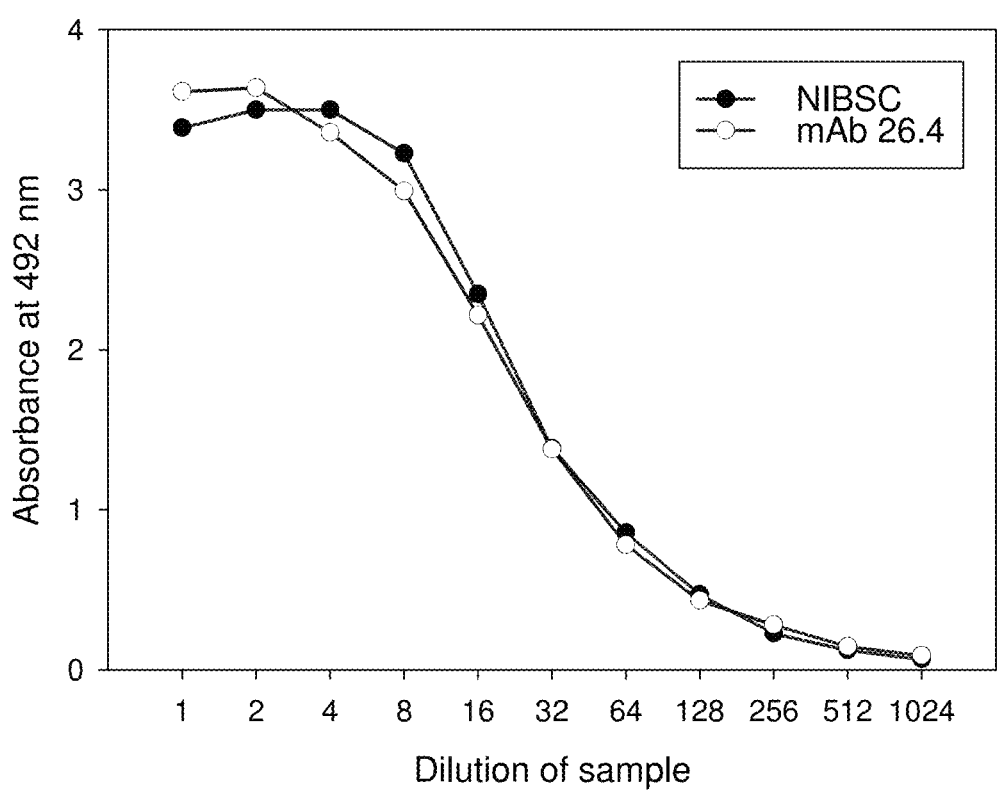

FIG. 9. MAb26.4 preparation has a linearity and range comparable with the commercially available polyclonal anti-HPA-1a NIBSC standard. Plots generated by mean absorbance values for replicate doubling dilutions of NIBSC and proposed mAb 26.4 IgG1 standards in MAIPA assay. Linear portions of the plots were used to determine the anti-HPA-1a activity of the samples.

Figure 10:
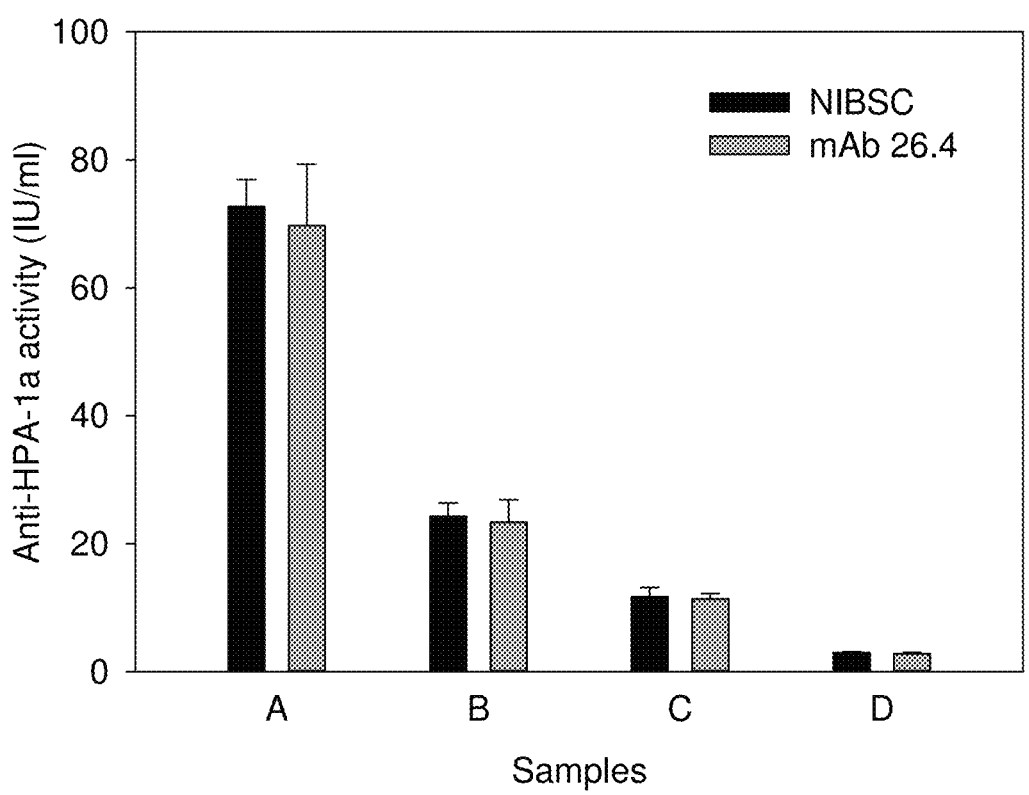

FIG. 10. Anti-HPA-1a activities of samples A, B, C and D in international units per ml (IU/ml). The mean anti-HPA-1a activity value for each sample and standard deviation (CD) from three MAIPA assays were calculated when NIBSC or mAb were used as standards.

Figure 11:
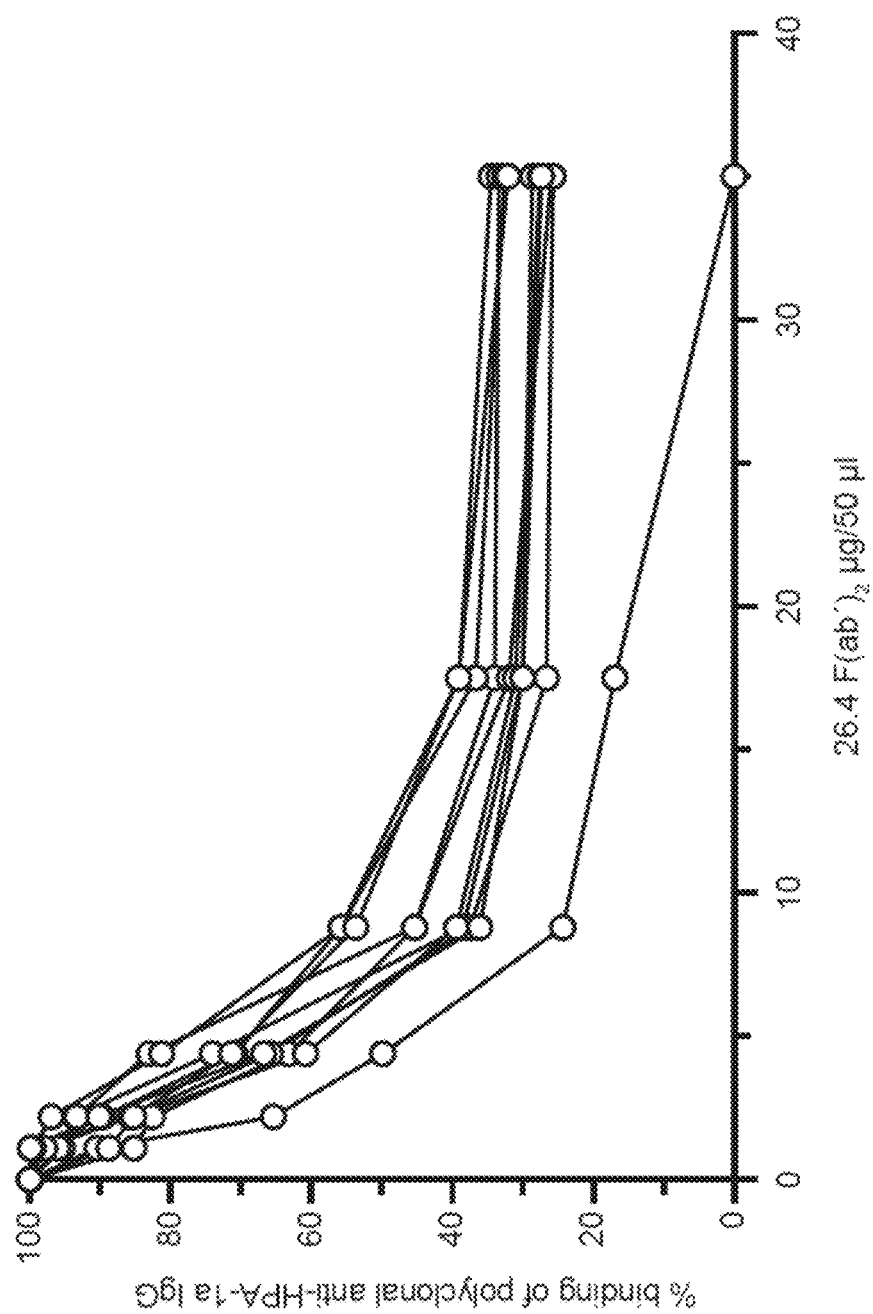

FIG. 11. MAb 26.4 can inhibit binding of polyclonal anti-HPA-1a IgG to HPA-1a homozygous platelets. HPA-1aa platelets were reacted with various concentrations of 26.4 F(ab')$_2$ fragment before adding polyclonal anti-HPA-1a IgG samples. Binding of anti-HPA-1a IgG to platelets was measured by MAIPA. Uninhibited binding of polyclonal antibodies was taken as maximum or 100% binding. Binding in the presence of 26.4 F(ab')$_2$ fragment is presented as a percentage of maximum binding. Dots connected by black lines represent binding of donor samples.

Figure 12:
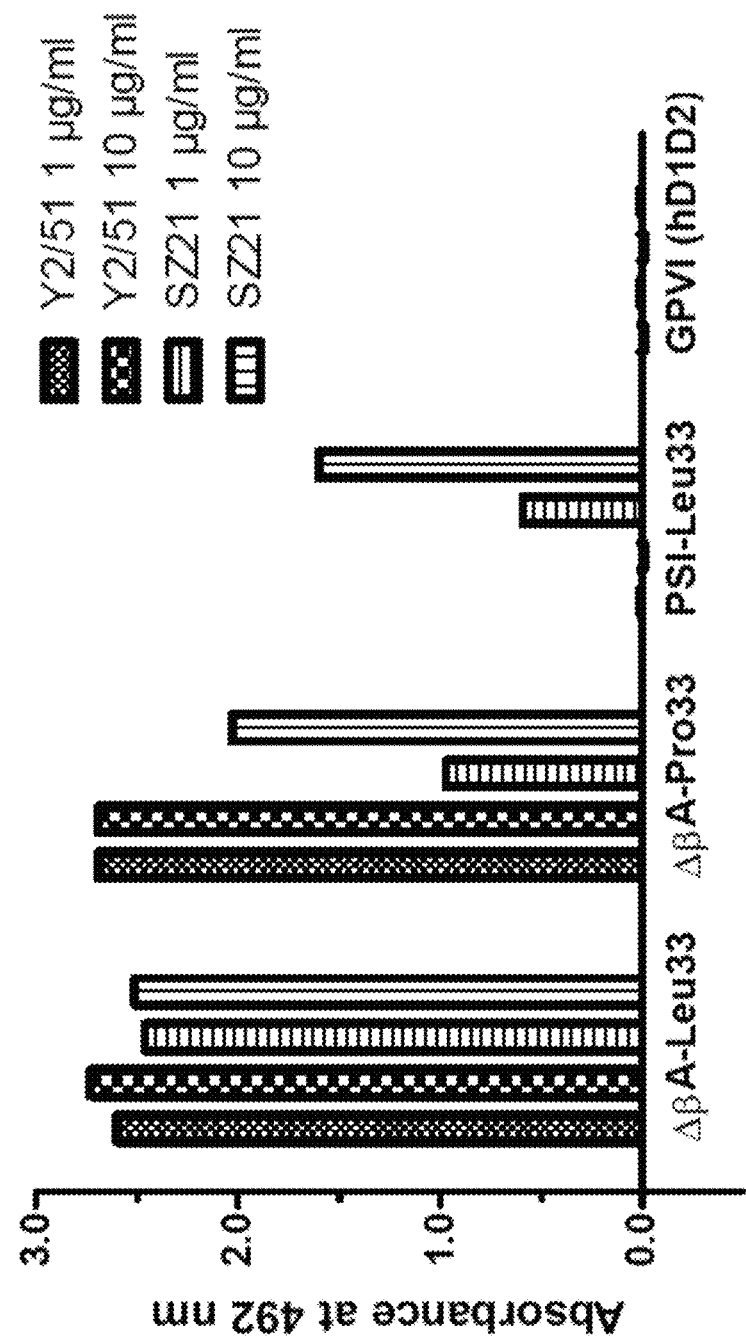

FIG. 12. Reactivity of murine mAbs specific to $\beta_3$ integrin with recombinant $\beta_3$ domain-deletion peptides analyzed by ELISA. Representative of two independent experiments. Experimental details provided in Example 4.

Figure 13:
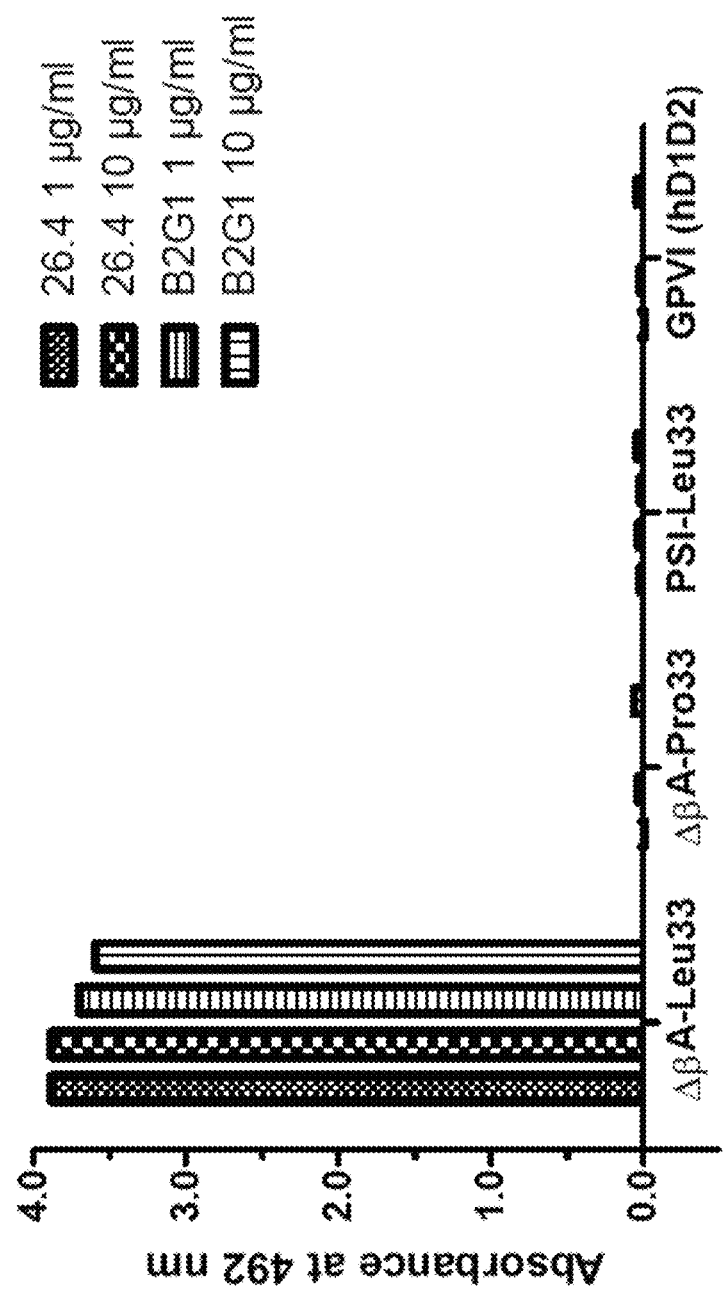

FIG. 13. Reactivity of human mAbs specific to HPA-1a with recombinant β3 domain-deletion peptides analyzed by ELISA. Representative of two independent experiments. Experimental details provided in Example 4.

EXAMPLES

Example 1

Generation and In Vitro Characterization of a Novel Human HPA-1a-Specific Monoclonal Antibody In this study, the aim was to develop a human mAb highly specific for the HPA-1a that would be suitable for prophylactic, therapeutic and screening purposes. An essential quality of such an antibody would be high binding affinity to the HPA-1a and minimal reactivity with the HPA-1b counterpart. As described below, a fully human mAb was developed by immortalization of antigen specific memory B cells from an HPA-1a-negative woman who had developed anti-HPA-1a antibodies upon immunization in connection with a non-compatible pregnancy (i.e. wherein the fetus was HPA-1a positive).

Materials and Methods

Donor Material

Peripheral blood was donated by a woman who was HPA-1a immunized in connection with pregnancy. She gave birth to two HPA-1a-positive babies with severe thrombocytopenia and subcutaneous haemorrhages. The donated blood sample was taken 4 weeks after delivery of the second child. The plasma anti-HPA-1a antibody level was 150 IU/ml as measured by quantitative monoclonal antibody immobilization of platelet antigens (MAIPA) assay (Kiefel V, Santoso S, Weisheit M, Mueller-Eckhardt C., Blood. 1987; 70(6):1722-6).

Isolation of Memory B Lymphocytes

Peripheral blood mononuclear cells (PBMCs) were isolated by density-gradient centrifugation using Lymphoprep (Axis-Shield, Dundee, Scotland) according to the manufacturer's instructions. Memory B cells were isolated based on the method of Traggiai et al. (Nat Med. 2004; 10(8):871-5). Briefly, antibody labelled CD22+ cells were isolated using magnetic-activated cell sorting (MACS, Miltenyi Biotech, Germany), incubated with FITC-conjugated goat anti-human IgD, IgM and IgA antibodies (Dako, Denmark). The CD22$^+$IgD$^-$IgM$^-$IgA$^-$ cell population, IgG$^+$ memory B cells, was identified and isolated by fluorescent-activated cell sorting (FACSAria BD Biosciences). Flow cytometry data was analysed by FlowJo software (TreeStar, Ashland, Oreg., USA).

EBV Transformation of Memory B Cells

Isolated memory B cells were seeded at 400 cells per well in 96 U-bottom cell culture plates and cultured in complete medium (Iscove modified Dulbecco medium (IMDM), 10% FBS and 100 U/ml Penicillin, 100 U/ml Streptomycin) with EBV-containing supernatant from a marmoset lymphoblast cell line B95.8 (ATCC number: VR-1492) and 0.6 µg/ml phosphorothioated CpG ODN2006 (15) (Integrated DNA technologies, Belgium) in humidified atmosphere at 37° C., 7.5% $CO_2$. After 2 weeks, the culture supernatants were tested for the presence of HPA-1a-specific IgG.

Selection of HPA-1a-Specific B-Lymphoblasts

HPA-1a-positive platelets were prepared from platelet rich plasma (PRP) (by pelleting) and labelled with carboxyfluorescein diacetate succinimidyl ester (CFSE; Invitrogen, Carlsbad, Calif.). Cells from B-lymphoblast cultures secreting anti-HPA-1a IgG were stained with PerCP-conjugated anti-CD45 antibody (Caltag) and incubated with CFSE-labelled platelets. B-lymphoblasts binding HPA-1a-positive platelets were sorted one cell per well into 96 well U-bottom culture plates by FACS and cloned in the presence of gamma irradiated allogeneic PBMC (10.000 cells per well).

Generation and Detection of Anti-HPA-1a IgG Secreting Hybridomas

Clonal B-lymphoblasts were fused to a non-secreting mouse-human heteromyeloma cell line K6H6/B5 (ATCC number: CRL-1823) at a 1:10 ratio using stirring method with polyethylene glycol (P7306, Sigma-Aldrich). Fused cells were seeded into the wells of a 48-well plate and cultured in complete medium. Hypoxanthine, aminopterin and thymidine (HAT; Sigma-Aldrich) selection was initiated 24 hours after cell fusion and continued for 7 days. Hybridoma supernatants were screened for anti-HPA-1a IgG by MAIPA or flow cytometry. For the MAIPA, we used 50 µl of culture supernatant and mouse monoclonal anti-CD61 antibody clone Y2/51 (Dako, Denmark) as capture antibody. For the flow cytometry assay, $2 \times 10^6$ HPA-1a-positive platelets were incubated with 50 µl of cell culture supernatant, washed and stained with FITC-conjugated anti-human IgG antibodies (Dako, Denmark). Positive cultures were further subcloned 3 times to isolate stable anti-HPA-1a antibody-secreting hybridomas. The IgG subclass of the mAb was tested by ELISA. Goat anti-human antibodies (Caltag) were used to coat the ELISA plate (Maxisorp, Nunc) and biotin-conjugated mouse anti-human anti-IgG1, IgG2, IgG3 and IgG4 mAbs were used as detection antibodies (clones HP6069, HP6002, HP6047 and HP6025, respectively, Invitrogen).

MAIPA Assay

The MAIPA technique described in detail in Killie et al, 2010 was followed (Killie et al. 2010. Quantitative MAIPA: Comparison of different MAIPA protocols. *Transfusion and Apheresis Science* 43: 149-54). Briefly, washed platelets were incubated with human serum or human mAb followed by a mouse monoclonal anti-GPIIb-IIIa antibody, clone Y2/51 (Dako). Platelets were then lysed and supernatant was added to a microplate precoated with anti-mouse IgG. Human antibodies bound to GPIIb-IIIa were detected with labelled anti-human IgG and a suitable substrate. National Institute of Biological Standards and Control (NIBSC) polyclonal anti-HPA-1a standard (Allen D et al. 2005. Collaborative study to establish the first international standard for quantitation of anti-HPA-1a. *Vox Sanguinis* 89:100-4) were used to create a linear standard curve for quantitative MAIPA. Levels of specific antibodies in the samples were calculated using a linear regression equation.

Purification of IgG from Cell Culture Supernatant

The IgG fraction of cell culture supernatant was isolated by 40% saturated ammonium sulphate precipitation followed by Protein G affinity chromatography (Protein G Sepharose 4 FastFlow, GE Healthcare). The eluted IgG was dialyzed against phosphate buffered saline (PBS) and concentrated using Microcon centrifugal filter devices (Ultracel YM-50, Millipore).

Amplification and Sequencing of Ig Variable Region Genes

Total RNA was isolated from clonal B-lymphoblasts using the RNeasy Mini Spin kit (QIAgen, Hilden, Germany). cDNA was synthesised via reverse transcription using primers specific for the human IgG constant regions. The resulting cDNA was used as a template for polymerase chain reaction (PCR) to amplify IgG variable heavy and light region genes (VH, V$\lambda$ and V$_K$). The genes were amplified in separate PCR reactions for the individual heavy and light chain gene families, using sense primer specific to one of the leader regions, and anti-sense primer to the heavy and light chains constant regions. The PCR products were identified using 1.5% agarose gel electrophoresis and cloned into pCR2.1-TOPO vectors (TOPO TA cloning kit, Invitrogen) followed by sequencing of plasmid minipreps (Miniprep kit, QIAGEN). Sequencing reactions were precipitated and run on a 3130xl Genetic Analyzer (Applied Biosystems) at the sequencing core facility at the Faculty of Health Sciences, UiT, The Arctic University of Norway.

Analysis of Ig Variable Region Genes and Mutations

The nucleotide sequences were analyzed in the international ImMunoGeneTics (IMGT) database of human germline genes using IMGT/V-QUEST program available at http://www.imgt.org (Brochet X, Lefranc M-P, Giudicelli V. Nucleic Acids Research. 2008; 36 (suppl 2):W503-W8). Affinity maturation process (antigen selective pressure) leads to clustering of replacement (R) mutations as opposed to silent (S) mutations within complementarity determining regions (CDRs), which bind the antigen. The framework regions (FRs) maintain the antibody structure and accumulate S as opposed to R mutations. The multinomial distribution model was used to determine whether relative abundance of R mutation in CDRs and S mutations in FRs accumulated at a rate higher than predicted to occur by chance based on codon composition of the parent germline sequence. Mutations were identified for framework regions (FRs) 1, 2 and 3 and complementary determining regions (CDRs) 1 and 2 and imported along with Ig corresponding germline sequences into JAVA applet at http://www-stat.stanford.edu/immunoglobulin/ for multinomial analysis (Lossos I S, et al. J Immunol. 2000; 165(9):5122-6).

Generation of Recombinant Anti-HPA-1a IgG1 and IgG3

Synthesis of the 26.4 Heavy and Light Chain Genes

The heavy and light chain variable region genes coding for antibody 26.4 were synthesised by GenScript (Piscataway, N.J., USA) optimizing the codon usage in the synthesised genes for high level antibody expression in human cells. Two variants of the 26.4 heavy chain gene were synthesised utilizing the γ1 and γ3 heavy chain constant regions. Restriction enzyme recognition sites Esp3I and EcoRI were inserted into the flanks of the synthesised genes, for subsequent use in the cloning of the genes into the pFRIDA vector (modified pLNO vector—Norderhaug L et al., *J Immunol Methods* 204: 77-87).

Cloning of the Genes

Each of the 26.4 genes was supplied in the pUC57 vector. The pUC57 vector containing the synthesised gene was digested with restriction enzymes Esp3I and EcoRI (Fermentas, Burlington, Canada) and the DNA fragment corresponding to the size of the heavy or light chain was isolated by agarose gel electrophoresis using the Qiagen Gelelute kit (Qiagen, Germany). The pFRIDA cloning vector was processed in the same way by digestion with restriction enzymes Esp3I and EcoRI, and subsequent isolation of the digested vector by agarose gel electrophoresis. The digested genes were ligated into the linearized vector using T4 DNA ligase (NEB, USA) and then transformed into XL-10 GOLD competent cells (Stratagene, USA). Transformed cells where selected on ampicillin containing growth agar. Bacterial colonies were selected by growing 14 hours in ampicillin containing liquid media and vector DNA was isolated using plasmid minipreps. The vector DNA was verified to contain the correct insert by restriction enzyme analysis.

Transient Transfection of HEK293E Cells for Expression of Antibody 26.4

Five million HEK293E cells were added to 25 ml DMEM medium (BE12-614F, Lonza) supplemented with 10% FBS and 4 mM L-glutamine. The cell-containing medium was transferred to a standard medium cell culture flask (T75) and incubated for 18 hours in humidified atmosphere at 37° C., 5% $CO_2$. A transfection mixture was prepared by adding 5 μg vector DNA (0.1 μg/ml) expressing the 26.4 light chain, 5 μg vector DNA (0.1 μg/ml) expressing the desired 26.4 heavy chain (γ1 or γ3) and 375 μl RPMI into a test tube. The mixture was preheated to 80° C. and cooled to 4° C. Polyethylenimine Max (PEI Max, 2 mg/ml; 24765-2, Polysciences Inc) was heated simultaneously, but cooled to RT in order to prevent precipitation. Of the PEI solution, 65 μl was added to the transfection mixture before the tube was left to incubate at RT for 8 min. DMEM medium (10% FBS, 4 mM L-glutamin) (3375 μl) was then added to the test tube. The medium from the cell culture flask with HEK293E adherent cells was removed and replaced with the reaction mixture. The reaction mixture was allowed to cover cells for 2 hours before adding 25 ml DMEM medium supplemented with 10% FBS and 4 mM L-glutamine. The transfected cells were allowed to grow for 2-5 days before the supernatant was harvested and tested for production of IgG. The concentration of human $IgG_1$ and $IgG_3$ in samples was quantitated by ELISA, with goat anti-human IgG Fc (Sigma) as coating and ALP-conjugated goat anti-human IgG Fc (Sigma) as detection antibodies. Human IgG1 and IgG3 (I 5154 and I 5654 respectively, Sigma) were used as internal standards.

Surface Plasmon Resonance (SPR) Analysis

SPR technology was used to assess the binding properties of the mAbs (Biacore T200 instrument, Biacore AB, Uppsala, Sweden). The αIIbβ3 integrin was isolated from HPA-1aa and -1bb platelets by affinity chromatography as described previously (Bakchoul T, Meyer O, Agaylan A, Bombard S, Bein G, Sachs UJH, et al. *Transfusion*. 2007; 47(8):1363-8), using a sepharose (CNBr-activated Sepharose 4 Fast Flow, GE Healthcare) column coupled with mouse anti-β3 mAb (clone AP3, ATCC number HB-242). The integrin αVβ3 was obtained from Millipore (cat. No: CC1018). The integrin αVβ3 was purified from human placenta by affinity chromatography using immobilized monoclonal antibodies to αVβ3 integrin. A tissue detergent extract applied to the column was prepared as previously described (Belkin V M, Belkin A M, Koteliansky V E., The Journal of Cell Biology, 1990; 111(5):2159-70). The purified αIIbβ3 integrins (HPA-1a and HPA-1b antigen carrying versions) and αVβ3 were immobilized to the surface of a CM5 sensor chip on three different flow cells (FCs) at a density of 400, 340 and 480 response units (RU) respectively using standard amine coupling chemistry. An FC treated with the same chemicals but without protein was used as a reference surface. Purified monoclonal IgG samples (various concentrations) were injected over the chip surface at a flow rate of 30 μl/min. An association step of 120 sec was followed by a dissociation step of 120 sec. Regeneration of the sensor chip surface was accomplished using 10 mM Glycine-HCl (pH 1.5). The experiments were performed at 25° C. The collected data were analysed using BiaEvaluation 2.0.1 software. The amount of the immobilized β3 integrin available for antibody binding was measured by injection of the anti-β3 mAb (clone SZ21) at a concentration of 20 μg/ml. Around 80 RU on the αIIbβ3-immobilized chip (FIG. 4B) and 25 RU on the αVβ3-immobilized chip (data not shown) have been generated. All chemicals for the Biacore experiment were purchased from GE Healthcare.

Flow Cytometric Antibody Binding-Inhibition Assay

The capacity of mAb 26.4 to inhibit binding of mAb SZ21 to the HPA-1a epitope was evaluated using beads indirectly coupled with β3 integrin and compared to a previously described recombinant HPA-1a antibody B2G1 (Garner, et al., (2000), *British Journal of Haematology* 108: 440-7; Griffin H, et al., (1995), *Blood* 86: 4430-6). First, Dynabeads M-270 Epoxy (Life Technologies) were coupled with an anti-β3 antibody (clone EPR2417Y, specific for C-terminal part of β3-integrin, Abcam, Cambridge, England) according to the manufacturer's instructions. Next, beads were incubated with cell lysate from a trophoblast cell line expressing β3-integrin (TCL-1 (Lewis M P, et al. (1996), *Placenta* 17: 137-46); genotyped HPA-1aa) or platelet lysate from HPA-1a positive platelets over night at 4° C., to bind β3 integrin from cell lysates. Beads were washed with RIPA buffer (Sigma) and incubated with various amounts (12.5 ng, 25 ng, 50 ng, 100 ng and 200 ng) of 26.4 and B2G1 in RIPA buffer for 15 min at RT. These amounts of antibody were incubated with beads in a total volume of 200 μl. The concentrations were therefore 62.5, 125, 250, 500 and 1000 ng/ml, respectively. After a washing step, beads were incubated with 5 μl of FITC-conjugated mAb SZ21 (Beckman Coulter) in 200 μl bead suspension for 15 min at RT in dark. After a washing step, beads were resuspended in PBS, and analyzed by flow cytometry.

Platelet Aggregometry (Multiplate)

Impedance platelet aggregometry was used to assess the effect of mAbs on platelet aggregation (Multiplate analyser, Roche, Basel, Switzerland). Study participants (n=3 of each HPA-1 genotype) were healthy volunteers with known HPA-1 genotype who did not take any medications affecting platelet function 10 days prior to blood collection. Whole blood samples were drawn by peripheral venipuncture into 3 ml tubes, containing recombinant hirudin as anticoagulant. The blood was kept at RT and the measurements were performed within 2 h from blood collection. The 480 μl blood samples were incubated with various mAb concentrations (20 μl volume) for 5 min before the addition of platelet activator, thrombin receptor activating peptide-6 (TRAP-6). Blood samples with addition of 20 μl of PBS buffer were used to determine the individual platelet function triggered by TRAP-6. To test the effect of the 26.4 on platelet aggregation without platelet activator, the 0.9% sodium chloride solution was used instead of the TRAP-6. Aggregation was continuously recorded over 6 min in two independent measuring units per test. Increase of impedance due to the attachment of platelets to the electrodes was detected and converted into arbitrary aggregation units (AU) plotted against the time. The aggregation was quantified by the area under the curve (AUC) in aggregation units (AU× min). Platelet count in blood samples was measured using Sysmex XN-1000 Hematology analyzer.

Anti-HPA-1a-Mediated Platelet Phagocytosis by Monocytes Assay

Buffy coat was diluted 1:4 in phosphate-buffered saline (PBS) and layered over Lymphoprep medium (Axis-Shield, Dundee, United Kingdom) followed by 15 min centrifugation at 700 g without brakes. The interface was collected, and 40 mL 0.2% PBSA (0.2% bovine serum albumin in PBS) was added. PBMCs were pelleted by centrifugation at 300 g for 6 minutes. The platelets were pelleted from the supernatant by centrifugation at 2000 g for 6 minutes and resuspended in 0.2% PBSA 0.3% EDTA. Monocytes were isolated from PBMCs using RosetteSep Human Monocyte Enrichment Cocktail (StemCell Technologies, Vancouver, Canada) as described previously (Ahlen M T, Husebekk A, Killie M K, Skogen B, Stuge T B. Blood. 2009; 113(16): 3838-44) and adjusted to $2 \times 10^6$ cells/ml in 10% FBS-IMDM (BE12-722F, Lonza).

In 1 ml volume $10^8$ platelets were labelled with CellTracker Green CMFDA (5-chloromethyl fluorescein diacetate, C7025, Invitrogen) at 0.25 µM final concentration according to the manufacturer's instructions. CMFDA-stained platelets were adjusted to $2 \times 10^8$/ml in 0.2% PBSA 0.3% EDTA and 50 µl were incubated with different concentrations of human monoclonal anti-HPA-1a IgG for 20 min at RT. After a washing step, 50 µl of monocytes were added resulting to a total volume of 100 µl and platelet to monocyte ratio 100:1 in duplicate tubes and incubated at 37° C., in a 7.5% $CO_2$ humidified atmosphere for 2 h. The monocytes were pelleted by centrifugation at 300 g and incubated with 0.25% trypsin/EDTA solution (T4049, Invitrogen) for 2 min at 37° C. to remove extracellular adherent platelets. After a washing step, the cells were stained with PE-conjugated anti-CD14 antibody (Invitrogen) and analysed by flow cytometry. Human IgG1 and IgG3 of irrelevant specificities were used as assay negative controls.

Statistics

Sigma Plot 12.5 software (San Jose, Calif.) was used to present aggregation and phagocytosis experimental data. GraphPad Prism 5 software (San Diego, Calif.) was used to present flow cytometric antibody binding inhibition assay data.

Ethics

The study was approved by Regional Committee for Medical Research Ethics, North-Norway, (approval no: 2009/1585 and 2013/126/REK). All volunteers who donated blood samples have signed a written informed consent (Blood Bank, University Hospital of North Norway).

Results

Figure 1A:
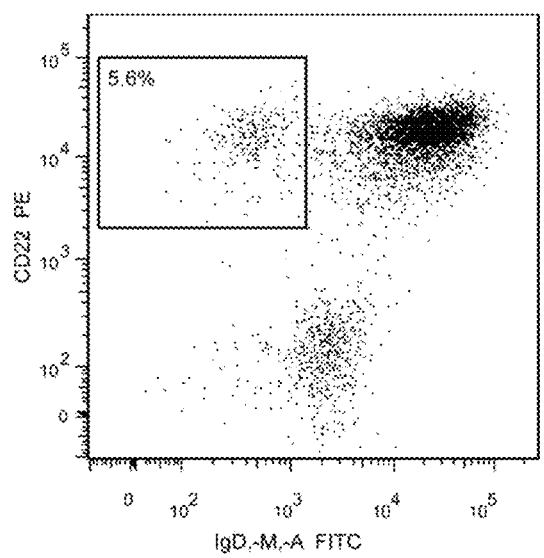
FIGS. 1A and 1B. Isolation of HPA-1a-specific B-lymphoblasts.
Figure 1B:
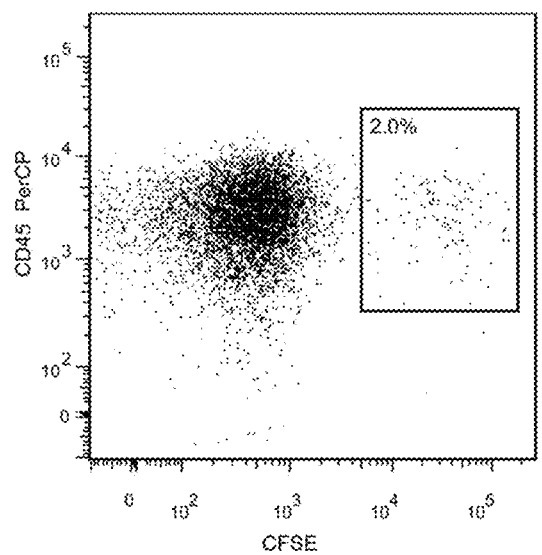
Figure 2A:
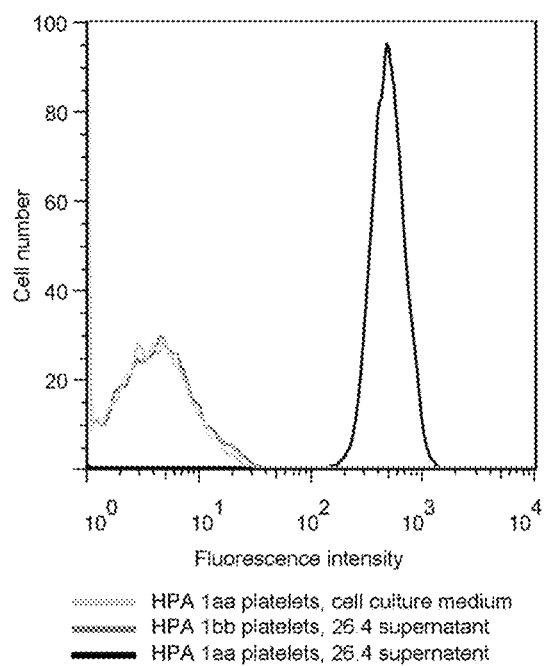
FIGS. 2A and 2B. Binding of mAb 26.4 to HPA-1 antigens on intact platelets.
Figure 2B:
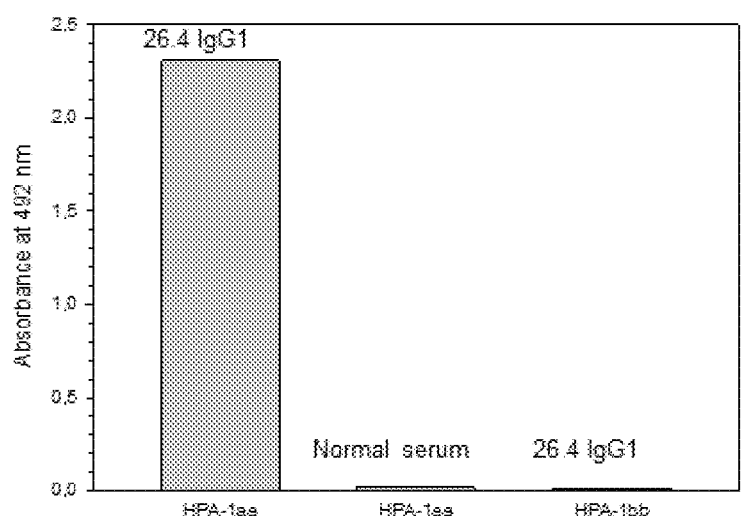

Monoclonal IgG Specific for HPA-1a was Generated by Immortalising HPA-1-Specific Memory B Cells It was reasoned that B cells producing anti-HPA-1a-specific IgG may be present at elevated numbers in the circulation of women who have given birth to a child affected by FNAIT, and that an antibody derived from a single HPA-1a-specific B cell may give rise to a limitless supply of monoclonal antibodies with this specificity. In order to isolate HPA-1a-specific IgG$^+$ B cells, PBMCs were first isolated from an HPA-1a alloimmunized woman. Blood was drawn 4 weeks after delivery of an FNAIT affected child. To enrich for B cells we reacted about 40 million PBMCs with a monoclonal antibody specific for the pan B cell marker CD22 and purified the sensitized cells from the PBMCs by magnetic-activated cell sorting (MACS). About 3 million CD22$^+$ B cells were recovered. To enrich for IgG$^+$ B cells, the CD22$^+$ cells were reacted with fluorescently labeled polyclonal antibodies to human IgM, IgA and IgD (IgMAD) isotypes and the IgMAD$^-$ cells were isolated by fluorescence-activated cell sorting (FACS). The IgMAD$^-$ cells amounted to 5.6% of the CD22$^+$ cells. (FIG. 1A). In a separate experiment the IgMAD$^-$ population of CD22$^+$ cells was shown to consist of mostly IgG$^+$ cells (data not shown). About $10^5$ cells were isolated by FACS. To isolate HPA-1a-specific B cells from the FACS-isolated cells, our strategy was to immortalize the sorted cells by transformation with the Epstein-Barr virus (EBV) and to screen for transformed cells producing anti-HPA-1a antibodies. Therefore, the sorted cells were treated with culture supernatant containing EBV in the presence of a polyclonal activator of memory B cells, CpG oligonucleotide (CpG 2006) to enhance transformation and divided in 240 wells (about 400 cells per well) on microtitre plates. After 2 weeks, 27 B-lymphoblast cultures containing HPA-1a-specific antibodies were identified by MAIPA. After 7 additional days in culture, only half of the B-lymphoblast cultures retained production of specific antibodies. Cells from the culture secreting the highest amount of anti-HPA-1a IgG were incubated with CFSE-stained HPA-1a-positive platelets. The CFSE-positive lymphoblasts, 120 cells, were isolated individually by FACS (FIG. 1B) and expanded in culture. Notably, we observed much nonspecific binding of platelets to HPA-1a-negative B-lymphoblasts, used as a negative control; the negative control had almost the same frequency of CFSE-positive lymphoblasts (data not shown). After 3 weeks of expansion, one clonal B-lymphoblast culture secreting HPA-1a-specific antibodies was identified and clone D18BL26.4 (also referred to herein as 26.4 or mAb26.4) was established. The 26.4 antibody bound specifically to HPA-1a-positive platelets (FIG. 2A and FIG. 2B). A hybridoma cell line, D18BL26.4H, secreting anti-HPA-1a IgG was generated by fusing cells from the 26.4 B-lymphoblasts to heteromyeloma cells (as described in the method section). The secreted IgG subclass was found to be IgG$_3$ by ELISA.

Amplification of Ig Variable Region Gene and Sequence Analysis

Figure 3:
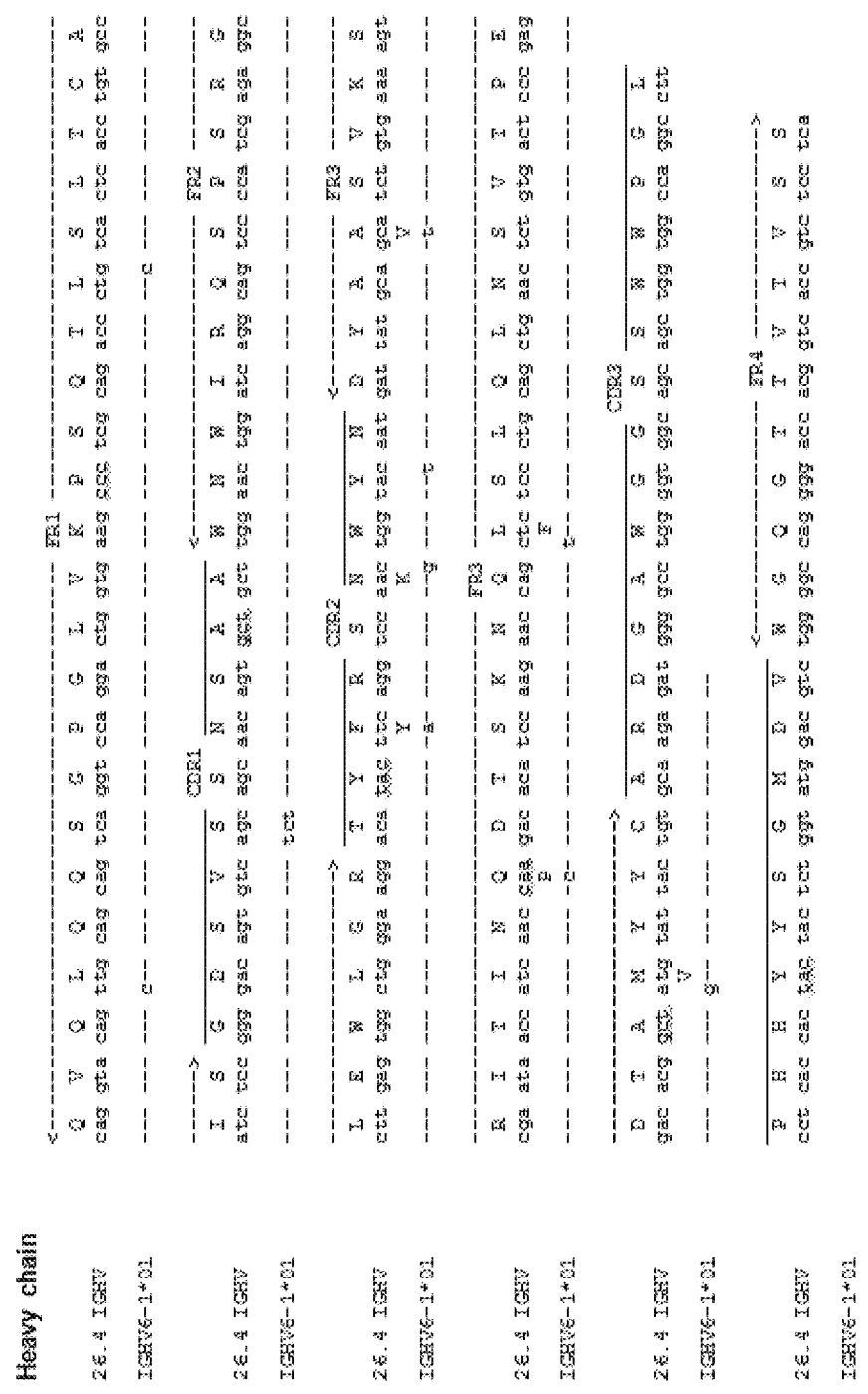

To test for clonality of the D18BL26.4 cell line and to amplify the Ig variable gene sequences, first we isolated mRNA and synthesized cDNA by reverse transcription with primers specific for the human IgG constant regions. The resulting cDNA was used as a template to amplify IgG variable heavy and light region genes (VH, Vλ and $V_K$) in separate PCR reactions for each gene family. The two amplified PCR products of approximately 400 bp in size corresponded to VH6 and VK3 gene families, confirming the clonality of the cells (data not shown). The PCR products were sequenced and the analysis of Ig variable gene sequences enabled identification of the closest known germline genes and the V, D, and J gene segments used during somatic recombination (FIG. 3). For the heavy chain IGHV6-1*01, IGHD6-13*01 and IGHJ6*02 gene segments were used and IGKV3-11*01 and IGKJ4*01 for the light chain.

Recombinant mAb 26.4 is Specific for and Binds Strongly to the HPA-1a Antigen

To facilitate exploration of mAb 26.4 function with different Ig isotypes the gene encoding the Ig heavy-chain variable region in D18BL26.4 cells was combined with IgG1 (26.4G1) and IgG3 (26.4G3) constant domains in different expression constructs. The light-chain variable region gene was combined with a kappa 1 constant domain in a third construct. One heavy-chain and the light-chain constructs were expressed in HEK293E cells following transient transfection. Typically, transfected cultures produced 26.4$G_1$ and 26.4$G_3$ to the supernatants at concentrations of 20-50 µg/ml and 5-20 µg/ml, respectively, as measured by ELISA. Identical to the native 26.4, mAbs 26.4G1 and 26.4G3 bound specifically to HPA-1a-positive intact platelets when tested in flow cytometry and MAIPA (FIGS. 2A and 2B). No binding to HPA-1a-negative platelets was observed. All the experiments from this point were done with recombinant 26.4, and the 26.4G1 version was used unless otherwise noted.

The 26.4 bound specifically to HPA-1a-positive intact platelets when tested in flow cytometry (FC) and MAIPA. No binding to the HPA-1a-negative platelets was observed.

Figure 4A:
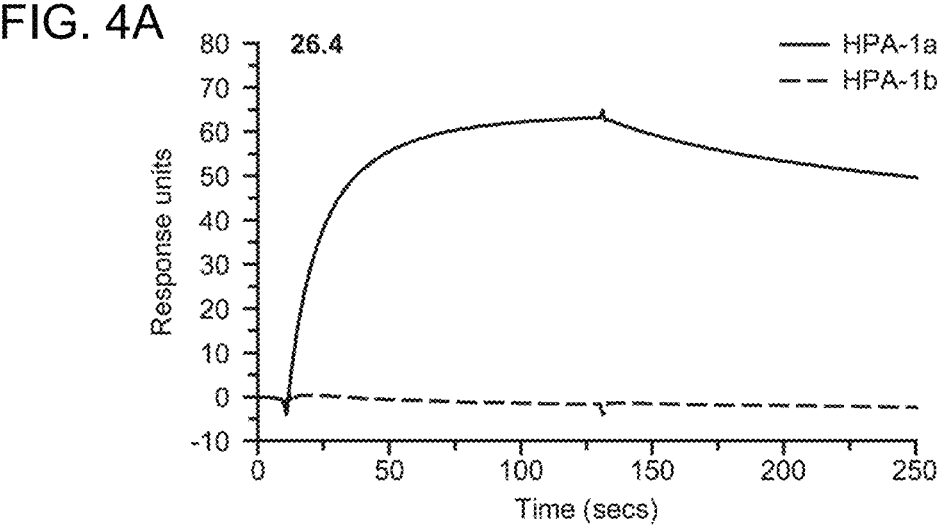
FIGS. 4A and 4B. SPR analysis of mAb binding to HPA-1 antigens. Sensograms generated by binding of 26.4 IgG1 as shown in FIG. 4A and SZ21 as shown in FIG. 4B to the αIIbβ3 bearing the HPA-1a (black line) or HPA1b (dashed line) antigens immobilized to the sensor chip surface. Antibodies were used at a concentration of 20 µg/ml.

In order for more sensitive assessment of specificity, 26.4 binding to purified platelet integrin αIIbβ3 was measured by surface plasmon resonance (SPR). In the surface plasmon resonance (SPR) system, the 26.4 bound exclusively to αIIbβ3 from HPA-1aa individuals; there was no measurable binding to HPA-1a-negative αIIbβ3 (FIG. 4A). Rapid association and slow dissociation indicate that the 26.4 binds strongly to the HPA-1a antigen. The binding properties of 26.4 recombinant antibodies were identical to the hybridoma-secreted batch (data not shown).

Further, we compared binding properties of the 26.4 to the human HPA-1a-specific mAb, clone B2G1, generated by phage display also from a woman alloimmunized in connection with pregnancy (Griffin H, Ouwehand W., Blood. 1995; 86(12):4430-6). Similar association and dissociation curves for 26.4 and B2G1 indicate that affinities of the two mAbs are in the same range (FIG. 5A). Binding affinity of the B2G1 to the recombinant αIIbβ3 was measured previously, $K_D=6\times10^{-8}$ (Santoso S, Kroll H, Andrei-Selmer C L, Socher I, Rankin A, Kretzschmar E, et al. Transfusion. 2006; 46(5):790-9).

Figure 4B:
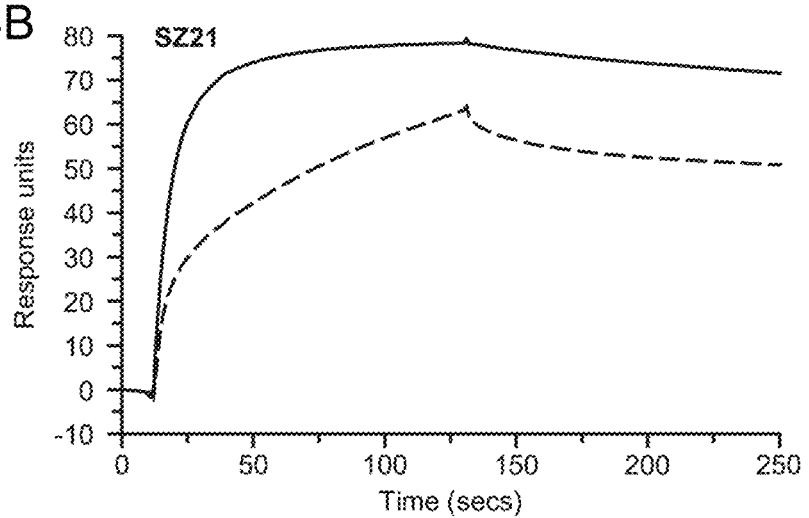

Next, we assessed binding properties and specificity of the previously characterized mouse mAb, clone SZ21 (Weiss E J, Goldschmidt-Clermont P J, Grigoryev D, Jin Y, Kickler T S, Bray P F. Tissue Antigens. 1995; 46(5):374-81). The SZ21 antibody bound both HPA-1a positive and negative integrin αIIbβ3, however, it displayed a higher affinity for HPA-1a as it associated slower and dissociated faster from the HPA-1a negative integrin (FIG. 4B). This binding pattern indicates that SZ21 is pseudospecific for HPA-1a.

MAb 26.4 Displays a Unique Binding Pattern to Integrin αVβ3

As integrin β3 is also part of the vitronectin receptor (αVβ3) we examined whether or not the HPA-1a-specific mAbs 26.4 and B2G1 could bind to purified αVβ3. The source and method of purifying the αVβ3 integrin is described above. Both mAbs bound to the sensor chip surface coupled with αIIbβ3 (HPA-1a) and αVβ3 (FIGS. 5A and 5B). However, 26.4 bound to αIIbβ3 generating 10% more binding response than B2G1. Surprisingly, the difference in binding response was more profound on the surface coupled with αVβ3: 26.4 generated 42% more binding response than B2G1 (FIG. 5C).

Both mAbs dissociated from the αIIbβ3 with nearly identical rate; around 81% of the bound 26.4 as well as B2G1 remained bound at the end of the dissociation period. However, B2G1 dissociated from the αVβ3 over 50% faster than 26.4; 31.4% of B2G1 compared to 66.8% of 26.4 remained bound at the end of dissociation period (FIG. 5D).

The difference is not attributed to any loss of antigen during the regeneration procedure as the B2G1 samples were run before the 26.4 samples over both the αIIbβ3 (FIG. 5A) and the αVβ3 (FIG. 5B) surfaces. Furthermore, the results were produced with various antibody concentrations, 20, 10 and 5 µg/ml (only 20 µg/ml is shown) and similar results have been obtained using sensor chip coupled with higher amounts of integrins (data not shown).

Further association/dissociation data is shown in Table 2

TABLE 2

SPR analysis of mAb 26.4 and B2G1 binding to immobilized αIIbβ3 and αVβ3.

| Integrin complex | 26.4 | | | B2G1 | | |
|---|---|---|---|---|---|---|
| | bound (RU) | bound after dissociation (RU) | % dissociated | bound (RU) | bound after dissociation (RU) | % dissociated |
| αIIbβ3 | 63.1 | 49.6 | 21.4 | 56.1 | 43.8 | 22 |
| αVβ3 | 18.8 | 12.2 | 35.1 | 11.2 | 3.3 | 70.5 |

Due to the observed difference in binding to αVβ3, it was decided to examine the relative efficiencies of 26.4 and B2G1 at inhibiting the binding of a third anti-HPA-1a mAb, SZ21, to αIIbβ3 and αVβ3 (FIGS. 5E and 5F). In this set of experiments, mAb 26.4 was more efficient than B2G1 at inhibiting binding of SZ21 to beads coupled with αVβ3 from trophoblasts (FIG. 5F). In comparison, there was little difference in the efficiency of the two mAbs (26.4 and B2G1) at inhibiting SZ21-binding to beads coupled with αIIbβ3 from platelets (FIG. 5E). Therefore, although mAbs 26.4 and B2G1 appear to bind similarly to HPA-1a on integrin αIIbβ3, they differ in binding efficiency to integrin αVβ3.

MAb 26.4 has Inhibitory Effect on Platelet Aggregation

Since integrin heterodimer αIIbβ3 is a fibrinogen receptor on platelets, we assessed whether 26.4 affects platelet aggregation (FIG. 6). The 26.4 inhibited HPA-1aa platelet aggregation in a concentration-dependant manner: 15, 35 and 80% inhibition at concentrations of 2, 6 and 12 µg/ml, respectively, compared with the aggregation control. The aggregation control was the individual platelet aggregation triggered by TRAP-6. The individual platelet aggregation was taken as 100%. At the lowest mAb concentration, inhibition of aggregation of the HPA-1ab platelets was similar to HPA-1aa. The 6 and 12 µg/ml of mAb equally inhibited aggregation of HPA-1ab platelets by 20%. Importantly, there was no significant effect of the 26.4 on HPA-1bb platelet aggregation. The 26.4 antibody did not affect platelet function when aggregation was measured in samples without platelet activator (data not shown). Platelet count in samples with added mAb in different concentrations did not differ from control samples without mAb for each participant (data not shown). The decrease of platelet aggregation is therefore attributed solely to the inhibition of platelet function.

MAb 26.4 is Potent in Inducing Platelet Phagocytosis

To assess whether 26.4 can induce platelet phagocytosis, we incubated freshly isolated monocytes with 26.4-sensitised CFSE-labelled platelets and measured the frequence of monocytes with ingested platelets by flow cytometry. MAb 26.4 induced phagocytosis of sensitized HPA-1a-homozygous platelets in a concentration-dependent manner (FIG. 7A). MAb 26.4G1 performed similarly to 26.4IgG3. At concentrations 10, 1 and 0.1 µg/ml the antibodies induced around 90, 70 and 30% phagocytosis, respectively. These % phagocytosis values are the % of monocytes that had internalized platelets. The phagocytic activity was close to 10% when 0.01 µg/ml of the antibody was used as well as in negative controls. The phagocytic activity with HPA-1ab platelets was about 20% lower compared to HPA-1aa platelets (FIG. 7B). The antibodies did not affect phagocytosis of sensitized HPA-1a-negative platelets. No synergistic effect was observed when a 1:1 mixture of 26.4G1 and 26.4IgG3 was tested in similar experiments (data not shown).

Discussion

In the study described herein a recombinant monoclonal antibody specific for HPA-1a was derived from a single memory B cell. This B cell was isolated from a woman known to be HPA-1a immunized in connection with pregnancy. This antibody, clone 26.4, has been successfully expressed recombinantly by transient transfection of human cells. It has been found that 26.4 binds strongly to HPA-1a and is highly specific; no reactivity to the HPA-1b allotype was detected. Furthermore, it exhibits only a modest inhibitory effect on HPA-1ab platelet aggregation and can opsonize platelets for enhanced monocyte phagocytosis. Thus, mAb 26.4 holds potential both for FNAIT prophylaxis and HPA-1a typing.

It has been demonstrated herein by sensitive binding assays that there was no measurable cross-reactivity of mAb 26.4 with the native HPA-1b allotype. Without wishing to be bound by theory, it is believed that this can be attributed to selection of the antibody by the human immune system. The difference between the HPA-1 allotypes is a single amino acid, which is leucine in HPA-1a. MAb 26.4 is obviously not binding to leucine alone. Therefore, one possibility is that the antibody has affinity for a surface area that is common to both allotypes and that the allogeneic leucine makes the difference between stable binding with it and no binding without. Alternatively, the single amino acid difference may be associated with a conformational change that in effect creates a new epitope that the antibody can bind to. In either of the above cases, the in vivo selection and affinity maturation in the B cell that gave rise to mAb 26.4 was likely driven towards the highest binding affinity to the alloantigen and at the same time maintaining low cross-reactivity with the HPA-1b autologous counterpart. In developing anti-HPA-1a antibodies by immunization of mice, a similar pressure to select for minimal cross-reactivity with HPA-1b will be lacking. This is consistent with the observations herein of considerable cross-reactivity of the SZ21 antibody with HPA-1b while none was detectable with mAb 26.4. Without wishing to be bound by theory, it is believed that anti-HPA-1a antibodies which are able to cross-react with the antigen HPA-1b (e.g. the antibody SZ21) could cause undesirable immune responses in the mother, e.g. accelerate removal of maternal HPA-1bb platelets from the blood circulation causing thrombocytopenia.

Platelet aggregation is central in haemostasis and thrombosis and integrin αIIbβ3 plays a critical role in it. Previous studies demonstrated that anti-HPA-1a antibodies had an inhibitory effect on platelet aggregation and adhesion of αIIbβ3 and αVβ3 transfected CHO cells to fibrinogen (Joutsi-Korhonen L, Preston S, Smethurst P A, Ijsseldijk M, Schaffner-Reckinger E, Armour K L, et al. Thrombosis and Haemostasis. 2004; 91(4):743-54, and Kroll H, Penke G, Santoso S. Thrombosis and Haemostasis. 2005; 94(12): 1224-9).

The mechanism of fetal platelet destruction by maternal anti-HPA-1a antibodies is not completely understood. Without wishing to be bound by theory it is speculated that IgG sensitized fetal platelets are removed from circulation via FcγR-mediated phagocytosis by mononuclear phagocytes in the spleen and liver and possibly by granulocytes. One application of anti-HPA-1a mAbs is as a prophylaxis against HPA-1a alloimmunization. One of the proposed mechanisms of prevention of immunization against the RhD-antigen is by removing fetal red blood cells from maternal circulation via phagocytosis of anti-RhD IgG-opsonized red blood cells. Similarly, and again without wishing to be bound by theory, it is hypothesised that HPA-1a immunization may be prevented by anti-HPA-1a antibodies by sensitizing fetal platelets which will then be removed from maternal circulation by phagocytes. We have demonstrated in a human in vitro system that mAb 26.4 (IgG1 and IgG3) can induce phagocytosis of HPA-1a-positive platelets.

As described above, a notable difference between the 26.4 antibody and the B2G1 antibody is that 26.4 binds more stably to trophoblast-derived αVβ3 and is more efficient at inhibiting binding of anti-HPA-1a antibodies (SZ21) to αVβ3. In terms of prophylactic and therapeutic potential, stable binding to HPA-1a on trophoblasts may be an advantageous property. It is believed that HPA-1a on αVβ3 expressed on trophoblast cells could initiate an alloimmune response in the mother (Vanderpuye O A, et al., (1991), *Biochem J* 280 (Pt 1): 9-17; Kumpel et al. (2008), *Transfusion* 48: 2077-86). Without wishing to be bound by theory, the stable binding of 26.4 to αVβ3 derived from placenta could accelerate removal of cells and material expressing this antigen from the maternal circulation and thereby prevent alloimmunization. Again, without wishing to be bound by theory, an additional mechanism could be masking of epitopes and in effect preventing HPA-1a-specific B cells from binding antigen and thereby prevent their activation. Removal from the circulation could also prevent activation of such B cells.

In conclusion, we have developed a novel HPA-1a-specific antibody derived from a single B cell of a woman HPA-1a alloimmunized in connection with pregnancy. The antibody has no detectable cross reactivity with the HPA-1b allotype. The recombinant version of this antibody may be used as a diagnostic reagent to identify the individuals at risk of HPA-1a immunization as well as a prophylactic reagent to prevent FNAIT and/or as a therapeutic agent to treat FNAIT.

Example 2 a Novel Human Recombinant Monoclonal HPA-1a-Specific Antibody is a Useful Tool for Diagnostics in Fetal and Neonatal Alloimmune Thrombocytopenia Introduction Currently, there is no safe and effective prevention or treatment of the condition and the majority of FNAIT cases are diagnosed after birth of a severely thrombocytopenic child. It will be important to identify women at risk of immunization which could benefit from the prophylactic treatment.

Several prospective studies found that high levels of maternal anti-HPA-1a antibodies correlate with low platelet count in the newborn. Therefore, quantitation of anti-HPA-1a antibodies can be used as a predictive factor of the degree of thrombocytopenia in the newborn. Currently used reference material for anti-HPA-1a antibody quantitation was prepared by the National Institute of Biological Standards and Control (NIBSC). This NIBSC standard contains plasma from six HPA-1a immunized donors and its supply is dependent on the availability of such donors.

In the present studies, a novel HPA-1a-specific human recombinant monoclonal antibody, clone 26.4, has been generated. This mAb can be used as a reagent for HPA-1 phenotyping as well as a standard for quantitation of anti-HPA-1a antibodies.

The aim of the study was to evaluate whether the human HPA-1a-specific mAb, clone 26.4, can distinguish HPA-1a and HPA-1b antigens in a whole blood flow cytometry assay. The second aim was to evaluate whether this mAb can be used as a standard for quantitative MAIPA assay.

Materials and Methods

Donor Blood Samples

Peripheral blood was obtained from random healthy blood donor volunteers that have agreed to donate samples that could be used for research purposes (Blood Bank, University Hospital of North Norway). The HPA-1a immunized women donated blood after signing a written informed consent (study was approved by Regional Committee for Medical Research Ethics, North-Norway, approval no: 2009/1585).

Antibodies

An HPA-1a-specific mAb IgG1, clone 26.4, was generated by immortalization of antigen-specific memory B cells from a woman HPA-1a immunized in connection with pregnancy and expressed recombinantly. The IgG1 was purified from cell culture supernatant by 40% saturated ammonium sulphate precipitation followed by Protein G affinity chromatography (Protein G Sepharose 4 FastFlow, GE Healthcare).

The established WHO international reference reagent for quantitation of anti-HPA-1a antibodies was obtained from the National Institute for Biological Standards and Controls (NIBSC, code 03/152) (Allen D, et al. Vox Sanguinis. 2005; 89(2):100-4).

HPA-1 Genotyping

Donor samples were HPA-1 genotyped using TaqMan 5' nuclease assay as described previously (Bugert P, McBride S, Smith G, Dugrillon A, Klüter H, Ouwehand W H, et al. Transfusion. 2005; 45(5):654-9).

HPA-1 Phenotyping by Whole Blood Flow Cytometry

Purified mAb 26.4 IgG1 was conjugated with Alexa Fluor 488 fluorescent dye according to the manufacturer instructions (Molecular Probes). The degree of labeling (DOL) was calculated using formula: mole dye/mole protein. Forty microliters of the mAb diluted in PBS containing 0.3% EDTA and 0.2% BSA were added to 10 µl EDTA-anticoagulated whole blood and incubated for 10 minutes at RT in the dark. After adding 0.5 ml of PBS 0.3% EDTA 0.2% BSA buffer the samples were analyzed by flow cytometry (FACSCanto, BD Biosciences). HPA-1aa and HPA-1bb platelets were used as controls. Median FITC fluorescence intensities (MFI) of the controls and each sample were recorded. Flow cytometry data was analysed by FlowJo software (TreeStar, Ashland, Oreg., USA). The blood samples were HPA-1 phenotyped within 10 days of storage, as older samples were viscous and difficult to pipette.

Probing mAb 26.4 as a Standard for Anti-HPA-1a Antibody Quantitation by MAIPA

Purified mAb 26.4 IgG1 was buffer exchanged into phosphate-buffered saline (PBS) containing 0.02% sodium azide and bovine serum albumin (BSA) was added to a concentration of 0.5%. The concentration of mAb was determined by ELISA as described in Example 1. The mAb26.4 was quantified by monoclonal antibody immobilization of platelet antigens (MAIPA) assay with mouse anti-human CD61, clone Y2/51 (Dako, Denmark), used as a capture antibody (Killie M K, Salma W, Bertelsen E, Skogen B, Husebekk A. 2010; 43(2):149-54). MAIPA was originally described by Kiefel et al. (supra); the modified rapid protocol with the reagents is recommended by NIBSC (Modified Rapid MAIPA Assay. http://www.nibsc.org, and Kjeldsen-Kragh J, Killie M K, Tomter G, Golebiowska E, Randen I, Hauge R, et al. Blood. 2007; 110(3):833-9).

Replicate doubling dilutions (1:8-1:512) of the international polyclonal anti-HPA-1a NIBSC standard together with the mAb 26.4 preparation were used to create a linear standard curve. Four plasma samples with different levels of anti-HPA-1a antibodies were tested against HPA-1aa platelets. The levels of specific antibodies in the samples were calculated using linear regression equation.

To assess the intra-assay variability (accuracy) the samples were tested in triplicates. Intra assay coefficient of variation (intra assay CV) is the average of the individual CVs and calculated using formula: % CV=Mean of SD×100/Mean. To assess the inter-assay variability (reproducibility) the assay was repeated three times. It is expressed by inter assay coefficient of variation (inter assay CV) and calculated following formula: % CV=SD of Mean×100/Mean.

Results

MAb 26.4 IgG1 is a Potential HPA-1a Phenotyping Reagent

To test whether mAb 26.4 IgG1 can distinguish between HPA-1a and HPA-1b platelets in whole blood samples, first, we fluorescently labeled the mAb with AlexaFuor 488 dye. The degree of labeling (DOL) was calculated to be around 3 (recommended by the manufacturer optimal DOL should be ~2 fluorophores per antibody). We determined the amount of the AlexaFuor 488-conjugated mAb that allowed us to distinguish HPA-1a-positive from -negative samples (FIG. 8).

We phenotyped 143 donor blood samples (random donor samples together with samples from the individuals with known HPA-1 genotype, Table A).

TABLE A

| HPA-1 genotyped and phenotyped donor blood samples. | | | |
|---|---|---|---|
| Total number of samples | HPA-1aa | HPA-1ab | HPA-1bb |
| 143 | 98 | 30 | 15 |

The recorded median FITC fluorescence intensities (MFI) of all the HPA-1a-positive samples were significantly higher (5 times or more) than the MFI of the HPA-1a-negative samples. All the blood samples were HPA-1 genotyped. In the collection of tested blood samples, we detected no phenotype-genotype discrepancies.

MAb 26.4 IgG1 can be Used as a Standard for Detection and Quantitation of Anti-HPA-1a Antibodies by MAIPA Assay To evaluate the use of mAb 26.4 IgG1 as a standard in quantitative MAIPA we aligned MAb 26.4 IgG1 with the international polyclonal anti-HPA-1a NIBSC standard. At a concentration 5 µg/ml the mAb had anti-HPA-1a activity corresponding to 100 IU/ml.

We compared plots generated by mean absorbance values for replicate doubling dilutions of the international polyclonal anti-HPA-1a NIBSC standard and the mAb 26.4 IgG1 standard in MAIPA assay. The linearity and range of the two standards were comparable (FIG. 9). The linear portions of the plots were used to determine the anti-HPA-1a antibody levels of the samples. The mean values of anti-HPA-1a activities in samples A, B, C and D measured in three assays are presented in FIG. 10.

Intra assay variation describes the variation of results within a data set obtained from one experiment (accuracy). The intra-assay CVs (n=12) were calculated to be around 6% for both, NIBSC and mAb 26.4. The inter assay variation describes the variation of results obtained from repeated experiments (reproducibility). The inter-assay CVs (n=3) were calculated to be around 9% and 10% for NIBSC and mAb 26.4 as standards respectively.

Discussion

There is a demand for a reagent that could be used to establish a simple and reliable technique to identify HPA-1a-negative individuals. The HPA-1a genotyping techniques are reliable but time consuming or require sophisticated equipment. The commercially available ELISA-based assay is expensive and unreliable due to false positive results. The two previously published flow cytometry-based assays rely on SZ21 antibody. The SZ21 mAb is pseudospecific to the HPA-1a; it binds to HPA-1a-negative platelets in increasing antibody concentrations. A highly specific for HPA-1a mAb would be advantageous for the phenotyping assays reducing the probability of false positive results.

To validate whether a novel human HPA-1a-specific mAb 26.4 can distinguish HPA-1a from –b allotype in whole blood samples, we HPA-1 phenotyped 143 whole blood samples using the fluorophore-conjugated 26.4 to and found no phenotype-genotype discrepancies. The whole blood flow cytometry-based HPA-1 phenotyping using this mAb is a rapid and reliable technique suitable for screening purposes.

Phenotyping may be supplemented with genotyping of the identified HPA-1a-negative samples.

Quantitation of the anti-HPA-1a antibodies has a predictive value in diagnosis of FNAIT. The available from NIBSC anti-HPA-1a reference material (NIBSC code: 03/152) consists of pooled plasma from several HPA-1a immunized donors and its supply is dependent on the availability of such donors. We reasoned that the recombinant monoclonal antibody would facilitate an unlimited supply of a standardized and relatively inexpensive reagent. We found that the 26.4 shows high accuracy and reproducibility, similar to the NIBSC reference material, when used as a standard for quantitation of samples with different anti-HPA-1a antibody levels.

Example 3

MAb 26.4 Inhibits Binding of Polyclonal Anti-HPA-1a IgG to Platelets

MAIPA Inhibition Assay

MAb 26.4 F(ab')$_2$ fragment was prepared using Pierce F(ab')$_2$ Preparation Kit (Pierce, Appleton, Wis.). The purified F(ab')$_2$ fragment concentration (0.7 mg/ml) was determined by spectrophotometry from the absorbance at 280 nm using an extinction coefficient of 1.4 L×g$^{-1}$×cm$^{-1}$. The ability of 26.4 to block binding of polyclonal maternal anti-HPA-1a IgG antibodies was evaluated by a modified adaptation of the MAIPA technique (Griffin H, Ouwehand W. 1995. *Blood* 86: 4430-6). Briefly, HPA-1a homozygous fresh platelets (2×10$^7$) were incubated with 50 µl of 26.4 F(ab')$_2$ for 1 h at RT before adding 100 µl of diluted 1:10 serum samples for 15 min. Further, the MAIPA assay was performed as described previously (Kiefel V et al. 1987. *Blood* 70: 1722-6; Killie M K et al. 2010. *Transfusion and Apheresis Science* 43: 149-54). We tested a panel of 10 donor serum samples with anti-HPA-1a activity ranging from 10 to 150 IU/ml as measured by quantitative MAIPA (Killie M K et al. 2010. *Transfusion and Apheresis Science* 43: 149-54).

One potential therapeutic use of mAb 26.4 would involve blocking access of pathogenic anti-HPA-1a antibodies to fetal platelets. Therefore, we tested the capacity of 26.4 to inhibit binding of maternal polyclonal anti-HPA-1a IgG using the MAIPA technique. Binding to HPA-1a homozygous platelets in 10 out of 10 samples was considerably inhibited after preincubation of platelets with 26.4 F(ab')$_2$ fragment. The inhibition ranged from 65% to 100% at a highest fragment concentration of 35 µg in 50 µl volume (FIG. 11). GraphPad Prism 5 software (San Diego, Calif.) was used to present MAIPA inhibition assay data.

Without wishing to be bound by theory, it is believed that antibodies which have a reduced or abolished effector function (e.g. a F(ab')$_2$ fragment of 26.4) would be useful in FNAIT treatment as such antibodies would cross the placenta and bind fetal platelets, thereby hindering binding of functional maternal anti-HPA-1a IgG antibodies and protecting fetal tissues and platelets from potentially damaging maternal anti-HPA-1a antibodies. The demonstration that mAb 26.4 can efficiently block maternal polyclonal HPA-1a-specific IgG from various donors from binding platelets suggests that the mAb could also interfere with binding to receptors on HPA-1a-specific B cell clones in women susceptible to immunization.

Example 4

Domain Deletion Peptide ELISA

Anti-HPA-1a antibodies are heterogeneous in their footprint on the $\beta_3$ integrin and are categorized as type I and type II antibodies (Liu L X et al., *Blood*, 1996; 88(9):3601-7; Valentin N et al., *Blood*, 1995; 85(11):3028-33; Stafford P et al. *Journal of Thrombosis and Haemostasis*, 2008; 6(2):366-75). Type I antibodies bind to the residues within the plexin/semaphorin/integrin (PSI) domain, the first 54 residues of the $\beta_3$ integrin which contain the HPA-1 polymorphism at position 33. The epitope of the type II antibodies spans to the residues distant from the PSI domain—the hybrid and epidermal growth factor (EGF) domains.

It was decided to test whether 26.4 epitope is constrained to PSI domain or spans several domains of the $\beta_3$ integrin. To study this, the domain-deletion peptide ELISA technique described previously was employed (Stafford P et al. *Journal of Thrombosis and Haemostasis*, 2008; 6(2):366-75).

Materials

Antibodies

Integrin $\beta_3$-specific murine mAb clones Y2/51 (Beckman Coulter, Pasadena, Calif.) and SZ21 (Dako, Glostrup, Denmark) were used. Integrin αIIb-specific mAb clone SZ22 (Beckman Coulter, Pasadena, Calif.) was used. Human mAb specific for HPA-1a, clone B2G1 was isolated from maternal B cells of a case of FNAIT using phage display (Griffin H, Ouwehand W, Blood 1995; 86(12):4430-6) and produced recombinantly (Garner et al., *British Journal of Haematology*, 2000; 108(2):440-7) (kindly provided by Cedric Ghevaert, Department of Hematology, School of Clinical Medicine, University of Cambridge, UK). MAb 26.4 derived from a single B cell isolated from a woman HPA-1a-immunized in connection with pregnancy (described herein). Horseradish peroxidase (HRP)-conjugated goat anti-mouse IgG and HRP-conjugated goat anti-human IgG (Jackson ImmunoResearch Laboratories, West Grove, Pa.) were used as secondary antibodies.

Recombinant Domain-Deleted Peptides

The following peptides were used: ΔβA-Leu33, ΔβA-Pro33, PSI-Leu33, and GPVI (hDID2) as a negative control (peptides kindly provided by Rosey Mushens, International Blood Group Reference Laboratory, NHS Blood and Transplant, Filton, Bristol, UK; Winnie Chong, Department of Histocompatibility and Immunogenetics, NHS Blood and Transplant, Colindale Avenue, London, UK; Willem H Ouwehand, University of Cambridge & Welcome Trust Sanger Institute, NHS Blood and Transplant, UK; Stafford P et al. describe these peptides in *Journal of Thrombosis and Haemostasis*, 2008; 6(2):366-75). CaM-binding peptide N9A coupled to BSA was kindly provided by Peter Smethurst and Nicola Foad (described by Smethurst P A et al., *Blood* 2004; 103(3):903-11).

Methods

Cloning, expression and purification of the recombinant domain-deletion peptides with calmodulin (CaM) tag is described in Stafford et al. (*Journal of Thrombosis and Haemostasis*, 2008; 6(2):366-75). ELISA was performed as described previously (Abou-Chaker K et al., *Tissue Antigens* 2009; 73(3):242-4). Briefly, the $\beta_3$ peptides were immobilized to ELISA plates via CaM-binding peptide N9A coupled to BSA (Smethurst P A et al., *Blood* 2004; 103(3): 903-11). Murine and human mAbs were used at concentrations of 1 and 10 μg/ml. MAb binding was detected by HRP-conjugated goat-anti-mouse IgG or HRP-conjugated goat-anti-human IgG. Absorbance at 492 nm was read on an microplate photometer (*Multiskan EX, Thermo Scientific*, Waltham, Mass.). Each sample was tested in duplicate and average absorbance values were used to generate the graph (FIG. 12 and FIG. 13).

Results

Binding of the murine mAbs, clones Y2/51 and SZ21, to domain-deletion peptides was published previously (Stafford P et al., *Journal of Thrombosis and Haemostasis*, 2008; 6(2):366-75) and was used as a system control. MAb Y2/51 at concentrations of 1 and 10 μg/ml bound the multi-domain peptide ΔβA, Leu33 and Pro33, variants. MAb SZ21 at 1 μg/ml bound to ΔβA-Leu33, when binding to ΔβA-Pro33 and PSI-Leu33 generated relatively low response. MAb SZ21 at 10 μg/ml bound multi-domain peptides ΔβA, independently on Leu33 or Pro33 variant, as well as a single-domain peptide PSI-Leu33. None of the mAbs bound to the control peptide. The results were consistent with the previously published (Stafford P et al. *Journal of Thrombosis and Haemostasis*, 2008; 6(2):366-75). MAb SZ22 (specific to αIIb, CD41) was used as a murine mAb negative control and did not bind neither of the peptides (data not shown).

MAb 26.4 bound exclusively to the multi-domain peptide ΔβA-Leu33; no binding to the ΔβA-Pro33, single-domain peptide PSI-Leu33 or peptide negative control was observed. MAb B2G1 had an identical binding pattern, consistent with the previously published results (Stafford P et al., *Journal of Thrombosis and Haemostasis*, 2008; 6(2): 366-75).

The results described above suggest that epitope of the 26.4 spans several domains of $\beta_3$ integrin, and 26.4 is a type II anti-HPA-1a antibody.

The invention claimed is:

1. An isolated antibody that specifically binds to HPA-1a and that comprises at least one heavy chain variable region that comprises three CDRs and at least one light chain variable region that comprises three CDRs, wherein said light chain variable region comprises:

(a) a variable light (VL) CDR1 that has the amino acid sequence of SEQ ID NO:8;

(b) a VL CDR2 that has the amino acid sequence of SEQ ID NO:9; and (c) a VL CDR3 that has the amino acid sequence of SEQ ID NO: 10;

and wherein said heavy chain variable region comprises:

(d) a variable heavy (VH) CDR1 that has the amino acid sequence of SEQ ID NO:5;

(e) a VH CDR2 that has the amino acid sequence of SEQ ID NO:6; and
(f) a VH CDR3 that has the amino acid sequence of SEQ ID NO:7.

2. The antibody according to claim 1, wherein said light chain variable region has the amino acid sequence of SEQ ID NO:4, or a sequence having at least 80% sequence identity thereto and/or wherein said heavy chain variable region has the amino acid sequence of SEQ ID NO:3, or a sequence having at least 80% sequence identity thereto.

3. The antibody according to claim 1, wherein said light chain variable region has the amino acid sequence of SEQ ID NO:4 and said heavy chain variable region has the amino acid sequence of SEQ ID NO:3.

4. The antibody according to claim 1, wherein said antibody is a full length IgG antibody.

5. The antibody according to claim 4, wherein said antibody
  (i) has a heavy chain that comprises the amino acid sequence of SEQ ID NO:21 or a sequence having at least 80% sequence identity thereto and/or a light chain that comprises the amino acid sequence of SEQ ID NO:22 or a sequence having at least 80% sequence identity thereto, or
  (ii) has a heavy chain that comprises the amino acid sequence of SEQ ID NO:25 or a sequence having at least 80% sequence identity thereto and/or a light chain that comprises the amino acid sequence of SEQ ID NO:26 or a sequence having at least 80% sequence identity thereto.

6. The antibody according to claim 4, wherein said antibody
  (i) has a heavy chain that comprises the amino acid sequence of SEQ ID NO:21 and a light chain that comprises the amino acid sequence of SEQ ID NO:22, or
  (ii) has a heavy chain that comprises the amino acid sequence of SEQ ID NO:25 and a light chain that comprises the amino acid sequence of SEQ ID NO:26.

7. The antibody according to claim 1, wherein said antibody is capable of binding to αVβ3 integrin containing the HPA-1a antigen.

8. The antibody according to claim 1, wherein said antibody remains at least 35% bound to a purified and immobilised αVβ3 integrin from HPA-1a positive individuals at the end of the dissociation period in a Surface Plasmon Resonance assay.

9. The antibody according to claim 1, wherein said antibody binds to HPA-1a on intact platelets.

10. The antibody according to claim 1, wherein said antibody is capable of binding to purified aIIbβ3 platelet integrin from HPA-1a positive individuals.

11. The antibody according to claim 1, wherein said antibody is capable of inducing phagocytosis of HPA-1a positive platelets.

12. The antibody according to claim 1, wherein said antibody does not inhibit aggregation of HPA-1bb platelets.

13. The antibody according to claim 1, wherein said antibody has an abolished effector function.

14. A method of producing an antibody according to claim 1, comprising the steps of
  (i) culturing a host cell comprising one or more nucleic acid molecules comprising a nucleotide sequence that encodes an antibody according to claim 1 or one or more recombinant expression vectors comprising one or more of said nucleic acid molecules under conditions suitable for the expression of the encoded antibody; and
  (ii) isolating or obtaining the antibody or protein from the host cell or from the growth medium/supernatant.

15. A method for analysing for the presence or absence of HPA-1a in a sample that has been obtained from a subject, said method comprising the steps of
  (a) contacting said sample with an antibody according to claim 1 which binds specifically to HPA-1a; and
  (b) analysing for the presence or absence of anti-HPA-1a antibody-HPA-1a (antigen) complexes.

16. A method of quantifying anti-HPA-1a antibodies in a sample in which method an antibody according to claim 1 is used as a reference standard.

17. The antibody according to claim 1, wherein said antibody is not fucosylated.

* * * * *

SEQUENCE LISTING

<160> NUMBER OF SEQ ID NOS: 30

<210> SEQ ID NO 1
<211> LENGTH: 405
<212> TYPE: DNA
<213> ORGANISM: human

<400> SEQUENCE: 1

```
caggtacagt tgcagcagtc aggtccagga ctggtgaagc cctcgcagac cctgtcactc      60
acctgtgcca tctccgggga cagtgtcagc agcaacagtg ctgcttggaa ctggatcagg     120
cagtccccat cgagaggcct tgagtggctg ggaaggacat acttcaggtc caactggtac     180
aatgattatg cagcatctgt gaaaagtcga ataaccatca accaagacac atccaagaac     240
cagctctccc tgcagctgaa ctctgtgact cccgaggaca cggctatgta ttactgtgca     300
agagatgggg cctggggtgg cagcagctgg tggccaggcc ttcctcacca ctactactct     360
ggtatggacg tctggggcca ggggaccacg gtcaccgtct cctca                      405
```

<210> SEQ ID NO 2
<211> LENGTH: 324
<212> TYPE: DNA
<213> ORGANISM: human

<400> SEQUENCE: 2

```
gaaattgtgt tgacacagtc tccagccacc ctgtcattgt ctccagggga aagagccacc      60
ctctcctgca gggccagtca gagtgttagc agctacttag cctggtacca acagaagcct     120
```

```
ggccaggctc ccaggctcct catctatgat gcatccaaaa gggccactgg catcccagcc      180
aggttcagtg gcagtgggtc tgggacagac ttcagtctca ccatcagaag cctcgagcct      240
gaagattttg cagtttatta ctgtcaacag cgtagcgact ggcagggact cactttcggc      300
ggagggacca aggtggagat caaa                                             324
```

```
<210> SEQ ID NO 3
<211> LENGTH: 135
<212> TYPE: PRT
<213> ORGANISM: human

<400> SEQUENCE: 3
```

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Phe Arg Ser Asn Trp Tyr Asn Asp Tyr Ala
    50                  55                  60

Ala Ser Val Lys Ser Arg Ile Thr Ile Asn Gln Asp Thr Ser Lys Asn
65                  70                  75                  80

Gln Leu Ser Leu Gln Leu Asn Ser Val Thr Pro Glu Asp Thr Ala Met
                85                  90                  95

Tyr Tyr Cys Ala Arg Asp Gly Ala Gly Gly Ser Trp Trp Pro
            100                 105                 110

Gly Leu Pro His His Tyr Tyr Ser Gly Met Asp Val Trp Gly Gln Gly
        115                 120                 125

Thr Thr Val Thr Val Ser Ser
    130                 135

```
<210> SEQ ID NO 4
<211> LENGTH: 108
<212> TYPE: PRT
<213> ORGANISM: human

<400> SEQUENCE: 4
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Ser Leu Thr Ile Arg Ser Leu Glu Pro
65                  70                  75                  80

Glu Asp Phe Ala Val Tyr Tyr Cys Gln Gln Arg Ser Asp Trp Gln Gly
                85                  90                  95

Leu Thr Phe Gly Gly Gly Thr Lys Val Glu Ile Lys
            100                 105

```
<210> SEQ ID NO 5
<211> LENGTH: 10
<212> TYPE: PRT
<213> ORGANISM: human
```

```
<400> SEQUENCE: 5

Gly Asp Ser Val Ser Ser Asn Ser Ala Ala
1               5                   10

<210> SEQ ID NO 6
<211> LENGTH: 9
<212> TYPE: PRT
<213> ORGANISM: human

<400> SEQUENCE: 6

Thr Tyr Phe Arg Ser Asn Trp Tyr Asn
1               5

<210> SEQ ID NO 7
<211> LENGTH: 25
<212> TYPE: PRT
<213> ORGANISM: human

<400> SEQUENCE: 7

Ala Arg Asp Gly Ala Trp Gly Gly Ser Ser Trp Trp Pro Gly Leu Pro
1               5                   10                  15

His His Tyr Tyr Ser Gly Met Asp Val
            20                  25

<210> SEQ ID NO 8
<211> LENGTH: 6
<212> TYPE: PRT
<213> ORGANISM: human

<400> SEQUENCE: 8

Gln Ser Val Ser Ser Tyr
1               5

<210> SEQ ID NO 9
<211> LENGTH: 3
<212> TYPE: PRT
<213> ORGANISM: human

<400> SEQUENCE: 9

Asp Ala Ser
1

<210> SEQ ID NO 10
<211> LENGTH: 10
<212> TYPE: PRT
<213> ORGANISM: human

<400> SEQUENCE: 10

Gln Gln Arg Ser Asp Trp Gln Gly Leu Thr
1               5                   10

<210> SEQ ID NO 11
<211> LENGTH: 25
<212> TYPE: PRT
<213> ORGANISM: human

<400> SEQUENCE: 11

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25
```

```
<210> SEQ ID NO 12
<211> LENGTH: 17
<212> TYPE: PRT
<213> ORGANISM: human

<400> SEQUENCE: 12

Trp Asn Trp Ile Arg Gln Ser Pro Ser Arg Gly Leu Glu Trp Leu Gly
1               5                   10                  15

Arg

<210> SEQ ID NO 13
<211> LENGTH: 38
<212> TYPE: PRT
<213> ORGANISM: human

<400> SEQUENCE: 13

Asp Tyr Ala Ala Ser Val Lys Ser Arg Ile Thr Ile Asn Gln Asp Thr
1               5                   10                  15

Ser Lys Asn Gln Leu Ser Leu Gln Leu Asn Ser Val Thr Pro Glu Asp
            20                  25                  30

Thr Ala Met Tyr Tyr Cys
        35

<210> SEQ ID NO 14
<211> LENGTH: 11
<212> TYPE: PRT
<213> ORGANISM: human

<400> SEQUENCE: 14

Trp Gly Gln Gly Thr Thr Val Thr Val Ser Ser
1               5                   10

<210> SEQ ID NO 15
<211> LENGTH: 26
<212> TYPE: PRT
<213> ORGANISM: human

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 16
<211> LENGTH: 17
<212> TYPE: PRT
<213> ORGANISM: human

<400> SEQUENCE: 16

Leu Ala Trp Tyr Gln Gln Lys Pro Gly Gln Ala Pro Arg Leu Leu Ile
1               5                   10                  15

Tyr

<210> SEQ ID NO 17
<211> LENGTH: 36
<212> TYPE: PRT
<213> ORGANISM: human
```

<400> SEQUENCE: 17

Lys Arg Ala Thr Gly Ile Pro Ala Arg Phe Ser Gly Ser Gly
1               5                   10                  15

Thr Asp Phe Ser Leu Thr Ile Arg Ser Leu Glu Pro Glu Asp Phe Ala
            20                  25                  30

Val Tyr Tyr Cys
        35

<210> SEQ ID NO 18
<211> LENGTH: 10
<212> TYPE: PRT
<213> ORGANISM: human

<400> SEQUENCE: 18

Phe Gly Gly Gly Thr Lys Val Glu Ile Lys
1               5                   10

<210> SEQ ID NO 19
<211> LENGTH: 1398
<212> TYPE: DNA
<213> ORGANISM: human

<400> SEQUENCE: 19

```
caggtgcagc tgcagcagtc cggccctggg ctggtgaagc ctagccagac cctgtccctg    60
acatgcgcca tctcaggcga cagcgtgagc tccaactctg ccgcttggaa ttggattaga   120
cagagcccat cccgcgggct ggagtggctg gacggaccta cttcagaaag caactggtac   180
aatgactatg ccgcttccgt gaagtctcgg atcaccatta accaggatac atctaaaaat   240
cagctgagtc tgcagctgaa ctcagtgact cccgaagaca ccgccatgta ctattgtgct   300
agggatggcg cttggggcgg gtctagttgg tggccaggac tgccccacca ttactatagc   360
ggcatggacg tgtggggaca gggcaccaca gtgacagtgt caagcgccag cactaagggc   420
ccttccgtgt ttcctctggc tccatcctct aaatctacaa gtggaggcac tgccgctctg   480
gggtgtctgg tgaaggatta tttccctgag ccagtgactg tgagttggaa ctcaggcgcc   540
ctgactagcg gggtgcacac ctttcccgct gtgctgcaga gttcagggct gtacagcctg   600
agctccgtgg tgaccgtgcc ttctagttca ctgggaactc agacctatat ctgcaacgtg   660
aatcacaagc cttctaatac aaaagtggac aagaaagtgg agccaaagag ttgtgataaa   720
acacatactt gccctcccctg ccctgccccct gaactgctgg gcggcccaag cgtgttcctg   780
tttccaccca gcccaaaga tacactgatg attagccgga ctccggaggt cacatgcgtg   840
gtggtggacg tgagccacga ggatcctgaa gtgaagttca actggtacgt ggacggcgtg   900
gaagtgcata atgccaagac caaaccacgg gaggaacagt acaactctac atatagagtg   960
gtgagtgtgc tgactgtgct gcaccaggat tggctgaacg gaaagagta taagtgcaaa  1020
gtgagcaata aggccctgcc tgctccaatc gagaaaacca tttccaaggc caaaggacag  1080
cccagggaac ctcaggtgta cactctgccc cctagtcgcg acgagctgac taagaaccag  1140
gtgtctctga cctgtctggt gaaaggcttc tatccatccg atatcgctgt ggagtgggaa  1200
tctaatgggc agcccgaaaa caattacaag accacaccac cgtgctggaa cagcgatgga  1260
tccttctttc tgtattcaaa gctgactgtg gacaaaagcc ggtggcagca gggcaacgtg  1320
tttagctgtt ccgtgatgca tgaggctctg cacaatcatt acacccagaa gtctctgagt  1380
ctgtcacccg ggaaatga                                                1398
```

-continued

```
<210> SEQ ID NO 20
<211> LENGTH: 648
<212> TYPE: DNA
<213> ORGANISM: human

<400> SEQUENCE: 20
gagatcgtgc tgactcagtc tccagccacc ctgtccctgt ctccaggaga acgggccact    60
ctgtcttgca gagctagtca gtcagtgagc tcctacctgg cctggtatca gcagaagcca   120
ggacaggctc cccggctgct gatctacgac gcctccaaaa gggctacagg cattcccgct   180
cgcttcagcg gctccgggtc tggaacagat ttttccctga ctatcagaag cctggagcct   240
gaagacttcg ccgtgtacta ttgccagcag agatctgatt ggcagggggct gacctttggc   300 ggggaacaa aggtggagat caaaaggacc gtggccgctc caagcgtgtt catctttccc   360
cctagcgacg aacagctgaa gtcagggaca gccagcgtgg tgtgcctgct gaacaatttc   420 taccccgcg aggccaaggt gcagtggaaa gtggataacg ctctgcagag tggaaattca   480
caggagagcg tgactgaaca ggactccaag gattctacct atagtctgtc tagtaccctg   540
acactgagca agccgactac gagaagcac aaagtgtatg cttgcgaagt gacacatcag   600
ggcctgtcaa gccctgtgac taagagcttc aaccggggcg agtgttga                648

<210> SEQ ID NO 21
<211> LENGTH: 465
<212> TYPE: PRT
<213> ORGANISM: human

<400> SEQUENCE: 21

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Phe Arg Ser Asn Trp Tyr Asn Asp Tyr Ala
    50                  55                  60

Ala Ser Val Lys Ser Arg Ile Thr Ile Asn Gln Asp Thr Ser Lys Asn
65                  70                  75                  80

Gln Leu Ser Leu Gln Leu Asn Ser Val Thr Pro Glu Asp Thr Ala Met
                85                  90                  95

Tyr Tyr Cys Ala Arg Asp Gly Ala Trp Gly Ser Ser Trp Trp Pro
            100                 105                 110

Gly Leu Pro His His Tyr Tyr Ser Gly Met Asp Val Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220
```

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
            245                 250                 255

Ser Val Phe Leu Phe Pro Pro Lys Pro Lys Asp Thr Leu Met Ile Ser
        260                 265                 270

Arg Thr Pro Glu Val Thr Cys Val Val Val Asp Val Ser His Glu Asp
    275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Pro Ile Glu Lys
        340                 345                 350

Thr Ile Ser Lys Ala Lys Gly Gln Pro Arg Glu Pro Gln Val Tyr Thr
    355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
        420                 425                 430

Ser Arg Trp Gln Gln Gly Asn Val Phe Ser Cys Ser Val Met His Glu
    435                 440                 445

Ala Leu His Asn His Tyr Thr Gln Lys Ser Leu Ser Leu Ser Pro Gly
450                 455                 460

Lys
465

<210> SEQ ID NO 22
<211> LENGTH: 215
<212> TYPE: PRT
<213> ORGANISM: human

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Ser Leu Thr Ile Arg Ser Leu Glu Pro
65                  70                  75                  80

Glu Asp Phe Ala Val Tyr Tyr Cys Gln Gln Arg Ser Asp Trp Gln Gly
            85                  90                  95

Leu Thr Phe Gly Gly Gly Thr Lys Val Glu Ile Lys Arg Thr Val Ala
        100                 105                 110

Ala Pro Ser Val Phe Ile Phe Pro Pro Ser Asp Glu Gln Leu Lys Ser
    115                 120                 125

```
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 23
<211> LENGTH: 1545
<212> TYPE: DNA
<213> ORGANISM: human

<400> SEQUENCE: 23
caggtgcagc tgcagcagtc cgggccagga ctggtgaaaa cctcacagac actgagcctg      60
acttgtgcca tcagtggcga ttcagtgagc tccaacagcg ccgcttggaa ttggattagg     120
cagagtcctt cacgcggact ggaatggctg ggccggacct acttcagatc caactggtac     180
aatgactatg ccgccagcgt gaagtcccgg atcacaatta ccaggatac ttccaaaaat     240 cagctgtctc tgcagctgaa cagtgtgacc ccagaggaca cagccatgta ctattgcgcc     300
agagatgggg cttggggcgg gtctagttgg tggccaggcc tgccccacca ttactatagc     360
gggatggacg tgtggggaca gggaaccaca gtgaccgtga gcagcgcctc aaccaagggg     420
cctagcgtgt tcctctggc tccatgcagc aggtccactt ctggaggcac cgccgctctg     480
ggatgtctgg tgaaggacta tttccccgaa cctgtgaccg tgtcttggaa cagtggggcc     540
ctgacctctg gagtgcacac atttcccgct gtgctgcagt cctctggact gtacagcctg     600
agttcagtgg tgaccgtgcc aagctcctct ctgggcacac agacttatac ctgtaacgtg     660
aatcacaagc ccagcaatac aaaggtggac aaacgggtgg agctgaaaac acctctgggc     720
gatactaccc atacttgccc acggtgtcca gagcccaaaa gctgtgacac ccctccccca     780
tgcccaagat gtcctgaacc aaaatcttgt gatacacccc ctccatgccc taggtgtccc     840
gagcctaaga gttgtgacac tccccctcca tgtcctagat gtcctgctcc ggaactgctg     900
ggcggtccga gcgtgtttct gttcccgccg aaaccgaaag ataccctgat gattagtcgc     960
acgccggaag ttacctgcgt ggttgtggat gtgagccatg aagacccgga agttcagttt    1020
aaatggtatg tggatggtgt tgaagtgcac aacgcaaaaa ccaaaccgcg tgaagaacag    1080
tacaatagca cgttccgcgt tgtgtctgtt ctgaccgtgc tgcatcagga ttggctgaac    1140
ggcaaagaat acaaatgtaa agtttctaac aaagcactgc cggcgccgat tgaaaaaacg    1200
atcagtaaaa ccaagggtca gccgcgtgaa ccgcaggtgt acaccctgcc gccgagccgt    1260
gaagaaatga cgaaaaacca gttagtctg acctgcctgg tgaaaggctt ttacccgagc    1320
gatattgcag tggaatggga agctctggt cagccggaaa acaattataa taccacgccg    1380
ccgatgctgg atagtgatgg cagtttttc ctgtatagta aactgaccgt tgataaaagc    1440
cgttggcagc agggtaacat ctttagttgc agcgtgatgc atgaagcgct gcacaatcgc    1500
ttcacccaga aatctctgag tctgagcccg ggcaaaggta aataa                     1545
```

<210> SEQ ID NO 24
<211> LENGTH: 648
<212> TYPE: DNA
<213> ORGANISM: human

<400> SEQUENCE: 24

```
gagatcgtgc tgactcagtc tccagccacc ctgtccctgt ctccaggaga acgggccact    60
ctgtcttgca gagctagtca gtcagtgagc tcctacctgg cctggtatca gcagaagcca   120
ggacaggctc cccggctgct gatctacgac gcctccaaaa gggctacagg cattcccgct   180
cgcttcagcg gctccgggtc tggaacagat ttttccctga ctatcagaag cctggagcct   240
gaagacttcg ccgtgtacta ttgccagcag agatctgatt ggcaggggct gacctttggc   300
ggggggaacaa aggtggagat caaaaggacc gtggccgctc caagcgtgtt catctttccc   360
cctagcgacg aacagctgaa gtcagggaca gccagcgtgg tgtgcctgct gaacaatttc   420
tacccccgcg aggccaaggt gcagtggaaa gtggataacg ctctgcagag tggaaattca   480
caggagagcg tgactgaaca ggactccaag gattctacct atagtctgtc tagtaccctg   540
acactgagca agccgactac gagaagcac aaagtgtatg cttgcgaagt gacacatcag   600
ggcctgtcaa gccctgtgac taagagcttc aaccggggcg agtgttga                648
```

<210> SEQ ID NO 25
<211> LENGTH: 514
<212> TYPE: PRT
<213> ORGANISM: human

<400> SEQUENCE: 25

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Phe Arg Ser Asn Trp Tyr Asn Asp Tyr Ala
    50                  55                  60

Ala Ser Val Lys Ser Arg Ile Thr Ile Asn Gln Asp Thr Ser Lys Asn
65                  70                  75                  80

Gln Leu Ser Leu Gln Leu Asn Ser Val Thr Pro Glu Asp Thr Ala Met
                85                  90                  95

Tyr Tyr Cys Ala Arg Asp Gly Ala Trp Gly Ser Ser Trp Trp Pro
            100                 105                 110

Gly Leu Pro His His Tyr Tyr Ser Gly Met Asp Val Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Cys Ser Arg Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Thr Cys Asn Val Asn His Lys Pro
    210                 215                 220
```

```
Ser Asn Thr Lys Val Asp Lys Arg Val Glu Leu Lys Thr Pro Leu Gly
225                 230                 235                 240

Asp Thr Thr His Thr Cys Pro Arg Cys Pro Glu Pro Lys Ser Cys Asp
            245                 250                 255

Thr Pro Pro Cys Pro Arg Cys Pro Glu Pro Lys Ser Cys Asp Thr
        260                 265                 270

Pro Pro Pro Cys Pro Arg Cys Pro Glu Pro Lys Ser Cys Asp Thr Pro
            275                 280                 285

Pro Pro Cys Pro Arg Cys Pro Ala Pro Glu Leu Leu Gly Gly Pro Ser
        290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Gln Phe Lys Trp Tyr Val Asp Gly Val Glu Val His Asn Ala
                340                 345                 350

Lys Thr Lys Pro Arg Glu Glu Gln Tyr Asn Ser Thr Phe Arg Val Val
            355                 360                 365

Ser Val Leu Thr Val Leu His Gln Asp Trp Leu Asn Gly Lys Glu Tyr
370                 375                 380

Lys Cys Lys Val Ser Asn Lys Ala Leu Pro Ala Pro Ile Glu Lys Thr
385                 390                 395                 400

Ile Ser Lys Thr Lys Gly Gln Pro Arg Glu Pro Gln Val Tyr Thr Leu
                405                 410                 415

Pro Pro Ser Arg Glu Glu Met Thr Lys Asn Gln Val Ser Leu Thr Cys
            420                 425                 430

Leu Val Lys Gly Phe Tyr Pro Ser Asp Ile Ala Val Glu Trp Glu Ser
            435                 440                 445

Ser Gly Gln Pro Glu Asn Asn Tyr Asn Thr Thr Pro Pro Met Leu Asp
        450                 455                 460

Ser Asp Gly Ser Phe Phe Leu Tyr Ser Lys Leu Thr Val Asp Lys Ser
465                 470                 475                 480

Arg Trp Gln Gln Gly Asn Ile Phe Ser Cys Ser Val Met His Glu Ala
                485                 490                 495

Leu His Asn Arg Phe Thr Gln Lys Ser Leu Ser Leu Ser Pro Gly Lys
            500                 505                 510

Gly Lys

<210> SEQ ID NO 26
<211> LENGTH: 215
<212> TYPE: PRT
<213> ORGANISM: human

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Ser Leu Thr Ile Arg Ser Leu Glu Pro
65                  70                  75                  80
```

Glu Asp Phe Ala Val Tyr Tyr Cys Gln Gln Arg Ser Asp Trp Gln Gly
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 122
<212> TYPE: PRT
<213> ORGANISM: human

<400> SEQUENCE: 27

Gln Val Gln Leu Val Gln Ser Gly Ala Glu Val Lys Arg Pro Gly Ala
1               5                   10                  15

Ala Val Lys Val Ser Cys Lys Ala Ser Gly Tyr Arg Phe Thr Gly His
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Met Thr Arg Leu Arg Tyr Asp Asp Thr Ala Val Tyr Tyr Cys
                85                  90                  95

Ala Ala Gly Gly Leu Gly Gly Tyr Tyr Tyr Ala Met Asn Ile Trp
            100                 105                 110

Gly Gln Gly Thr Thr Val Thr Val Ser Ser
        115                 120

<210> SEQ ID NO 28
<211> LENGTH: 110
<212> TYPE: PRT
<213> ORGANISM: human

<400> SEQUENCE: 28

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Trp Val Phe Gly Gly Gly Thr Lys Leu Thr Val Leu
             100                 105                 110

<210> SEQ ID NO 29
<211> LENGTH: 114
<212> TYPE: PRT
<213> ORGANISM: mouse

<400> SEQUENCE: 29

Leu Gln Glu Ser Gly Pro Glu Leu Val Asn Pro Gly Ala Ser Met Lys
  1               5                  10                  15

Ile Ser Cys Lys Ala Ser Gly Tyr Ser Phe Thr Gly Tyr Thr Met Asn
                 20                  25                  30

Trp Val Lys Gln Ser His Gly Lys Asn Leu Glu Trp Ile Gly Leu Ile
             35                  40                  45

Asn Pro Tyr His Gly Gly Ser Ser Tyr Asn Gln Lys Phe Lys Gly Lys
 50                  55                  60

Ala Thr Leu Thr Val Asp Lys Ser Ser Ser Thr Ala Tyr Met Glu Leu
 65                  70                  75                  80

Leu Ser Leu Thr Ser Glu Asp Ser Ala Val Tyr Phe Cys Ala Arg Arg
                 85                  90                  95

Asp Ala Asn Tyr Val Phe Phe Phe Asp Tyr Trp Gly Gln Gly Thr Thr
                100                 105                 110

Val Thr

<210> SEQ ID NO 30
<211> LENGTH: 102
<212> TYPE: PRT
<213> ORGANISM: mouse

<400> SEQUENCE: 30

Glu Leu Thr Gln Ser Pro Ala Leu Met Ser Ala Ser Pro Gly Glu Lys
  1               5                  10                  15

Val Thr Met Thr Cys Ser Ala Ser Ser Gly Val Ser Tyr Ile His Trp
                 20                  25                  30

Tyr Gln Gln Lys Ser Gly Thr Ser Pro Lys Arg Trp Ile Tyr Asp Thr
             35                  40                  45

Ser Lys Leu Ala Ser Gly Val Pro Ala Arg Phe Ser Gly Ser Gly Ser
 50                  55                  60

Gly Thr Ser Tyr Ser Leu Thr Ile Ser Ser Met Glu Ala Glu Asp Ala
 65                  70                  75                  80

Ala Thr Tyr Tyr Cys Gln Gln Trp Ser Ser Lys Pro Pro Thr Phe Gly
                 85                  90                  95

Gly Gly Thr Lys Leu Glu
            100
```